(12) United States Patent
Michelson et al.

(10) Patent No.: US 8,299,081 B2
(45) Date of Patent: Oct. 30, 2012

(54) METHODS FOR TREATING DRUG RESISTANT CANCER

(75) Inventors: Glenn C. Michelson, Emeryville, CA (US); Vivien W. Chan, Emeryville, CA (US); Carla C. Heise, Emeryville, CA (US); Marion Wiesmann, Emeryville, CA (US); Timothy D. Dawes, Emeryville, CA (US)

(73) Assignee: Novartis AG, Basel (CH)

( * ) Notice: Subject to any disclaimer, the term of this patent is extended or adjusted under 35 U.S.C. 154(b) by 439 days.

(21) Appl. No.: 11/913,828

(22) PCT Filed: May 10, 2006

(86) PCT No.: PCT/US2006/017922
§ 371 (c)(1),
(2), (4) Date: Sep. 9, 2008

(87) PCT Pub. No.: WO2006/124413
PCT Pub. Date: Nov. 23, 2006

(65) Prior Publication Data
US 2009/0215793 A1    Aug. 27, 2009

Related U.S. Application Data

(60) Provisional application No. 60/680,722, filed on May 13, 2005.

(51) Int. Cl.
*A61K 31/497* (2006.01)
*A61K 31/535* (2006.01)

(52) U.S. Cl. .............. 514/253.03; 514/234.2; 514/230.5

(58) Field of Classification Search .................... 514/253
See application file for complete search history.

(56) References Cited

U.S. PATENT DOCUMENTS

| | | | |
|---|---|---|---|
| 3,663,606 A | 5/1972 | Isowa | |
| 4,659,657 A | 4/1987 | Harnisch et al. | |
| 4,882,342 A | 11/1989 | Von der Saal et al. | |
| 5,073,492 A | 12/1991 | Chen et al. | |
| 5,151,360 A | 9/1992 | Handa et al. | |
| 5,330,992 A | 7/1994 | Eissenstat et al. | |
| 5,414,088 A | 5/1995 | Von Der Saal et al. | |
| 5,480,883 A | 1/1996 | Spada et al. | |
| 5,585,380 A | 12/1996 | Bianco et al. | |
| 5,646,153 A | 7/1997 | Spada et al. | |
| 5,710,158 A | 1/1998 | Myers et al. | |
| 5,763,441 A | 6/1998 | App et al. | |
| 5,792,771 A | 8/1998 | App et al. | |
| 5,801,212 A | 9/1998 | Okamoto et al. | |
| 5,855,866 A | 1/1999 | Thorpe et al. | |
| RE36,256 E | 7/1999 | Spada et al. | |
| 5,942,385 A | 8/1999 | Hirth | |
| 5,981,569 A | 11/1999 | App et al. | |
| 6,010,711 A | 1/2000 | O'Keefe et al. | |
| 6,057,320 A | 5/2000 | Spada et al. | |
| 6,111,110 A | 8/2000 | Brennan et al. | |
| 6,137,010 A | 10/2000 | Joo et al. | |
| 6,174,912 B1 | 1/2001 | Beck et al. | |
| 6,258,951 B1 | 7/2001 | Lohmann et al. | |
| 6,268,391 B1 | 7/2001 | Dickerson et al. | |
| 6,303,600 B1 | 10/2001 | Cox et al. | |
| 6,306,874 B1 | 10/2001 | Fraley et al. | |
| 6,313,138 B1 | 11/2001 | Fraley et al. | |
| RE37,650 E | 4/2002 | Myers et al. | |
| 6,420,382 B2 | 7/2002 | Fraley et al. | |
| 6,476,068 B1 * | 11/2002 | Lauria et al. | ........... 514/492 |
| 6,479,512 B1 | 11/2002 | Fraley et al. | |
| 6,593,344 B1 | 7/2003 | Biedermann et al. | |
| 6,605,617 B2 | 8/2003 | Renhowe et al. | |
| 6,706,276 B2 | 3/2004 | Garg et al. | |
| 6,756,383 B2 | 6/2004 | Renhowe et al. | |
| 6,759,417 B2 | 7/2004 | Renhowe et al. | |
| 6,762,194 B2 | 7/2004 | Renhowe et al. | |
| 6,774,237 B2 | 8/2004 | Renhowe et al. | |
| 6,774,327 B1 | 8/2004 | Wong | |
| 6,800,760 B2 | 10/2004 | Renhowe et al. | |
| 7,064,215 B2 | 6/2006 | Renhowe et al. | |
| 7,179,912 B2 | 2/2007 | Halbrook et al. | |
| 7,470,709 B2 | 12/2008 | Barsanti et al. | |
| 7,598,268 B2 | 10/2009 | Renhowe et al. | |
| 7,825,132 B2 | 11/2010 | Cai et al. | |
| 2002/0103230 A1 | 8/2002 | Renhowe et al. | |

(Continued)

FOREIGN PATENT DOCUMENTS

AU    2003290699    6/2004

(Continued)

OTHER PUBLICATIONS

Stewart et al. (Phase II study of alternating chemotherapy regimens for advanced non-small cell lung cancer, Lung Cancer, May 2004; 44(2): 241-9.* Rennick et al. (Cancer multidrug resistance, Nature Biotechnology 18, IT18-IT20 (2000).*
Angiogenesis Foundation, "New Study Shows That Acute Myeloid Leukemia is Angiogenesis-Dependent," Jan. 4, 2000; www.angio.org/newsandviews/archive2000/jan_4_2000.html.
Aprelikova, O., et al., "FLT4, a novel Class III Receptor Tyrosine Kinase in chromosome 5q33-qter1," *Cancer Res.*, vol. 52, pp. 746-748, Feb. 1, 1992, published by The American Association for Cancer Research, Stanford University Libraries' High Wire Press, California, United States of America.
Bastin, et al., "Salt Selection and Optimisation Procedures for Pharmaceutical New Chemical Entities," *Organic Process Research & Development*, vol. 4, pp. 427-435, 2000.
Beals, C. R. et al., "Nuclear Export of NF-ATc Enhanced by Glycogen Synthase Kinase-3," *Science*, vol. 275, pp. 1930-1933, Mar. 28, 1997.

(Continued)

*Primary Examiner* — Sreeni Padmanabhan
*Assistant Examiner* — Timothy E Betton
(74) *Attorney, Agent, or Firm* — Cozette M McAvoy

(57) ABSTRACT

A method for treating drug-resistant cancer, includes: administering to a patient in need thereof, a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture, wherein the patient is a cancer patient with drug-resistant cancer, wherein the compound of Formula I is as defined in the application.

20 Claims, 25 Drawing Sheets

U.S. PATENT DOCUMENTS

| | | | |
|---|---|---|---|
| 2002/0107392 A1 | 8/2002 | Renhowe et al. |
| 2003/0028018 A1 | 2/2003 | Renhowe et al. |
| 2003/0087854 A1 | 5/2003 | Monia et al. |
| 2003/0158224 A1 | 8/2003 | Renhowe et al. |
| 2003/0159702 A1 | 8/2003 | Lindell et al. |
| 2003/0207883 A1 | 11/2003 | Renhowe et al. |
| 2004/0002518 A1 | 1/2004 | Renhowe et al. |
| 2004/0006101 A1 | 1/2004 | Renhowe et al. |
| 2004/0092535 A1 | 5/2004 | Barsanti et al. |
| 2004/0097545 A1 | 5/2004 | Renhowe et al. |
| 2004/0220196 A1 | 11/2004 | Hannah et al. |
| 2005/0054672 A1 | 3/2005 | Renhowe et al. |
| 2005/0137399 A1 | 6/2005 | Cai et al. |
| 2005/0203101 A1 | 9/2005 | Barsanti et al. |
| 2005/0209247 A1 | 9/2005 | Cai et al. |
| 2005/0239825 A1 | 10/2005 | Heise et al. |
| 2005/0256157 A1 | 11/2005 | Gesner et al. |
| 2005/0261307 A1 | 11/2005 | Cai et al. |
| 2006/0261307 A1 | 11/2006 | Black et al. |

FOREIGN PATENT DOCUMENTS

| | | |
|---|---|---|
| CA | 2421120 | 3/2002 |
| CL | 23463 | 11/2003 |
| DE | 2363459 | 6/1975 |
| DE | 3634066 | 4/1988 |
| DE | 19841985 | 3/2000 |
| EP | 0 290 153 | 11/1988 |
| EP | 0 508 800 | 10/1992 |
| EP | 0 509 717 | 10/1992 |
| EP | 0 747 771 | 12/1996 |
| EP | 0 797 376 | 9/1997 |
| EP | 1 086 705 | 3/2001 |
| EP | 1 314 425 | 5/2003 |
| HU | P0104752 | 7/2002 |
| JP | 59-130284 | 7/1984 |
| JP | 63230687 | 9/1988 |
| JP | 63-258903 | 10/1988 |
| JP | 02-229165 | 9/1990 |
| JP | 6-9952 | 1/1994 |
| JP | 7-43896 | 2/1995 |
| JP | 8-29973 | 2/1996 |
| JP | 09-182595 | 7/1997 |
| JP | 2002-544209 | 12/2002 |
| WO | WO 91/04974 | 4/1991 |
| WO | WO 92/18483 | 10/1992 |
| WO | WO 92/20642 | 11/1992 |
| WO | WO 94/05333 | 3/1994 |
| WO | WO-94/11337 | 5/1994 |
| WO | WO 95/15758 | 6/1995 |
| WO | WO-95/18622 | 7/1995 |
| WO | WO 95/18801 | 7/1995 |
| WO | WO-96/33980 | 10/1996 |
| WO | WO 97/03069 | 1/1997 |
| WO | WO-97/21436 | 6/1997 |
| WO | WO 97/34876 | 9/1997 |
| WO | WO 97/48694 | 12/1997 |
| WO | WO 98/13350 | 4/1998 |
| WO | WO-98/13354 | 4/1998 |
| WO | WO 98/55124 | 12/1998 |
| WO | WO 99/10349 | 3/1999 |
| WO | WO 99/16755 | 4/1999 |
| WO | WO-99/48868 | 9/1999 |
| WO | WO 99/50263 | 10/1999 |
| WO | WO 99/65897 | 12/1999 |
| WO | WO 00/00481 | 1/2000 |
| WO | WO 00/03990 | 1/2000 |
| WO | WO 00/11709 | 3/2000 |
| WO | WO 00/20400 | 4/2000 |
| WO | WO 00/27379 | 5/2000 |
| WO | WO-00/27820 | 5/2000 |
| WO | WO-00/31049 | 6/2000 |
| WO | WO 00/35492 | 6/2000 |
| WO | WO 00/58315 | 10/2000 |
| WO | WO 00/68223 | 11/2000 |
| WO | WO 00/71129 | 11/2000 |
| WO | WO 00/74683 | 12/2000 |
| WO | WO 01/02369 | 1/2001 |
| WO | WO 01/12169 | 2/2001 |
| WO | WO 01/28993 | 4/2001 |
| WO | WO 01/29025 | 4/2001 |
| WO | WO-01/32651 | 5/2001 |
| WO | WO 01/52875 | 7/2001 |
| WO | WO 01/52904 | 7/2001 |
| WO | WO 01/53268 | 7/2001 |
| WO | WO 01/55114 | 8/2001 |
| WO | WO 01/62251 | 8/2001 |
| WO | WO 01/62252 | 8/2001 |
| WO | WO 01/74296 | 10/2001 |
| WO | WO-01/76573 | 10/2001 |
| WO | WO-02/17913 | 3/2002 |
| WO | WO 02/18383 | 3/2002 |
| WO | WO 02/22598 | 3/2002 |
| WO | WO 02/26716 | 4/2002 |
| WO | WO 02/32861 | 4/2002 |
| WO | WO 02/058697 | 8/2002 |
| WO | WO 03/004488 | 1/2003 |
| WO | WO-03/011226 | 2/2003 |
| WO | WO-03/018134 A2 | 3/2003 |
| WO | WO 03/033472 | 4/2003 |
| WO | WO-03/066630 | 8/2003 |
| WO | WO 03/087095 | 10/2003 |
| WO | 2004018419 A2 * | 3/2004 |
| WO | WO 2004/018419 | 3/2004 |
| WO | WO 2004/030620 | 4/2004 |
| WO | WO 2004/031401 | 4/2004 |
| WO | WO 2004/043389 | 5/2004 |
| WO | WO 2004/063151 | 7/2004 |
| WO | WO 2004/063170 | 7/2004 |
| WO | WO-2004/073631 | 9/2004 |
| WO | WO 2004/087153 | 10/2004 |
| WO | WO-2004/103274 | 12/2004 |
| WO | WO 2005/009967 | 2/2005 |
| WO | WO-2005/037235 | 4/2005 |
| WO | WO-2005/037306 | 4/2005 |
| WO | WO 2005/046589 | 5/2005 |
| WO | WO 2005/046590 | 5/2005 |
| WO | WO 2005/047244 | 5/2005 |
| WO | WO 2005/053692 | 6/2005 |
| WO | WO 2005/082340 | 9/2005 |
| WO | WO 2006/081445 | 8/2006 |
| WO | WO 2006/127926 | 11/2006 |
| WO | WO-2008/008981 | 1/2008 |
| WO | WO-2008/013912 | 1/2008 |

OTHER PUBLICATIONS

Beebe, J. S. et al., "Pharmacological Characterization of CP-547,632, a Novel Vascular Endothelial Growth Factor Receptor-2 Tyrosine Kinase Inhibitor for Cancer Therapy," *Cancer Research*, vol. 63, pp. 7301-7309, Nov. 2003.

Brownlees, J. et al., "Tau phosphorylation in transgenic mice expressing glycogen synthase kinase-3β transgenes," *NeuroReport*, vol. 8, No. 15, pp. 3251-3255, Oct. 20, 1997; published by Rapid Science Publishers.

CAS printout for 300591-52-0 Registry File, entry date into Registry File Oct. 31, 2000.

CAS printout for 304876-79-7 Registry File, entry date into Registry File Nov. 29, 2000.

Chan, T. A. et al., "14-3-3σ is required to prevent mitotic catastrophe after DNA damage," *Nature*, vol. 401, pp. 616-620, Oct. 7, 1999; published by Macmillan Magazines Ltd.

Chen, G. et al., "The Mood-Stabilizing Agent Valproate Inhibits the Activity of Glycogen Synthase Kinase-3," *J. Neurochem.*, vol. 72, No. 3, 1999, pp. 1327-1330; published by Lippincott Williams & Wilkins, Inc., Philadelphia.

Chesi, M. et al., "Activated fibroblast growth factor receptor 3 is an oncogene that contributes to tumor progression in multiple myeloma," *Blood*, vol. 97, No. 3, pp. 729-736, Feb. 1, 2001; published by The American Society of Hematology.

Connolly, D., et al., "Human Vascular Permeability Factor," *J. Biol. Chem.*, vol. 264, pp. 20017-20024, 1989, published by The American Society for Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by The American Society for Clinical Investigation, Inc., Stanford University Libraries' High Wire Press, California, United States of America.

Cross, A. E. et al., "The inhibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

Dalton, et al., "Multiple Myeloma," *Hematology*, Am. Soc. Hematol. Educ. Program, 2001, pp. 157-77.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Dermer, G. B., "Another Anniversary for the War on Cancer," *Biotechnology*, 1994, vol. 12, p. 320.

Devries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries' High Wire Press, California, United States of America.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

European Search Report dated Feb. 28, 2006 for EP 05017665.0.

Ferrara, N., et al., "The Biology of Vascular Endothelial Growth Factor," *Endocrinol. Rev.*, vol. 18, No. 1, pp. 4-25, 1997, published by the Endocrine Society, Stanford University Libraries' High Wire Press, California, United States of America.

Flückiger-Isler, R. E. et al., "Stimulation of rat liver glycogen synthesis by the adenosine kinase inhibitor 5-iodotubercidin," *Biochem. J.*, vol. 292, pp. 85-91, 1993; (printed in Great Britain).

Folkman, J., "Fighting Cancer by Attacking its Blood Supply," *Scientific American*, vol. 275, pp. 150-154, Sep. 1996, published by Scientific American, Inc., New York, New York, United States of America.

Freshney, R. I., *Culture of Animal Cells—A Manual of Basic Technique*, 1983, pp. 1-4; published by Alan R. Liss, Inc.

Gontero, European Urology, 2004, vol. 46, pp. 296-311.

Grand, et al., "Targeting FGFR3 in Multiple Myeloma: Inhibition of t(4;14) Positive Cells by SU5402 and PD173074," *Leukemia*, 2004, vol. 18, pp. 962-966.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

Gura, T., "Systems for Identifying New Drugs Are Often Faulty," *Science*, 1997, vol. 278, pp. 1041-1042.

Hammond, W. P. et al., "Lithium Therapy of Canine Cyclic Hematopoiesis," *Blood*, vol. 55, No. 1, pp. 26-28, Jan. 1980.

Heinrich, M. C. et al., "Inhibition of KIT Tyrosine Kinase Activity: A Novel Molecular Approach to the Treatment of KIT-Positive Malignancies," *J. Clin. Oncol.*, vol. 20, No. 6, pp. 1692-1703, Mar. 15, 2002.

Heise, et al., "In vivo Preclinical Evaluation of Tyrosine Kinase Inhibitors with Potent Effects on Tumor Angiogenesis, Growth and Metastasis," Abstract and presentation material for a presentation at the American Association for Cancer Research meeting held in Apr. 2002.

Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.

Hirao, A. et al., "DNA Damage-Induced Activation of p53 by the Checkpoint Kinase CHk2," *Science*, vol. 287, pp. 1824-1827, Mar. 10, 2000.

Hussong, J. W. et al., "Evidence of increased angiogenesis in acute myeloid leukemia," *Blood*, 2000, vol. 95(1), pp. 309-313; The American Society of Hematology.

International Search Report for PCT/US04/36956 dated Oct. 2, 2006.
International Search Report for PCT/US2005/005316 dated Nov. 28, 2005.

Kerbel, R. S., "Tumor Angiogenesis: Past, Present and Near Future," *Carcinogenesis*, 2000, vol. 21(3), pp. 505-515; Oxford University Press.

Kirstein, CA 145:201781, abstract only of Recent Patents on Anti-cancer Drug Discovery, 2006, vol. 1(2), pp. 153-161.

Klein, P. S. et al., "A molecular mechanism for the effect of lithium on development," *Proc. Natl. Acad. Sci. USA*, vol. 93, pp. 8455-8459, Aug. 1996.

Lee, J. et al., "Positive Regulation of Wee1 by Chk1 and 14-3-3 Proteins," *Molecular Biology of the Cell*, vol. 12, pp. 551-563, Mar. 2001; published by The American Society for Cell Biology.

Lee, S. H. et al., "In vivo Target Modulation and Biological Activity of CHIR-258, a Multitargeted Growth Factor Receptor Kinase Inhibitor, in Colon Cancer Models," *Clin. Cancer Res.*, May 15, 2005, vol. 11, No. 10; pp. 3633-3641.

Leung, D., et al., "Vascular Endothelial Growth Factor Is a Secreted Angiogenic Mitogen," *Science*, vol. 246, pp. 1306-1309, Dec. 8, 1989, published by The American Society for the Advancement of Science, Stanford University Libraries' High Wire Press, California, United States of America.

Levis, M. et al., "A FLT3-targeted tyrosine kinase inhibitor is cytotoxic to leukemia cells in vitro and in vivo," *Blood*, vol. 99, No. 11, pp. 3885-3891, Jun. 1, 2002; published by The American Society of Hematology.

List of compounds purchased from various vendors (3 pages).

Liu, Q. et al., "Chk1 is an essential kinase that is regulated by Atr and required for the $G_2$/M DNA damage checkpoint," *Genes & Development*, vol. 14, 2000, pp. 1448-1459; published by Cold Springs Harbor Laboratory Press.

Lopes De Menezes, D. E. et al., "CHIR-258: A Potent Inhibitor of FLT3 Kinase in Experimental Tumor Xenograft Models of Human Acute Myelogenous Leukemia," *Clin. Cancer Res.*, Jul. 15, 2005, vol. 11, No. 14, pp. 5281-5291.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 4, pp. 1077-1086, Dec. 1, 1994; published by Elsevier Science Ltd.

Lundberg, L. G. et al., "Bone Marrow in Polycythemia Vera, Chronic Myelocytic Leukemia and Myelofibrosis Has an Increased Vascularity," *American Journal of Pathology*, 2000, vol. 157(1), pp. 15-19.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et al., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.

Massillon, D. et al., "Identification of the glycogenic compound 5-iodotubercidin as a general protein kinase inhibitor," *Biochem. J.*, vol. 299, pp. 123-128, 1994; printed in Great Britain.

Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.

McMahon, G., "VEGF Receptor Signaling in Tumor Angiogenesis," *The Oncologist 2000*, vol. 5 (suppl. 1), pp. 3-10 (2000).

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Millauer, B. et al., "Glioblastoma growth inhibited in vivo by a dominant-negative.Flk-1 mutant," *Nature*, vol. 367, pp. 576-579 (1994); published by Nature Publishing Group.

MSNBC News Services, "Mixed results on new cancer drug," Nov. 9, 2000.

Mustonen, T., et al., "Endothelial Receptor Tyrosine Kinases Involved in Angiogenesis," *J. Cell Biology*, vol. 129, No. 4, pp.

895-898, May 1995, published by The Rockefeller University Press, New York, New York, United States of America.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer Disease Brain," *Journal of Neuropathology and Experimental Neurology*, vol. 56, No. 1, pp. 70-78, Jan. 1997; published by the American Association of Neuropathologists.

Peng, C.-Y. et al., "Mitotic and G2 Checkpoint Control: Regulation of 14-3-3 Protein Binding by Phosphorylation of Cdc25C on Serine-216," *Science*, vol. 277, pp. 1501-1505, Sep. 5, 1997.

Pinedo, H. M. et al., "Translational Research: The Role of VEGF in Tumor Angiogenesis," *The Oncologist 2000*, vol. 5 (suppl. 1), pp. 1-2 (2000).

Plouet, J., et al., "Isolation and characterization of a newly identified endothelial cell mitogen produced by AtT-20 cells," *EMBO J.*, vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," *Proc. Natl. Acad. Sci. USA*, vol. 90, pp. 7533-7537, Aug. 1993.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Salmon, S. E. et al., *Basic & Clinical Pharmacology*, Seventh Edition, edited by B. Katzung, Appleton & Lange, pp. 29, 881-884 (1998).

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Shibuya, M., et al., "Nucleotide sequence and expression of a novel human receptor-type tyrosine kinase gene (flt) closely related to the fms family," *Oncogene*, vol. 5, pp. 519-524, 1990, published by Macmillan Press Ltd., Stockton Press Company, Great Britain.

Smolich, B.D. et al., "The antiangiogenic protein kinase inhibitors SU5416 and SU6668 inhibit the SCF receptor (c-kit) in a human myeloid leukemia cell line and in acute myeloid leukemia blasts," *Blood*, vol. 97, No. 5, pp. 1413-1421, Mar. 1, 2001; published by The American Society of Hematology.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Stover, D. R., "Recent advances in protein kinase inhibition: Current molecular scaffolds used for inhibitor synthesis," *Current Opinion in Drug Discovery & Development*, vol. 2, No. 4, pp. 274-285, 1999; published by PharmaPress Ltd., London, United Kingdom.

Sun, T-Q. et al.. "PAR-1 is a Dishevelled-associated kinase and a positive regulator of Wnt signalling," *Nature Cell Biology*, vol. 3, pp. 628-636, Jul. 2001; published by Macmillan Magazines Ltd.

Takashima, A. et al., "Presenilin 1 associates with glycogen synthase kinase-3β and its substrate tau," *Proc. Natl. Acad. Sci. USA*, vol. 95, pp. 9637-9641, Aug. 1998; published by the National Academy of Sciences.

Takashima, A. et al., "Tau protein kinase I is essential for amyloid β-protein-induced neurotoxicity," *Proc. Natl. Acad. Sci. USA*, vol. 90, pp. 7789-7793, Aug. 1993.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Thomas, M.D., R. J. et al., "Progress in Geriatrics: Excitatory Amino Acids in Health and Disease," *J. of the American Geriatrics Society*, vol. 43, No. 11, Nov. 1995; published by American Geriatrics Society.

Trudel, S. et al., "CHIR-258, a novel, multitargeted tyrosine kinase inhibitor for the potential treatment of t(4;14) multiple myeloma," *Blood*, Apr. 1, 2005, vol. 105, No. 7, pp. 2941-2948.

Ukrainets, I., "Effective Synthesis of 3-(Benzimidazol-2-yl)-4-Hydroxy-2-Oxo-1,2-Dihydroquinolines," *Tet. Lett.*, vol. 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3.*Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.

Ukrainets, I., et al., "4-Hydroxy-2-Quinolones 7.* Synthesis and Biological Properties of 1-R-3-(2-Benzimidazolyl)-4-Hydroxy-2-Quinolones," pp. 92-94, translated from *Khimiya Geterotsiklicheskikh Soedinii*, No. 1, pp. 105-108, Jan. 1993, published by Plenum Publ. Corp., London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

Van Der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Vogelstein, B. et al., "Surfing the p53 network," *Nature*, vol. 408, pp. 307-310, Nov. 16, 2000; published by Macmillan Magazines Ltd.

Wedge, S. R. et al., "ZD6474 Inhibits Vascular Endothelial Growth Factor Signaling Angiogenesis, and Tumor Growth following Oral Administration," *Cancer Research*, vol. 62, pp. 4645-4655, Aug. 15, 2002.

Welsh, G. I. et al., "Glycogen synthase kinase-3 is rapidly inactivated in response to insulin and phosphorylates eukaryotic initiation factor eIF-2B," *Biochem. J.*, vol. 294, pp. 625-629, 1993; printed in Great Britain.

Yamasaki, Y. et al., "Pioǵlitazone (AD-4833) Ameliorates Insulin Resistance in Patients with NIDDM," *Tohoku J. Exp. Med.*, vol. 183, pp. 173-183, 1997.

Yoo, et al., "Synchronous Elevation of Soluble Intercellular Adhesion Molecule-1 (ICAM-1) and Vascular Cell Adhesion Molecule-1 (VCAM-1) Correlates with Gastric Cancer Progression," *Yonsei Medical Journal*, vol. 39, No. 1, pp. 27-36, 1998.

Zetter, B. R., "Angiogenesis and Tumor Metastasis," *Annu. Rev. Med.*, 1998, vol. 49, pp. 407-24; published by Annual Review Inc.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

Antonios-McCrea, W. R. et al., "LHMDS mediated tandem acylation-cyclization of 2-aminobenzenecarbonitriles with 2-benzymidazol-2-yl acetates: a short and efficient route to the synthesis of 4-amino-3-benzimidazol-2-ylhydroquinolin-2-ones," *Tetrahedron Letters*, vol. 47, 2006, pp. 657-660; published by Elsevier Ltd.

Beck, J. R., "A Direct Synthesis of Benzo[b]thiophene-2-carboxylate Esters Involving Nitro Displacement," *J. Org. Chem.*, vol. 37, No. 21, 1972, pp. 3224-3226.

Berwanger, B. et al., "Loss of a *FYN*-regulated differentiation and growth arrest pathway in advanced stage neuroblastoma," *Cancer Cell*, vol. 2, Nov. 2002, pp. 377-386; published by Cell Press.

Caira, Mino R., "Crystalline polymorphism of Organic Compounds," *Topics in Current Chemistry*, vol. 198, Springer Verlag 1998.

Carling, R. W. et al., "4-Substituted-3-phenylquinolin-2(1*H*)-ones: Acidic and Nonacidic Glycine Site *N*-Methyl-D-aspartate Antagonists with in Vivo Activity," *J. Med. Chem.*, vol. 40, 1997, pp. 754-765; published by American Chemical Society.

Carmeliet, P. et al., "Angiogenesis in Cancer and Other Diseases," *Nature*, 407, pp. 249-257 (2000).

Cecil, Textbook of Medicine, 21st Edition (2000), Goldman & Bennett (Editors), W.B. Saunders Company (Publisher), Chapter 198, pp. 1060-1074).

Charvát, T. et al., "Diethyl Acetonedicarboxylate—a Precursor for the Synthesis of New Substituted 4-Aminoquinolines and Fused 4-Aminopyridines," *Monatshefte für Chemie*, vol. 126, 1995, pp. 333-340.

Danish Search Report for Singapore Patent Application No. 200501676-1 dated Feb. 28, 2006.

Danish Written Opinion for Singapore Patent Application No. 200501676-1 dated Sep. 20, 2007.

European Communication for EP 01973722.0 dated Mar. 16, 2004.

European Communication for EP 03746614.1 dated Nov. 6, 2007.

European Partial Search Report for EP 07011978 dated Sep. 19, 2007.

European Supplementary Search Report for EP 03746614.1 dated May 24, 2007.

Gewald, K. et al., "4-Amino-3-pyridiniochinolin-2(1*H*)-on-chloride and 3,4-Diaminochinolin-2(1*H*)-one," *Chem. Ber.*, vol. 124, 1991, pp. 1237-1241, Eng. Abstract provided; published by VCH Verlagsgesellschaft mbH.

Hiyama, T. et al., "A New Synthesis of 3-Amino-2-Alkenoates," *Tetrahedron Letters*, vol. 23, No. 15, 1982, pp. 1597-1600; published by Pergamon Press Ltd.

International Search Report for PCT/US00/13420 dated Aug. 14, 2000.

International Search Report for PCT/US01/42131 dated Mar. 6, 2002.

International Preliminary Examination Report for PCT/US03/10463 dated Jun. 8, 2004.

International Search Report for PCT/US03/10463 dated Jun. 12, 2003.

International Search Report for PCT/US06/19349 dated Sep. 11, 2006.

International Search Report for PCT/US2006/020296 dated Nov. 14, 2006.

Johnson et al., "Relationships between drug activity in NCI preclinical in vitro and in vivo models and early clinical trials," *British Journal of Cancer*, vol. 84, No. 10, 2001, pp. 1424-1431.

Kreimeyer, A. et al., "Evaluation and Biological Properties of Reactive Ligands for the Mapping of the Glycine Site on the *N*-Methyl-D-aspartate (NMDA) Receptor," *J. Med. Chem.*, vol. 42, 1999, pp. 4394-4404; published by American Chemical Society.

Majolini, M. B. et al., "Dysregulation of the Protein Tyrosine Kinase LCK in Lymphoproliferative Disorders and in Other Neoplasias," *Leukemia and Lymphoma*, vol. 35(3-4),1999, pp. 245-254; published by OPA (Overseas Publishers Association) N.V.

Mundy, "Preclinical models of bone metastases," *Semin. Oncol.*, 28(4 Suppl. 11), 2001, pp. 2-8.

Parham, W. E. et al., "Elaboration of Bromoarylnitriles," *J. Org. Chem.*, vol. 41, No. 7, 1976, pp. 1187-1191.

Schäfer, H. et al., "Zur Synthese von 4-Aminochinolinen und— chinolinonen-(2) aus Anthranilsäurenitril," *Journal f. prakt. Chemie*, Band 321, Heft 4, 1979, pp. 695-698, Eng. Abstract included.

Siemeister, G. et al., "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway," *Cancer Research*, vol. 59, Jul. 1, 1999, pp. 3185-3191.

Suggitt et al., "50 Years of Preclinical Anticancer Drug Screening: Empirical to Target-Driven Approaches," *Clinical Cancer Research*, vol. 11, 2005, pp. 971-981.

Valtola, R. et al., "VEGFR-3 and its Ligand VEGF-C Are Associated with Angiogenesis in Breast Cancer," *American Journal of Pathology*, vol. 154, No. 5, May 1999, pp. 1381-1390; published by American Society for Investigative Pathology.

Veronese, A. C. et al., "Tin(IV) Choloride-promoted vs. Metal β-Carbonyl-enolate-catalysed Reactions of β-Dicarbonyls with Nitriles," *J. Chem Research (S)*, 1988, pp. 246-247.

Veronese, A. C. et al., "Tin (IV) Chloride-promoted Synthesis of 4-Aminopyridines and 4-Aminoquinolines," *Tetrahedron*, vol. 51, No. 45, 1995, pp. 12277-12284; published by Elsevier Science Ltd.

Winstead, E., "p53 Gene May Help Fight Tumors," *NCI Cancer Bulletin*, vol. 4, No. 5, pp. 1-2, 2007.

Yao et al., "Cell-specific but p53-independent Regulation of Vascular Endothelial Growth Factor Expression by Interferons in Human Glioblastoma Cells," *Journal of Neuro-Oncology*, vol. 76, pp. 219-225, 2006.

Zeng et al., "HDAC3 is crucial in shear- and VEGF-induced stem cell differentiation toward endothelial cells," *The Journal of Cell Biology*, vol. 174, No. 7, pp. 1059-1069, 2006.

Berge, et. al., Pharmaceutical Salts, *J. Pharm. Sci*, vol. 66, No. 1, pp. 1-19., 1977.

Guideline for the Format and Content of the Human Pharmacokinetic and Bioavailability Section of an Application, Center for Drugs and Biologics, FDA, Department of Health and Human Services, pp. 1-18, Feb. 1997.

Foekens et al. Cancer Research, vol. 61, pp. 5407-5414, 2001.

Susa, M. et al., "Src inhibitors: drugs for the treatment of osteoporosis, cancer or both?," TiPS, vol. 21, Dec. 2000, pp. 489-495; published by Elsevier Science Ltd.

Timmer et al.; Lithium Intoxication; J. Am. Soc. Nephro.; vol. 10, pp. 666-674; 1999.

U.S. Notice of Allowance in U.S. Appl. No. 10/886,950 mailed Jun. 12, 2009.

Andre, T., et al., "CPT-11 (Irinotecan) Addition to Bimonthly, High-dose Leucovorin and Bolus and Continuous-infusion 5-Fluorouracil (FOLFIRI) for Pretreated Metastic Colorectal Cancer," European Journal of Cancer, vol. 35, No. 9, 1999, pp. 1343-1347. Compound summary also attached.

Glade-Bender, J., et al., "VEGF blocking therapy in the treatment of cancer," Expert Opinion on Biological Therapy, vol. 3, No. 2, Apr. 2003, pp. 263-276.

Jackman A.L., et al., "Combination of Raltitrexed with other Cytotoxic Agents: Rationale and Preclinical Observations," European Journal of Cancer, vol. 35, Suppl. 1, Mar. 1999, pp. S3-S8. Compound summary also attached.

Magne, N., et al., "Sequence-dependent effects of ZD 1839 (Iressa) in combination with cytotoxic treatment in human head and neck cancer," British Journal of Cancer, 2002, pp. 819-827.

Morin, M. J., "From oncogene to drug: development of small molecule tyrosine kinase inhibitors as anti-tumor and anti-angiogenic agents," Oncogene, 2000, pp. 6574-6583.

Noble, M. et al., "Protein Kinase Inhibitors: Insights into Drug Design from Structure," Science, vol. 303, Mar. 19, 2004, pp. 1800-1805.

Bulusu V. R., "Irinotecan and 5-Flourouracil in Colorectal Cancer: Time for a Pause?," European Journal of Cancer, vol. 34, No. 3, 1998, pp. 286-289.

European Search Report received for EP Appln. No. 03783281.3 mailed Jan. 15, 2010.

European Search Report received for EP Appln. No. 04816941.1 mailed Jan. 14, 2010.

Supplementary Search Report received in Malaysian Appln. No. PI20034345 completed Jan. 14, 2010.

Chekhun (Tschechun), et al., "Current View on the Mechanisms of Drug Resistance of Tumors," Onkologijya, 2000, T.2, No. 1-2, pp. 11-15. (English Summary: p. 15.).

Baltensperger, et al., "Catalysis of serine and tyrosine autophorylation by the human insulin receptor," Proc. Nat'l. Acad. Sci. USA, vol. 89, Sep. 1992, pp. 7885-7889.

Blakey et al., "Anti-cancer drug discovery and development summit," Expert Opin. Investig. Drugs, vol. 12, No. 9, Sep. 2003, pp. 1577-1582.

Klein et al., "Combined Tyrosine and Serine/Threonine Kinase Inhibition by Sorafenib Prevents Progression of Experimental Pulmonary Hypertension and Myocardial Remodeling," Circulation, Nov. 11, 2008, vol. 118, No. 20, pp. 2081-2090.

Notice of Allowance received for U.S. Appl. No. 10/706,328 dated Jun. 11, 2010.

Notice of Allowance received for U.S. Appl. No. 11/061,386 dated Jul. 19, 2010.

Notice of Allowance received on U.S. Appl. No. 10/983,174 dated Jul. 8, 2010.

Supplementary European Search Report received for European Appln. No. 04810468.1 dated May 25, 2010 and mailed Jun. 1, 2010.

Bosserhoff, "Elevated MIA Serum Levels are of Relevance for Management of Metastasized Malignant Melanomas: Results of a German Multicenter Study," Journal of Invest. Derm., vol. 114, No. 2, Feb. 1, 2000, pp. 395-396.

International Search Report and Written Opinion received for PCT/US2008/056122 mailed Jul. 4, 2008.

Khristich, et al., "Tautomerism in a Number of Asymmetrical Imdazole Systems," UDC 547.78:541.623, Chemistry of Heterocyclic Compounds, vol. 6, No. 12, Dec. 1970, pp. 1572-1575.

Kim, "Study Summary: A Phase I/II Dose Escalating Study to Evaluate the Safety, Pharamacokinetics and Pharmacodynamics and Efficacy of TKI258 in Patients with Locally Advanced or Metastic Melanoma," Study Summary No. 2005-838, Melanoma Medical Oncology Dept., MD Anderson Cancer Center, May 4, 2006, 4 pages.

McArthur, et al., "Cytokines/immunobiology immunotherapy," Poster Presentation, European Journal of Cancer, Supplement, vol. 3, No. 2, Oct. 1, 2005, 1 page.

Oshimi, "Trend of Blood Tumor Clinical Study," Japan Pharmacol. Ther., 2001, Vo. 29, No. 3, pp. 169-173.

Second Written Opinion received for Singapore Appln. No. 200603047-2 completed Oct. 25, 2010.

Alaimo, et al., "Targeting the gatekeeper residue in phosphoinositide 3-kinases" Bioorganic & Medicinal Chemistry, 2005, vol. 13, pp. 2825-2836.

Grand, et al., "Targeting FGFR3 in Multiple Myeloma: The use of SU5402 and PD173074 to Inhibit T Positive Cells," British Journal of Haematology, vol. 121, Suppl. 1, May 1, 2003, p. 89 (Whole supplement included, pp. 87-95).

Lee, Sang Hoon et al., "Pharmacological Activities of CHIR258, a Small Molecule Inhibitor of Growth Factor Tyrosine Kinase Receptors Involved in Angiogenesis and Tumor Cell Proliferation," Proceedings of the American Association for Cancer Research 94th Annual Meeting, vol. 44, Jul. 2003, p. 934.

Supplementary European Search Report received for European Appln. No. 04810419.4 completed Sep. 1, 2010.

Wiesmann, et al., "In Vitro Characterization of a Potent Tyrosine Kinase Inhibitor, CHIR258, that Modulates Angiogenesis and Proliferation of selected Cancer Cell Lines," Proceedings of the American Association for Cancer Research, 94th Annual Meeting, vol. 44, Jul. 3003, p. 934.

Aranda-Anzaldo, et al., "Developmental noise, ageing and cancer," Mechanisms of Ageing and Development 124, 2003, pp. 711-720.

Search and Examination Report received for Singapore Appln. No. 200603047-2 mailed Sep. 15, 2011.

Clinical Science, 1993 vol. 29, No. 9, pp. 1149-1154. (No English translation available.).

Dictionary of Biochemistry (The Third Edition), Kabuskiki Gaisha Tokyo Kagaku Dojin, Jul. 1, 2002, 2 pages. (No English translation available.).

Kovacs, et al., "A phase II study of ZD6474 (Zactima), a selective inhibitor of VEGFR and EGFR tyrosine kinase in patients with relapsed multiple myeloma-NCIC CTG IND. 145," Investigational New Drugs, 2006, vol. 24, No. 6, pp. 529-535.

Prince, et al., "Vascular endothelial growth factor inhibition is not an effective therapeutic strategy for relapsed or refractory multiple myeloma: a phase E2 study of pazopanib (GW786034)," Blood, 2009, vol. 113, No. 19, p. 4819-4820.

Zangari, M. et al., "Phase II study of SU5416, a small molecule vascular endothelial growth factor tyrosine kinase receptor inhibitor, in patients with refractory multiple myeloma," Clinical Cancer Research, 2004, vol. 10, No. 1, Pt. 1, pp. 88-95.

\* cited by examiner

Real Time Monitoring in vivo KMS-11-luc MM Growth in SCID-beige Mice Treated with Vehicle or Compound 1 (20 mg/kg, p.o. daily)

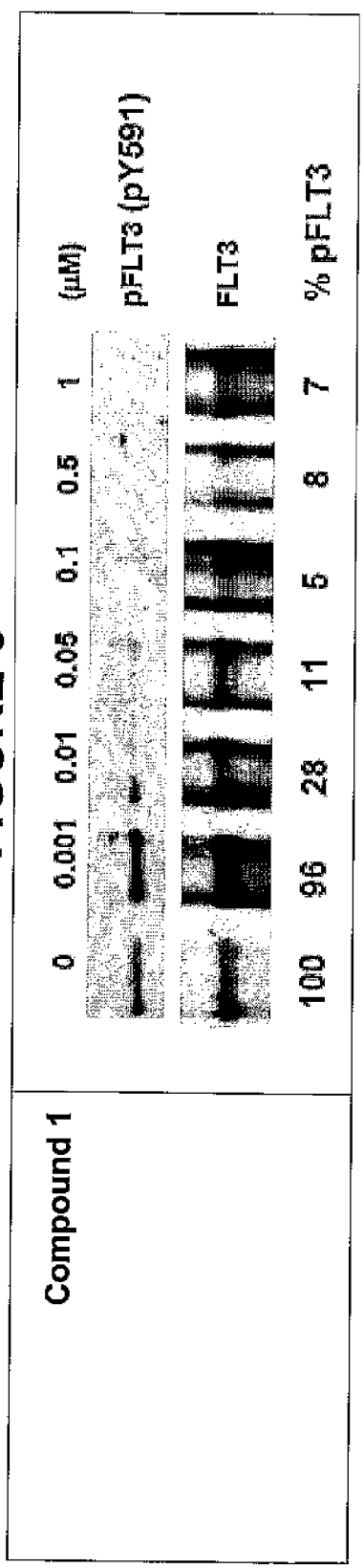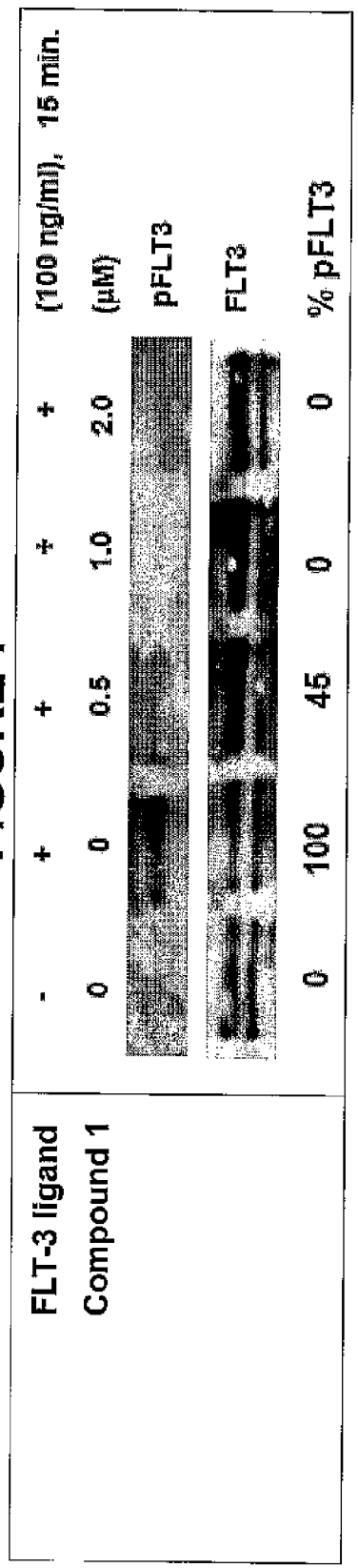

FIGURE 25
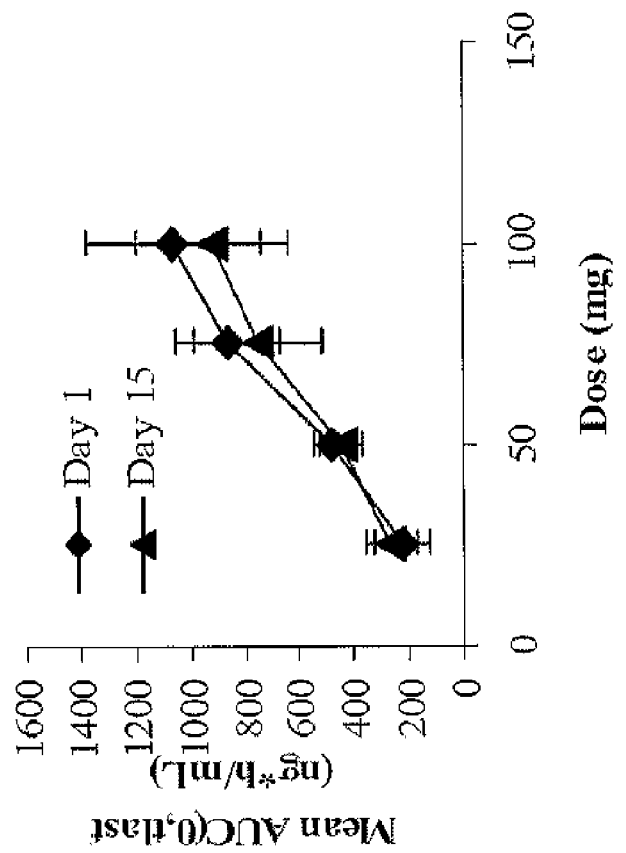
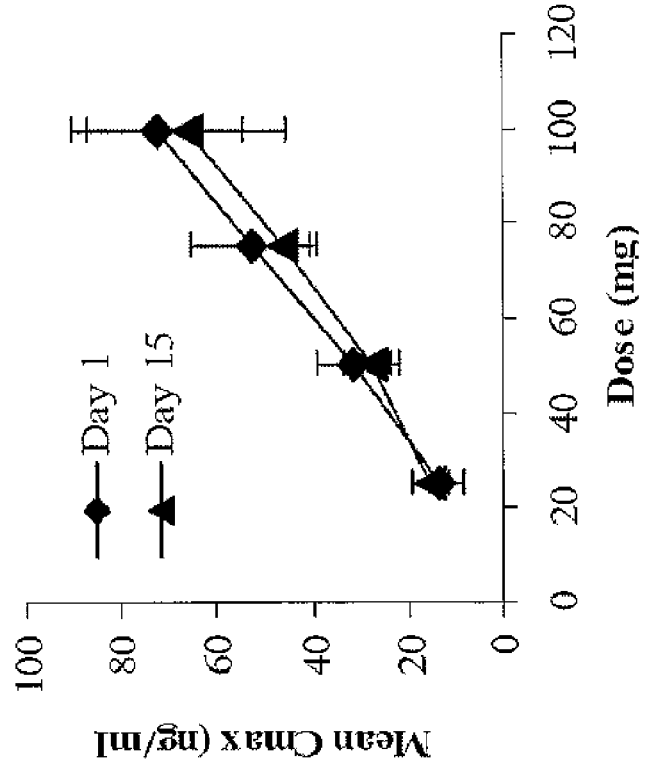

4-Amino-5-fluoro-3-[6-(4-methylpiperazin-1-yl)-1H-benzimidazol-2-yl]quinolin-2(1H)-one Dosed Days 1-7, Off Days 8-14, Dosed Days 15-21, etc.

- Strong inhibition of pERK detectable Day 1, 4 hr
- Inhibition maintained on Day 7, 4 and 24 hr
- Day 15; inhibition at 4 and 24 hr after dose

METHODS FOR TREATING DRUG RESISTANT CANCER

CROSS REFERENCE TO RELATED APPLICATIONS

This application claims priority to International Application PCT/US2006/017922, filed May 10, 2006, which in turn claims priority to U.S. Provisional Application No. 60/680,722 filed May 13, 2005, the entire contents of each of which are incorporated by reference herein and for all purposes.

FIELD OF THE INVENTION

This invention pertains generally to methods of treating cancer. More specifically, the invention pertains to methods and 4-amino substituted quinolinone benzimidazolyl compounds such as 4-amino-5-fluoro-3-[5-(4-methylpiperazin-1-yl)-1H-benzimidazol-2-yl]quinolin-2(1H)-one compounds and pharmaceutical formulations comprising such compounds for treating drug-resistant cancer and patients with drug resistant cancer.

BACKGROUND OF THE INVENTION

A variety of chemical compounds and compositions have been reported as having activity against one or more vascular endothelial growth factor receptor tyrosine kinase (VEGF-RTK). Examples include quinoline derivatives such as described in WO 98/13350, aminonicotinamide derivatives (see, e.g. WO 01/55114), antisense compounds (see, e.g. WO 01/52904), peptidomimetics (see, e.g. WO 01/52875), quinazoline derivatives (see, e.g. U.S. Pat. No. 6,258,951) monoclonal antibodies (see, e.g. EP 1 086 705 A1), various 5,10,15,20-tetraaryl-porphyrins and 5,10,15-triaryl-corroles (see, e.g. WO 00/27379), heterocyclic alkanesulfonic and alkane carboxylic acid derivatives (see, e.g. DE19841985), oxindolylquinazoline derivatives (see, e.g. WO 99/10349), 1,4-diazaanthracine derivatives (see, e.g. U.S. Pat. No. 5,763,441), and cinnoline derivatives (see, e.g. WO 97/34876), and various indazole compounds (see, e.g. WO 01/02369 and WO 01/53268).

The synthesis of 4-hydroxy quinolone and 4-hydroxy quinoline derivatives is disclosed in a number of references. For example, Ukrainets et al. have disclosed the synthesis of 3-(benzimidazol-2-yl)-4-hydroxy-2-oxo-1,2-dihydroquinoline. Ukrainets, I. et al., Tetrahedron Lett. 42, 7747-7748 (1995); Ukrainets, I. et al., Khimiya Geterotsiklicheskikh Soedinii, 2, 239-241 (1992). Ukrainets has also disclosed the synthesis, anticonvulsive and antithyroid activity of other 4-hydroxy quinolones and thio analogs such as 1H-2-oxo-3-(2-benzimidazolyl)-4-hydroxyquinoline. Ukrainets, I. et al., Khimiya Geterotsiklicheskikh Soedinii, 1, 105-108 (1993); Ukrainets, I. et al., Khimiya Geterotsiklicheskikh Soedinii, 8, 1105-1108 (1993); Ukrainets, I. et al., Chem. Heterocyclic Comp. 33, 600-604, (1997).

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinoline is substituted with a sulfur group are disclosed in WO 92/18483. These compounds are disclosed as being useful in pharmaceutical formulations and as medicaments.

Quinolone and coumarin derivatives have been disclosed as having use in a variety of applications unrelated to medicine and pharmaceutical formulations. References that describe the preparation of quinolone derivatives for use in photopolymerizable compositions or for luminescent properties include: U.S. Pat. No. 5,801,212 issued to Okamoto et al.; JP 8-29973; JP 7-43896; JP 6-9952; JP 63-258903; EP 797376; and DE 23 63 459.

A plethora of substituted quinolinone compounds including quinolinone benzimidazolyl compounds and 4-amino substituted quinolinone benzimidazolyl compounds such as 4-amino-5-fluoro-3-[5-(4-methylpiperazin-1-yl)-1H-benzimidazol-2-yl]quinolin-2(1H)-one have recently been disclosed in references such as WO 02/22598 and WO 2004/043389. Such compounds are disclosed as inhibiting VEGF-RTKs. Such compounds are also disclosed in published United States patent applications U.S. 2002/0107392 and U.S. 2003/0028018 and U.S. Pat. Nos. 6,605,617, 6,774,237, and 6,762,194. Heterocyclic compounds related to benzimidazolyl quinolinones have recently been disclosed in WO 02/18383, U.S. 2002/0103230, and U.S. Pat. No. 6,756,383. Other such compounds are disclosed along with new uses of such compounds in inhibiting serine/threonine kinases and tyrosine kinases are disclosed in WO 2004/018419, and U.S. 2004/0092535, filed on Aug. 19, 2003, and claiming priority to each of the following provisional applications: U.S. Provisional Application No. 60/405,729 filed on Aug. 23, 2002; U.S. Provisional Application No. 60/426,107 filed on Nov. 13, 2002; U.S. Provisional Application No. 60/426,226 filed on Nov. 13, 2002; U.S. Provisional Application No. 60/426,282 filed on Nov. 13, 2002; U.S. Provisional Application No. 60/428,210 filed on Nov. 21, 2002; U.S. Provisional Application No. 60/460,327 filed on Apr. 3, 2003; U.S. Provisional Application No. filed on Apr. 3, 2003; U.S. Provisional Application No. 60/460,493 filed on Apr. 3, 2003; U.S. Provisional Application No. 60/478,916 filed on Jun. 16, 2003; and U.S. Provisional Application No. 60/484,048 filed on Jul. 1, 2003. Still other compounds, method for their synthesis, lactic acid salts thereof, and uses thereof are disclosed in the following patent applications filed on Nov. 5, 2004: U.S. patent application Ser. No. 10/983,174; U.S. patent application Ser. Nos. 10/982,757; and 10/982,5423. Each of the documents in this paragraph is hereby incorporated by reference in its entirety and for all purposes as if fully set forth herein.

Various new compounds have recently been found useful in treating cancer. For example, Gleevec® (imatinib mesylate) is a compound that has recently shown significant activity in a number of different cancers. Gleevec was first made available to patients with Chronic Myeloid Leukemia (CML) in May of 2001. According to the Novartis website, Gleevec is indicated for the treatment of newly diagnosed adult patients with Philadelphia chromosome-positive (Ph+) CML in chronic phase. Follow-up is limited. Gleevec is also indicated for the treatment of patients with pH+ CML in blast crisis, accelerated phase, or in chronic phase after failure of interferon-alpha therapy. Gleevec is also indicated for the treatment of pediatric patients with pH+ chronic phase CML whose disease has recurred after stem cell transplant or who are resistant to interferon-alpha therapy. Gleevec has been approved for use in patients with other cancers such as Gastrointestinal Stromal Tumors (GIST). For example, on Feb. 1, 2002, the FDA granted Novartis approval of Gleevec for the treatment of patients with KIT (CD117) positive unresectable and/or metastatic malignant GIST.

Other new experimental drugs that are currently being tested for efficacy in treating cancer include BAY43-9006 (sorafenib) and Brostallicin. BAY 43-9006 has been granted orphan drug status for the treatment of renal cell carcinoma by the U.S. Food and Drug Administration (FDA). BAY 43-9006 is being evaluated for the treatment of metastatic renal cell carcinoma, an advanced form of kidney cancer. A similar designation has been granted in the European Union by the Committee for Orphan Medicinal Products (COMP) of the European Medicines Agency (EMEA). BAY 43-9006 is a novel RAF kinase and VEGFR inhibitor that is intended to prevent tumor growth by combining two anticancer activities: inhibition of tumor cell proliferation and tumor angiogenesis. Brostallicin (PNU-166196) is a synthetic α-bromoacrylic, second-generation DNA minor groove binder structurally related to distamycin A, presently in Phase II trials in Europe and the United States. The compound shows broad antitumor activity in preclinical models and dramatically reduced in vitro myelotoxicity in human hematopoietic progenitor cells compared with that of other minor groove binders. Brostallicin showed a 3-fold higher activity in melphalan-resistant L1210 murine leukemia cells than in the parental line ($IC_{50}$=0.46 and 1.45 ng/mL, respectively) under conditions in which the cytotoxicity of conventional antitumor agents was either unaffected or reduced.

Although significant strides have been made in the development of pharmaceutical compositions for treating cancer, new methods of treating cancer are required. Especially needed are pharmaceutical compositions and compounds for use in preparing pharmaceutical compositions that are useful in treating drug-resistant cancer and patients with drug-resistant cancers. Also needed are pharmaceutical compositions and compounds that may be administered to patients with drug-resistant cancers in conjunction with known anti-cancer agents.

SUMMARY OF THE INVENTION

The present invention provides methods of treating cancer, methods of treating drug-resistant cancer, and kits and therapeutic compositions for use in treating cancer in subjects such as those with drug-resistant cancer.

In one aspect, the present invention provides a method for treating drug-resistant cancer. The method includes administering to a subject in need thereof, a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture. In some embodiments, the subject is a cancer patient with drug-resistant cancer. The compound of formula I has the following formula:

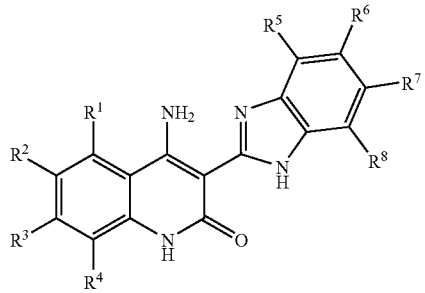

I wherein:

$R^1$, $R^2$, $R^3$, and $R^4$ may be the same or different and are independently selected from H, Cl, Br, F, I, —$OR^{10}$ groups, —$NR^{11}R^{12}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, or substituted or unsubstituted heterocyclylalkyl groups;

$R^5$, $R^6$, $R^7$, and $R^8$ may be the same or different and are independently selected from H, Cl, Br, F, I, —$OR^{13}$ groups, —$NR^{14}R^{15}$ groups, —$SR^{16}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

$R^{10}$ and $R^{13}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

$R^{11}$ and $R^{14}$ may be the same or different and are independently selected from substituted or unsubstituted alkyl groups, substituted or unsubstituted aryl groups, or substituted or unsubstituted heterocyclyl groups;

$R^{12}$ and $R^{15}$ may be the same or different and are independently selected from substituted or unsubstituted alkyl groups, substituted or unsubstituted aryl groups, or substituted or unsubstituted heterocyclyl groups; and $R^{16}$ is selected from substituted or unsubstituted alkyl groups, substituted or unsubstituted aryl groups, or substituted or unsubstituted heterocyclyl groups.

In another aspect, the present invention provides a method for treating cancer. The method includes administering to a subject in need thereof, an anti-cancer drug selected from imatinib mesylate (Gleevec), BAY43-9006, Brostallicin, lenalidomide (Revlimid), thalidomide (Thalomid), docetaxel (Taxotere), erlotinib (Tarceva), vatalinib (PTK-787), VEGF-trap, fenretidine, bortezomib, bevacizumab (Avastin), pertuzumab, and/or rituximab, and a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture. The compound of formula I has the structure and variables described above.

In yet another aspect, the present invention provides kits and therapeutic compositions. The kits and therapeutic compositions include an anti-cancer drug and a compound of formula I, a tautomer of the compound, a salt of the compound, a salt of the tautomer, or a mixture thereof. The therapeutic compositions include the anti-cancer drug and the compound of formula I, the tautomer of the compound, the salt of the compound, the salt of the tautomer, or the mixture thereof as a combined preparation for simultaneous, separate, or sequential use in the treatment of a subject that has drug-resistant cancer. The compound of formula I has the structure and variables described above.

In another aspect, the present invention provides a method for inhibiting a kinase in a subject. The method includes administering to a subject in need thereof a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture. The compound of formula I has the structure and variables described above, the subject is a cancer patient, and the kinase comprises a mutant gatekeeper residue.

Further objects, features and advantages of the invention will be apparent from the following detailed description.

BRIEF DESCRIPTION OF THE DRAWINGS

FIGS. 5-7 are graphs showing that 4-amino-5-fluoro-3-[6-(4-methylpiperazin-1-yl)-1H-benzimidazol-2-yl]quinolin-2(1H)-one (Compound 1) modulates FLT3 target expression and demonstrates anti-proliferative effects against MV4;11 and RS4;11 cells.

In FIG. 5, MV4;11 (▲) or RS4;11 (in presence of FLT3 ligand) (■) were incubated with serial dilutions of Compound 1. Cell viability was determined by the MTS assay after a 72 hour incubation period. $EC_{50}$ values were calculated using nonlinear regression.

In FIG. 6, serum starved MV4;11 (ITD) or in

FIG. 7, RS4;11 (WT) cells were incubated with an increasing concentration of Compound 1 for 3 hours prior to cell lysis. RS4;11 cells were stimulated with FLT3 ligand (100 ng/ml) for 15 minutes, as indicated. Whole cell lysates were immunoprecipitated with anti-human FLT3 antibody, resolved by SDS-PAGE. Immunoblots were probed with anti-phosphotyrosine antibody (upper lane). Membranes were stripped and reprobed with anti-FLT3 to demonstrate equal loading of FLT3 (lower lane). Changes in pFLT3 are reported as percent of baseline (no treatment) using densitometry.

(FIG. 12) MV4;11 or (FIG. 13) RS4;11 cells were implanted s.c. into the right flank of SCID-NOD mice (n=10 mice/group). In MV4;11 studies, Vehicle (◇) or Compound 1 at doses of 1 (●), 5 (▲), or 30 (■) mg/kg/d for 15 days was administered orally when tumors were ~300 mm3. In RS4;11 studies, Vehicle (◇) or Compound 1 at doses of 10 (▲), 30 (■), 100 (♦) or 150 (●) mg/kg/d for 8 days was administered orally when tumors were ~300 mm3. (FIG. 14) Effect of daily, intermittent and cyclic dosage regimens of Compound 1 on the efficacy of MV4;11 tumors. Compound 1 was administered orally at a dose of 30 mg/kg either daily (■), every other day/q.o.d. (●) or cyclic 7 day on/7 days off (X). (FIG. 15) Compound 1 induces regression of large MV4;11 tumors. MV4;11s.c. tumors (n=10 mice/group) were staged at 300 (▲), 500 (■) or 1000 (●) mm3. Vehicle (♦) treated tumors were measured to a maximum tumor volume of 2000 mm3 (in FIG. 16 shown only to 1000 mm3). Compound 1 was administered orally at 30 mg/kg/d (first cycle). Dosing was discontinued after 50 days, and durability of responses were monitored thereafter. (FIG. 16) Recurring MV4;11 tumors after pretreatment with 30 mg/kg/d×50 days were re-treated with 30 mg/kg/d (second cycle). Panel AD, data are expressed as mean tumor volume±SE (n=10 mice/group), Panel E illustrates the tumor volumes of individual mice (n=10).

(FIG. 17) Early MV4; 11 tumor responses with 30 mg/kg Compound 1 treatment. SCID-NOD mice bearing s.c. MV4;11 tumors (n=3-5/group) were treated with either Vehicle (a-e) or Compound 130 mg/kg/d for 5 days (f-j). Tumors were resected on days 2-5. Paraffin-embedded tumors were either stained with Hematoxylin and Eosin (a, f-day 1) or immunostained with Ki67 (b, g-day 5), pERK (c, hday 5), cleaved caspase-3 (d, i-day 5) or PARP (e, j-day 5) (with hematoxylin counter stain). FIG. 17 illustrates representative sections from n=3 individual treated tumors. (FIG. 18) Immunohistochemistry of RS4;11 tumors following treatment with 30 mg/kg Compound 1 treatment. RS4;11 tumors (n=3-5/group) were treated with either Vehicle (a-c) or Compound 130 mg/kg/d (d-f). Tumors were resected on days 9. Paraffin-embedded tumors were either stained with Hematoxylin and Eosin (a, d) or immunostained with Ki67 (b, e), or pERK (c, D. FIG. 18 illustrates representative sections from n=3 individual treated tumors. (FIG. 19) SCID-NOD mice bearing s.c. MV4;11 tumors (n=3-5/group) were treated with either Vehicle or Compound 130 mg/kg/d. Vehicle-treated tumors were resected on day 15 and Compound 1-treated tumors were resected on day 89 (50 daily doses of Compound 1+39 days without treatment). Paraffin-embedded tumors were either stained with Hematoxylin and Eosin or immunostained with Ki67 (with hematoxylin counter stain). (a) Vehicle (H&E, day 15); (b) Vehicle (Ki67, day 15); (c) Compound 1, partial response (H&E, day 89); (d) Compound 1, partial response (Ki67, day 89) and (e) Compound 1, complete response (H&E, day 89). Arrows in c, d point to areas of viable cells dispersed in necrotic/scar tissue. FIG. 19 illustrates representative sections from n=3-5 treated tumors. Magnification of the images as taken is indicated on the Figures.

FIG. 20 illustrates Kaplan-Meier percent survival vs. time plots (n=10-12 mice/group). (FIG. 21) Flow cytometric or histopathological evaluation of BM after i.v. inoculation of MV4; 11 cells. Treatments consisted of either Vehicle (a-c) or Compound 1 20 mg/kg/d (d-f; days 23-98). Femurs were collected on day 51 (a-d) or day 167 (e, f, BM was isolated and analyzed for % human MV4;11 cells using flow cytometry (aid). BM cells were stained with either anti-human HLAA, B,C-FITC (stains epitope on human MHC-1, solid line) or isotype-control antibody (dotted line). Percent engrafted cells were identified after appropriate gating, and positive staining for anti-human HLA-A,B,C (marker). BM specimens of vehicle-treated (day 51) or Compound 1-treated (day 167) mice were histochemically stained with H&E (b, e) or immunostained with an anti-human mitochondrial antibody (c, 9 which stains human MV4;11 cells in mouse BM. Magnification 400×; arrows point to identified MV4;11 cells (b, c).

FIGS. 25a and 25b are graphs of mean $C_{max}$ (ng/mL) versus dose and mean AUC (0, tlast (ng*h/mL) showing that plasma exposure increases proportionally when Compound 1 is administered.

DETAILED DESCRIPTION OF THE INVENTION

Figure 1:
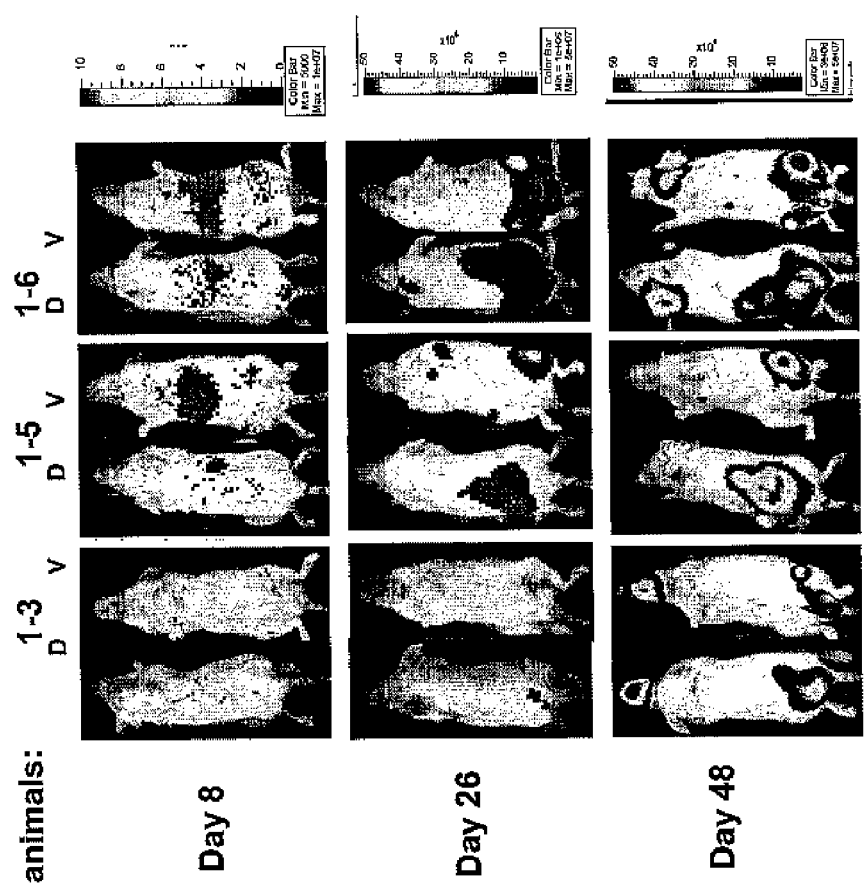
FIG. 1 is a scanned image showing whole body bioluminescent images (BLI) obtained using an IVIS Imaging System (Xenogen) of SCID-beige mice after intravenous injection with KMS-11-luc cells.

The present invention provides methods of treating cancer, methods of treating drug-resistant cancer, and kits and therapeutic compositions for use in treating cancer in subjects such as those with drug-resistant cancer. The compounds act as antagonists of receptor tyrosine kinases, and, more particularly, as inhibitors of PDGFRα and PDGFRβ, bFGF and/or VEGF-RTK function. Such compounds also have potent activity with respect to other tyrosine kinases and also with respect to various serine/threonine kinases. The compounds provided herein can be formulated into pharmaceutical formulations that are useful, for example, in treating patients with a need for an inhibitor of VEGF-RTK, especially, for use in compositions and methods for reducing capillary proliferation and in the treatment of cancer, particularly drug-resistant cancers.

The following abbreviations and definitions are used throughout this application:

"AML" is an abbreviation that stands for acute myelogenous leukemia.

"ALS" is an abbreviation that stands for amyotropic lateral sclerosis.

"AD" is an abbreviation that stands for Alzheimer Disease.

"APP" is an abbreviation that stands for amyloid precursor protein.

"ASCT" is an abbreviation that stands for autologous stem cell transplant.

"BM" is an abbreviation that stands for bone marrow.

"bFGF" is an abbreviation that stands for basic fibroblast growth factor.

"FGFR1", also referred to as bFGFR, is an abbreviation that stands for a tyrosine kinase that interacts with the fibroblast growth factor FGF.

"Cdc 2" is an abbreviation that stands for cell division cycle 2.

"Cdk 2" is an abbreviation that stands for cyclin dependent kinase 2.

"Cdk 4" is an abbreviation that stands for cyclin dependent kinase 4.

"Chk 1" is an abbreviation that stands for checkpoint kinase 1.

"CK1ϵ" is a serine/threonine kinase that stands for Casein kinase 1 (epsilon).

"c-ABL" is an abbreviation for a tyrosine kinase that stands for an oncogene product originally isolated from the Abelson leukemia virus.

"C-Kit" is also known as stem cell factor receptor or mast cell growth factor receptor.

"FGF" is an abbreviation for the fibroblast growth factor that interacts with FGFR1.

"FGFR3" is an abbreviation that stands for the tyrosine kinase fibroblast growth factor receptor 3 that is often expressed in multiple myeloma-type cancers.

"Flk-1" is an abbreviation that stands for fetal liver tyrosine kinase 1, also known as kinase-insert domain tyrosine kinase or KDR (human), also known as vascular endothelial growth factor receptor-2 or VEGFR2 (KDR (human), Flk-1 (mouse)).

"FLT-1" is an abbreviation that stands for fms-like tyrosine kinase-1, also known as vascular endothelial growth factor receptor-1 or VEGFR1.

"FLT-3" is an abbreviation that stands for fms-like tyrosine kinase-3, also known as stem cell tyrosine kinase I (STK I).

"FLT4" is an abbreviation that stands for fms-like tyrosine kinase-4, also known as VEGFR3.

"Fyn" is an abbreviation that stands for FYN oncogene kinase related to SRC, FGR, YES.

"GSK-3" is an abbreviation that stands for glycogen synthase kinase 3.

"PAR-1" is an abbreviation that stands for a kinase also known as disheveled associated kinase, also known as HDAK.

"Lck" is an abbreviation that stands for lymphocyte-specific protein tyrosine kinase.

"MEK1" is an abbreviation that stands for a serine threonine kinase in the MAPK (Mitogen activated protein kinase) signal transduction pathway in a module that is formed of the Raf-MEK1-ERK. MEK1 phosphorylates ERK (extracellular regulated kinase).

"MM" is an abbreviation that stands for multiple myeloma.

"NEK-2" is an abbreviation that stands for NIM-A related kinase.

"NIM-A" is an abbreviation that stands for never in mitosis.

"PDGF" is an abbreviation that stands for platelet derived growth factor. PDGF interacts with tyrosine kinases PDGFRα and PDGFRβ.

"Rsk2" is an abbreviation that stands for ribosomal S6 kinase 2.

"Raf" is a serine/threonine kinase in the MAPK signal transduction pathway.

"RTK" is an abbreviation that stands for receptor tyrosine kinase.

"Tie-2" is an abbreviation that stands for tyrosine kinase with Ig and EGF homology domains.

"VEGF" is an abbreviation that stands for vascular endothelial growth factor.

"VEGF-RTK" is an abbreviation that stands for vascular endothelial growth factor receptor tyrosine kinase.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$—)CH(CH$_3$)CH(CH$_3$)(CH$_2$CH$_3$), and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above, The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 4 or from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus, by way of example, the phrase includes, but is not limited to, groups such as phenyl, biphenyl, anthracenyl, and naphthyl. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. In some embodiments, unsubstituted aryl groups have from 6 to 14 carbon atoms. Unsubstituted aryl groups may be bonded to one or more carbon atom(s), oxygen atom(s), nitrogen atom(s), and/or sulfur atom(s) in the parent compound.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to groups such as tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH=C(H)(CH$_3$), —CH=C(CH$_3$)$_2$, —C(CH$_3$)=C(H)$_2$, —C(CH$_3$)—C(H)(CH$_3$), —C(CH$_2$CH$_3$)=CH$_2$, cyclohexenyl, cyclopentenyl, cyclohexadienyl, butadienyl, pentadienyl, and hexadienyl among others. In some embodiments, unsubstituted alkenyl groups have from 2 to 8 carbon atoms.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. In some embodiments, unsubstituted alkynyl groups have from 2 to 8 carbon atoms.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, N-alkyl piperazinyl groups such as 1-methyl piperazinyl, piperazine-N-oxide, N-alkyl piperazine N-oxides, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, or unsubstituted heterocyclyl group. Examples include but are not limited to 1-benzylpiperidinyl, 3-phenythiomorpholinyl, 3-(pyrrolidin-1-yl)-pyrrolidinyl, and 4-(piperidin-1-yl)-piperidinyl. Groups such as N-alkyl substituted piperazine groups such as N-methyl piperazine, substituted morpholine groups, and piperazine N-oxide groups such as piperazine N-oxide and N-alkyl piperazine N-oxides are examples of some substituted heterocyclyl groups. Groups such as substituted piperazine groups such as N-alkyl substituted piperazine groups such as N-methyl piperazine and the like, substituted morpholine groups, piperazine N-oxide groups, and N-alkyl piperazine N-oxide groups are examples of some substituted heterocyclyl groups that are especially suited as $R^6$ or $R^7$ groups.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group. Examples include but are not limited to phenyl-(piperidin-1-yl)-methyl and phenyl-(morpholin-4-yl)-methyl.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The phrase "unsubstituted aryloxyalkyl" refers to an unsubstituted alkyl group as defined above in which a carbon bond or hydrogen bond is replaced by a bond to an oxygen atom which is bonded to an unsubstituted aryl group as defined above.

The phrase "substituted aryloxyalkyl" refers to an unsubstituted aryloxyalkyl group as defined above in which a bond to a carbon or hydrogen group of the alkyl group of the aryloxyalkyl group is bonded to a non-carbon and non-hydrogen atom as described above with respect to substituted alkyl groups or in which the aryl group of the aryloxyalkyl group is a substituted aryl group as defined above.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above.

The phrase "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles. Examples include but are not limited to pyrid-2-ylmorpholin-4-ylmethyl and 2-pyrid-3-yl-2-morpholin-4-ylethyl.

The phrase "unsubstituted alkoxyalkyl" refers to an unsubstituted alkyl group as defined above in which a carbon bond or hydrogen bond is replaced by a bond to an oxygen atom which is bonded to an unsubstituted alkyl group as defined above.

The phrase "substituted alkoxyalkyl" refers to an unsubstituted alkoxyalkyl group as defined above in which a bond to a carbon or hydrogen group of the alkyl group and/or the alkoxy group of the alkoxyalkyl group is bonded to a non-carbon and non-hydrogen atom as described above with respect to substituted alkyl groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

In one aspect, the present invention provides a method for treating drug-resistant cancer. The method includes administering to a subject in need thereof a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture. In such methods, the subject is a cancer patient with drug-resistant cancer, and the compound of formula I has the following formula:

$R^{10}$ and $R^{13}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

$R^{11}$ and $R^{14}$ may be the same or different and are independently selected from substituted or unsubstituted alkyl groups, substituted or unsubstituted aryl groups, or substituted or unsubstituted heterocyclyl groups;

$R^{12}$ and $R^{15}$ may be the same or different and are independently selected from substituted or unsubstituted alkyl groups, substituted or unsubstituted aryl groups, or substituted or unsubstituted heterocyclyl groups; and $R^{16}$ is selected from substituted or unsubstituted alkyl groups, substituted or unsubstituted aryl groups, or substituted or unsubstituted heterocyclyl groups.

In some embodiments of the method for treating drug-resistant cancer, the subject is administered a compound of formula II, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula II has the following formula and $R^7$ is a substituted or unsubstituted heterocyclyl group:

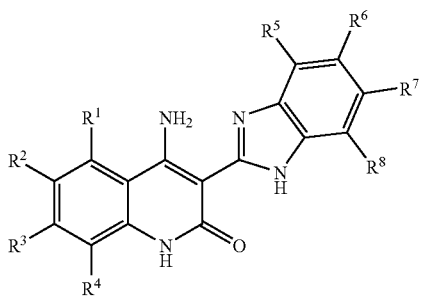

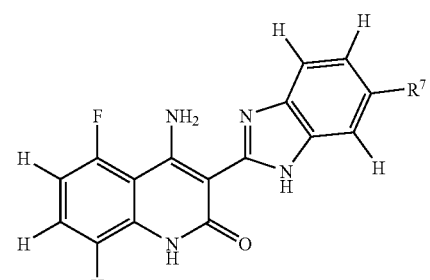

wherein:

$R^1$, $R^2$, $R^3$, and $R^4$ may be the same or different and are independently selected from H, Cl, Br, F, I, —$OR^{10}$ groups, —$NR^{11}R^{12}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, or substituted or unsubstituted heterocyclylalkyl groups;

$R^5$, $R^6$, $R^7$, and $R^8$ may be the same or different and are independently selected from H, Cl, Br, F, I, —$OR^{13}$ groups, —$NR^{14}R^{15}$ groups, —$SR^{16}$ groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, substituted or unsubstituted alkoxyalkyl groups, substituted or unsubstituted aryloxyalkyl groups, or substituted or unsubstituted heterocyclyloxyalkyl groups;

In some such embodiments, $R^7$ is a substituted or unsubstituted heterocyclyl group selected from a substituted or unsubstituted piperidinyl group, piperazinyl group, or morpholinyl group. In some of these embodiments, $R^7$ is a substituted or unsubstituted N-alkyl piperazinyl group. In some such embodiments, $R^7$ is a substituted or unsubstituted N-alkyl piperazinyl group and the alkyl group of the N-alkyl piperazinyl comprises from 1 to 4 carbon atoms.

In some embodiments of the method for treating drug-resistant cancer, the subject is administered a compound of formula III, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula III as the following formula:

III

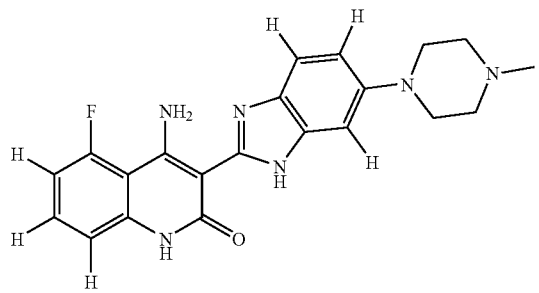

The invention also provides a method for treating cancer. The method includes administering to a subject in need thereof, an anti-cancer drug selected from Gleevec, BAY43-9006, Brostallicin, lenalidomide (Revlimid), thalidomide (Thalomid), docetaxel (Taxotere), erlotinib (Tarceva), vatalinib (PTK-787), VEGF-trap, fenretidine, bortezomib, bevacizumab (Avastin), pertuzumab, and/or rituximab, and a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula I has the structure and properties shown above with respect to the method of treating drug-resistant cancer. The compounds of formula I, II, and III are useful in treating cancer patients refractory to one or more of these anti-cancer drugs. The compounds of formula I, II, and III are useful in treating cancer patients with cancers that are refractory or resistant to one or more of these anti-cancer drugs.

In one embodiment of the method for treating cancer, the subject is administered a compound of formula II, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula II has the formula shown above, and $R^7$ is a substituted or unsubstituted heterocyclyl group. In some such embodiments, $R^7$ is a substituted or unsubstituted heterocyclyl group selected from a substituted or unsubstituted piperidinyl group, piperazinyl group, or morpholinyl group. In some of these embodiments, $R^7$ is a substituted or unsubstituted N-alkyl piperazinyl group. In some such embodiments, $R^7$ is a substituted or unsubstituted N-alkyl piperazinyl group and the alkyl group of the N-alkyl piperazinyl comprises from 1 to 4 carbon atoms.

In one embodiment of the method for treating cancer, the subject is administered a compound of formula III, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula III has the formula shown above.

In some embodiments of the method for treating cancer, the compound, the tautomer, the salt of the compound, the salt of the tautomer, the mixture, or the pharmaceutical composition is administered to the subject after the anti-cancer drug has been administered to the subject. In other embodiments, the compound, the tautomer, the salt of the compound, the salt of the tautomer, the mixture, or the pharmaceutical composition is administered to the subject before the anti-cancer drug has been administered to the subject. In still other embodiments, the compound, the tautomer, the salt of the compound, the salt of the tautomer, the mixture, or the pharmaceutical composition is administered to the subject at the same time that at least some of the anti-cancer drug is administered to the subject.

In some embodiments, a stable disease state is achieved and/or a reduction in tumor size occurs in the subject after administration of the compound, the tautomer, the salt of the compound, the salt of the tautomer, the mixture, or the pharmaceutical composition.

In another aspect, the invention provides therapeutic compositions and kits. Such compositions and kits include an anti-cancer drug and a compound of formula I, a tautomer of the compound, a salt of the compound, a salt of the tautomer, or a mixture thereof. Such therapeutic compositions and kits may include the components as a combined preparation for simultaneous, separate, or sequential use in the treatment of a subject that has drug-resistant cancer Formula I has the same structure and properties as described above with respect to the method for treating drug-resistant cancer. In some embodiments, the anti-cancer drug included in the kits and therapeutic compositions is an anti-cancer drug other than the drug that the cancer is resistant to. In other embodiments, the anti-cancer drug included in the kits and therapeutic compositions is the anti-cancer drug that the cancer is resistant to. For example, if a patient is refractory to Gleevec, then a kit or composition may include one or more compound of formula I, II, and/or III in addition an anti-cancer drug such as Iressa. Alternatively, if a patient is refractory to Gleevec, the kit or composition may include one or more compound of formula I, II, and/or III and Gleevec. The purpose for the inclusion of Gleevec is that drug-resistance in a patient may not be known until the drug is administered to the patient. Additionally, resistance to a certain drug may develop during treatment. Kits may include one, two, three, or more different anti-cancer drugs in addition to the compounds of the invention.

In some embodiments of the kits and therapeutic compositions, the compound of formula I, the tautomer of the compound, the salt of the compound, the salt of the tautomer, or the mixture thereof is a compound of formula II, a tautomer of the compound of formula II, a salt of the compound of formula II, a salt of the tautomer of the compound of formula II, or a mixture thereof, wherein the compound of formula II has the formula shown above and $R^7$ is a substituted or unsubstituted heterocyclyl group. In some such embodiments, $R^7$ is a substituted or unsubstituted heterocyclyl group selected from a substituted or unsubstituted piperidinyl group, piperazinyl group, or morpholinyl group. In some of these embodiments, $R^7$ is a substituted or unsubstituted N-alkyl piperazinyl group. In some such embodiments, $R^7$ is a substituted or unsubstituted N-alkyl piperazinyl group and the alkyl group of the N-alkyl piperazinyl comprises from 1 to 4 carbon atoms In some embodiments of the kits and therapeutic compositions, the compound of formula I, the tautomer of the compound, the salt of the compound, the salt of the tautomer, or the mixture thereof is a compound of formula III, a tautomer of the compound of formula III, a salt of the compound of formula III, a salt of the tautomer of the compound of formula III, or a mixture thereof, wherein the compound of formula III has the formula shown above.

In some embodiments of the therapeutic compositions and kits, the anti-cancer drug and the compound, the tautomer, the salt of the compound, the salt of the tautomer, the mixture, or the pharmaceutical composition are provided as a single composition. In other embodiments, the anti-cancer drug and the compound, the tautomer, the salt of the compound, the salt of the tautomer, the mixture, or the pharmaceutical composition are provided separately as parts of a kit.

The invention also provides a method for inhibiting a kinase in a subject. The method includes administering to a subject in need thereof, a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture, wherein the subject is a cancer patient and the kinase comprises a mutant gatekeeper residue, wherein the compound of formula I has the structure and properties shown above with respect to the method of treating drug-resistant cancer.

In one embodiment of the method for inhibiting a kinase, the subject is administered a compound of formula II, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula II has the formula shown above, and $R^7$ is a substituted or unsubstituted heterocyclyl group. In some such embodiments, $R^7$ is a substituted or unsubstituted heterocyclyl group selected from a substituted or unsubstituted piperidinyl group, piperazinyl group, or morpholinyl group. In some of these embodiments, $R^7$ is a substituted or unsubstituted N-alkyl piperazinyl group. In some such embodiments, $R^7$ is a substituted or unsubstituted N-alkyl piperazinyl group and the alkyl group of the N-alkyl piperazinyl comprises from 1 to 4 carbon atoms.

In one embodiment of the method for inhibiting a kinase, the subject is administered a compound of formula III, a tautomer of the compound, a salt of the compound, a salt of the tautomer, a mixture thereof, or a pharmaceutical composition comprising the compound, the tautomer, the salt of the compound, the salt of the tautomer, or the mixture, wherein the compound of formula III has the formula shown above.

In one embodiment of the method for inhibiting a kinase, the kinase is a cytoplasmic tyrosine kinase or is a receptor tyrosine kinase. IN some embodiments, the kinase is selected from ABL, KIT, PDGFRa, EGFR, or FLT3. In some such embodiments, the kinase is ABL (T315I). In other such embodiments, the kinase is FLT3 (D835Y). In other such embodiments, the kinase is EGFR.

In some embodiments of the method for inhibiting a kinase, the cancer is resistant to imatinib mesylate (Gleevec), BAY43-9006, Brostallicin, lenalidomide (Revlimid), thalidomide (Thalomid), docetaxel (Taxotere), erlotinib (Tarceva), gefitinib (Iressa), vatalinib (PTK-787), VEGF-rap, fenretidine, bortezomib, or a general monoclonal antibody. In some embodiments, the cancer of the cancer patient is selected from gastro intestinal stromal tumor, acute myelogenous leukemia, chronic myelogenous leukemia, multiple myeloma, renal cell carcinoma, non-small cell lung cancer, or hypereosinophilic syndrome (HES).

The invention also provides a method for treating a subject suffering from a cancer associated with overexpression of pERK. The method includes measuring endogenous pERK levels in the patient and administering to the, a compound of formula I, a tautomer of the compound, a salt of the compound, a salt of the tautomer, a mixture thereof, or a pharmaceutical composition comprising the compound, the tautomer, the salt of the compound, the salt of the tautomer, or the mixture. In some such embodiments, the measuring of the endogenous pERK level is conducted before the administration. In such embodiments, the measuring may be performed to determine a patient in need of the compound, the tautomer, the salt of the compound, the salt of the tautomer, the mixture, or the pharmaceutical composition. In other embodiments, the measuring of the endogenous pERK level is conducted after the administration. In such embodiments, the measuring may be performed to determine the effectiveness of the administration of the compound, the tautomer, the salt of the compound, the salt of the tautomer, the mixture, or the pharmaceutical composition in the patient. In some embodiments, the compound of formula I is a compound of formula II or a compound of formula III, a salt thereof, a salt of the tautomer thereof, a mixture thereof, or a pharmaceutical composition comprising one of these.

In some embodiments of the method for treating a subject suffering from a cancer associated with overexpression of pERK, the measuring of endogenous pERK levels in the patients comprises extracting blood containing peripheral blood leukocytes and measuring endogenous pERK levels by Western Blot and/or flow cytometry assays. In some embodiments, the pERK levels in the subject are elevated. In other such embodiments, the pERK levels are stabilized or reduced in the subject.

In some embodiments, $R^1$ is selected from H, Cl, Br, F, or I. In some such embodiments, $R^1$ is F. In some embodiments, $R^2$, $R^3$ and $R^4$ are all H. In some such embodiments, $R^1$ is F and each of $R^2$, $R^3$ and $R^4$ is H.

In other embodiments, at least one of $R^6$ or $R^7$ is a substituted or unsubstituted heterocyclyl group. In some such embodiments, one of $R^6$ or $R^7$ is a heterocyclyl group and the other of $R^6$ or $R^7$ is a H. In some embodiments, one of $R^6$ or $R^7$ is a heterocyclyl group selected from a substituted or unsubstituted piperidinyl group, piperazinyl group, or morpholinyl group. In some such embodiments one of $R^6$ or $R^7$ is an N-alkyl piperazinyl group such as an N-methyl piperazinyl group or the like and, in some such embodiments, the other of $R^6$ or $R^7$ is a H.

In various embodiments, the lactic salt of the compound is administered to the subject or is included in the kits or therapeutic compositions of the invention.

In various embodiments, the cancer is resistant to Gleevec. In other embodiments, the compound, the tautomer, the salt of the compound, the salt of the tautomer, the mixture, or the pharmaceutical composition is administered to the subject after Gleevec has been administered to the subject and the cancer in the subject has been found to be resistant to Gleevec.

In various embodiments, the cancer is resistant to BAY43-9006. In other embodiments, the compound, the tautomer, the salt of the compound, the salt of the tautomer, the mixture, or the pharmaceutical composition is administered to the subject after BAY43-9006 has been administered to the subject and the cancer in the subject has been found to be resistant to BAY43-9006.

In various embodiments, the cancer is resistant to Brostallicin. In other embodiments, the compound, the tautomer, the salt of the compound, the salt of the tautomer, the mixture, or the pharmaceutical composition is administered to the subject after Brostallicin has been administered to the subject and the cancer in the subject has been found to be resistant to Brostallicin.

In various embodiments, the cancer is resistant to, or the compounds, salts, tautomers, mixtures, or pharmaceutical compositions of the invention are used in combination with, one of the following anti-cancer drugs which are each individually preferred: lenalidomide (Revlimid), thalidomide (Thalomid), docetaxel (Taxotere), erlotinib (Tarceva), gefitinib (Iressa), vatalinib (PTK-787), VEGF-trap, fenretidine, bortezomib, or a general monoclonal antibody (mAb) such as, but not limited to, bevacizumab (Avastin), pertuzumab, or rituximab. Trastuzumab (Herceptin) may also be used in combination with the compounds of the present invention.

Various cancers can be treated with the methods, compositions, and kits of the present invention. In some embodiments, the cancer is a solid cancer such as a solid tumor which, in some embodiments is drug-resistant. In other embodiments, the cancer is "liquid" cancer or a hematological cancer. In still other embodiments, the cancer is gastro intestinal stromal tumor (GIST). In other embodiments, the cancer is acute myelogenous leukemia. In yet other embodiments, the cancer is chronic myelogenous leukemia, multiple myeloma, or renal cell carcinoma. In still other embodiments, the cancer is selected from prostate cancer, renal cancer, gastro intestinal stromal tumor, sarcoma, colorectal cancer, breast cancer, parotid cancer, gastric cancer, melanoma, oesophageal cancer, NET (sinonasal) cancer, colon cancer, ovarian cancer, or liver cancer which, in some embodiments, is drug-resistant. A list of other cancers that may be treated in accordance with the present invention includes, but is not limited to, gastro intestinal stromal tumor, acute myelogenous leukemia, chronic myelogenous leukemia, multiple myeloma, renal cell carcinoma, non-small cell lung cancer, or hypereosinophilic syndrome (HES).

In various groups that include heterocyclyl groups, the heterocyclyl group may be attached in various ways. For example, in an —OCH$_2$(CH$_2$)$_q$(heterocyclyl) group, where q is selected from 0, 1, 2, 3, or 4, the heterocyclyl group may be bonded to a methylene carbon of the —OCH$_2$(CH$_2$)$_q$ group of the —OCH$_2$(CH$_2$)$_q$(heterocyclyl) through various ring members. By way of non-limiting example, where q is 1 and the heterocyclyl group is tetrahydrofuran, the group could be represented by the formula —OCH$_2$CH$_2$(tetrahydrofuranyl) which corresponds to the following two structures:

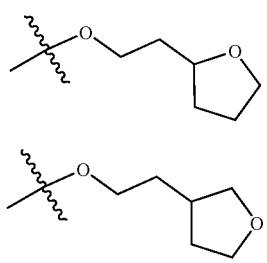

IV

V where structure IV represents the group that can be referred to as the —OCH$_2$CH$_2$(2-tetrahydrofuranyl) group and structure V represents the group that can be referred to as the —OCH$_2$CH$_2$(3-tetrahydrofuranyl) group. When the heterocyclyl group is a N-containing heterocycle, such as, but not limited to piperidine, piperazine, morpholine, or pyrrolidine, the heterocycle can be bonded to the methylene carbon through a ring carbon atom or through a nitrogen atom in the ring of the N-containing heterocycle. Both of these are preferred. Where the heterocyclyl group is a piperidine and q is 2 for an —OCH$_2$(CH$_2$)$_q$(heterocyclyl) group, the following structures are possible and preferred:

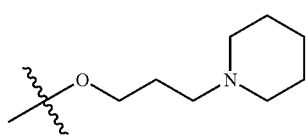

VI

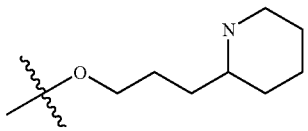

VII

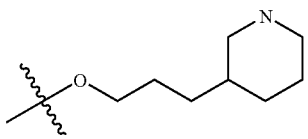

VIII

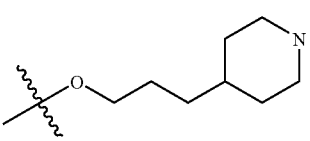

IX

Structure VI is an example of a —O(CH$_2$)$_3$(N-piperidinyl) or —O(CH$_2$)$_3$(1-piperidinyl) group. Structure VII is an example of a —O(CH$_2$)$_3$-(2-piperidinyl) group, Structure VII is an example of a —O(CH$_2$)$_3$(3-piperidinyl) group. Structure IX is an example of a —O(CH$_2$)$_3$(4-piperidinyl) group. Where the heterocyclyl group is a piperazine and q is 1 for an —OCH$_2$(CH$_2$)$_q$(heterocyclyl) group, the following structures are possible and preferred:

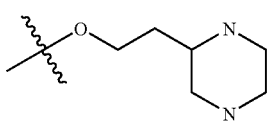

X

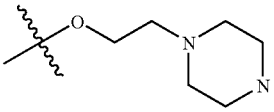

XI

Structure X is an example of a —O(CH$_2$)$_2$(2-piperazinyl) group, and structure XI is an example of a —O(CH$_2$)$_2$(1-piperazinyl) or —O(CH$_2$)$_2$(N-piperazinyl) group. Where the heterocyclyl group is a morpholine and q is 1 for an —OCH$_2$(CH$_2$)$_q$(heterocyclyl) group, the following structures are possible and preferred:

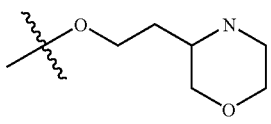

XII

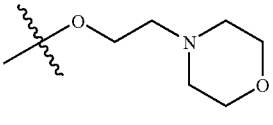

XIII

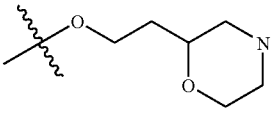

XIV

Structure XII is an example of a —O(CH$_2$)$_2$(3-morpholinyl) group, structure XIII is an example of a —O(CH$_2$)$_2$(4- morpholinyl) or —O(CH$_2$)$_2$(N-morpholinyl) group, and structure XIV is an example of a —O(CH$_2$)$_2$(2-morpholinyl) group. It will be observed that where the group is a pyrrolidine, and q is 1, the structures available include —O(CH$_2$)$_2$ (1-pyrrolidinyl) or —O(CH$_2$)$_2$(N-pyrrolidinyl), —O(CH$_2$)$_2$ (2-pyrrolidinyl), and —O(CH$_2$)$_2$(3-pyrrolidinyl).

Scheme 1 depicts one exemplary synthetic route for the synthesis of a benzimidazolyl quinolinone compound and should not be interpreted to limit the invention in any manner.

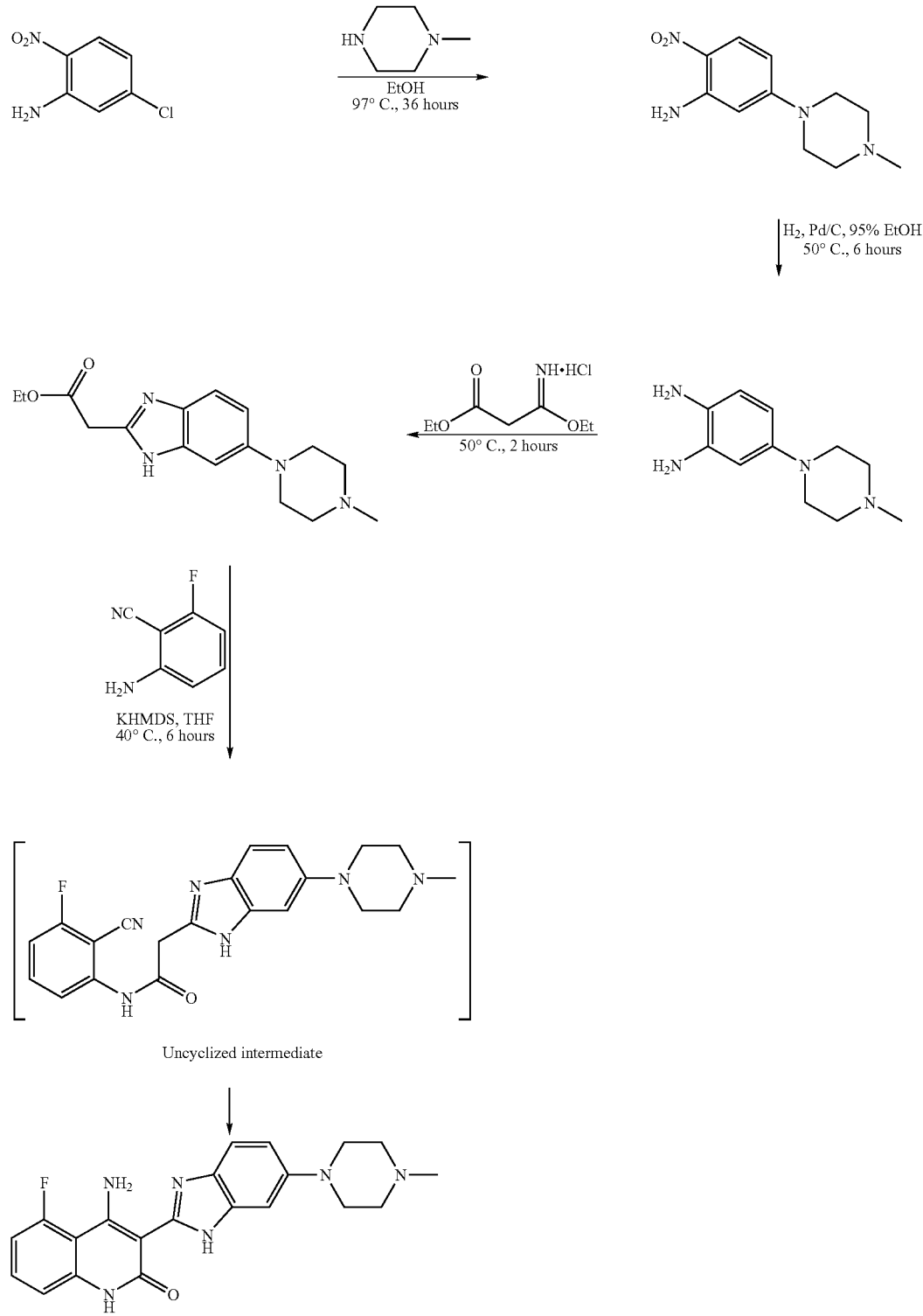

Scheme 2 depicts another method for synthesizing a compound of the invention and does not limit the invention in any manner. Those skilled in the art will understand that the selection of a substituted or unsubstituted diaminobenzene and a substituted or unsubstituted anthranilonitrile allows for the synthesis of a wide variety of compounds. Those skilled in the art will also recognize that certain groups may need protection using standard protecting groups for the final cyclization reaction. The extremely versatile synthetic route allows a plethora of compounds having the formula II to be readily prepared by a highly convergent and efficient synthetic route.

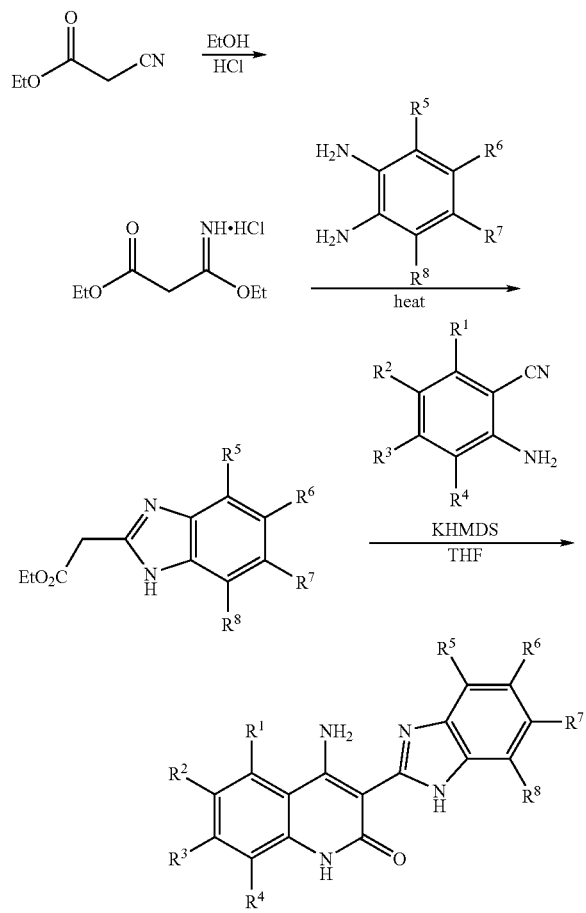

Scheme 2

Compounds of Structure I are readily synthesized using the procedures described in the following Examples section and disclosed in the following documents which are each hereby incorporated by reference in their entireties and for all purposes as if fully set forth herein: U.S. Pat. No. 6,605,617, published U.S. Patent Application No. 2004/0092535, U.S. patent application Ser. No. 10/983,174, published U.S. Patent Application No. 2004/0220196, U.S. patent application Ser. Nos. 10/982,757, and 10/982,543.

The compounds of Structure I, tautomers of the compounds, pharmaceutically acceptable salts of the compounds, pharmaceutically acceptable salts of the tautomers, and mixtures thereof may be used to prepare medicaments, that may be used for the purposes described herein, and may be used to treat various biological conditions as described herein. The compounds, salts, tautomers, salts of the tautomers, and mixtures thereof of the invention are particularly useful in treating patients that have cancer which is resistant to one or more other anti-cancer drugs such as Gleevec, BAY43-9006, and Brostallicin.

Pharmaceutical formulations may include any of the compounds, tautomers, or salts of any of the embodiments described above in combination with a pharmaceutically acceptable carrier such as those described herein. Such formulations may also include a different anti-cancer drug such as, but not limited to, Gleevec, BAY43-9006, or Brostallicin.

The instant invention also provides for compositions which may be prepared by mixing one or more compounds of the instant invention, or pharmaceutically acceptable salts tautomers thereof, or mixtures thereof with pharmaceutically acceptable carriers, excipients, binders, diluents or the like to treat or ameliorate disorders related to metastacized tumors. The compositions of the inventions may be used to create formulations used to treat metastacized tumors as described herein. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, pharmaceutically acceptable salts, tautomers, or mixtures thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference in its entirety for all purposes as if fully set forth herein.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients with a metastasized hematologic tumor, successful treatment may include a reduction in the proliferation of capillaries feeding the tumor(s) or diseased tissue, an alleviation of symptoms related to a cancerous growth or tumor, proliferation of capillaries, or diseased tissues a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs such as, but not limited to, Gleevec, BAY43-9006, and Brostallicin and drugs used in antisense and gene therapy. Appropriate combinations can be determined by those of skill in the oncology and medicine arts.

A "stable disease state" as used with respect to cancer treatment means a cessation in the growth of the cancer. This may often be visualized using a scanning method such as positron emission tomography (PET) as shown in the Figures.

Pharmaceutical formulations and medicaments according to the invention include the compound of Structure I or the tautomers, salts, or mixtures thereof in combination with a pharmaceutically acceptable carrier. Thus, the compounds of the invention may be used to prepare medicaments and pharmaceutical formulations. Such medicaments and pharmaceutical formulations may be used in the method of treatment described herein.

The compounds and formulations of the present invention are particularly suitable for use in combination therapy as they have been shown to exhibit synergistic effect when used in combination with anti-cancer drugs such as, but not limited to, camptothecin, doxorubicin, cisplatin, irinotecan (CPT-11), alkylating agents, topoisomerase I and II inhibitors, and radiation treatment. Furthermore, the compounds of the invention may be used in combination with anti-cancer drugs such as Gleevec, BAY43-9006, and Brostallicin, and find particular use in cancer patients with cancer that is resistant to these anti-cancer drugs. Therefore, the invention provides pharmaceutical formulations that include the compound of Structure I and tautomers, salts, and/or mixtures thereof in combination with an anticancer drug. The invention also provides the use of the compounds, tautomers, salts, and/or mixtures in creating such formulations and medicaments and the use of the compounds in treating cancer patients.

In some embodiments, the invention provides therapeutic compositions comprising, an anti-cancer drug and a compound, a tautomer, a salt of the compound, a salt of the tautomer, or a mixture thereof of any embodiment of the invention as a combined preparation for the simultaneous, separate, or sequential use in the treatment of a patient, such as a cancer patient. In some such embodiments, the patient is a cancer patient that is resistant to at least one anti-cancer drug, such as Gleevec, BAY43-9006, or Brostallicin. In some such embodiments, the anti-cancer drug and the compound, the tautomer, the salt of the compound, the salt of the tautomer, or the mixture thereof are provided as a single composition. In other such embodiments, the anti-cancer drug and the compound, the tautomer, the salt of the compound, the salt of the tautomer, or the mixture thereof are provided separately as parts of a kit. Such kits may further include instructions for use.

The compounds of the invention may be used to treat a variety of subjects. Suitable subjects include animals such as mammals and humans. Suitable mammals include, but are not limited to, primates such as, but not limited to lemurs, apes, and monkeys; rodents such as rats, mice, and guinea pigs; rabbits and hares; cows; horses: pigs; goats; sheep; marsupials; and carnivores such as felines, canines, and ursines. In some embodiments, the subject or patient is a human. In other embodiments, the subject or patient is a rodent such as a mouse or a rat. In some embodiments, the subject or patient is an animal other than a human and in some such embodiments, the subject or patient is a mammal other than a human.

EXAMPLES

The following abbreviations are used in the Examples:
EtOH: Ethanol
H₂O: Water
HCl: Hydrochloric acid
HPLC: High Performance Liquid Chromatography
KHMDS: Potassium bis(trimethylsilyl)amide
LiHMDS: Lithium bis(trimethylsilyl)amide
NaHMDS: Sodium bis(trimethylsilyl)amide
NaOH: Sodium hydroxide
N₂: Nitrogen
TBME: t-Butyl methyl ether
THF: Tetrahydrofuran Nomenclature for the Example compounds was provided using ACD Name version 5.07 software (Nov. 14, 2001) available from Advanced Chemistry Development, Inc., ChemInnovation NamExpert+Nomenclator™ brand software available from ChemInnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

Various starting materials may be obtained from commercial sources and prepared by methods known to one of skill in the art.

Example 1

Synthesis of
5-(4-Methyl-piperazin-1-yl)-2-nitroaniline

Procedure A

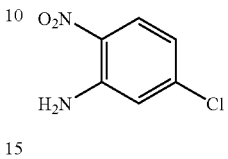 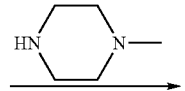

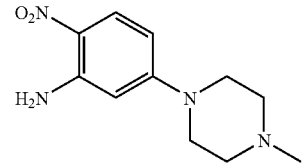

5-Chloro-2-nitroaniline (500 g, 2.898 mol) and 1-methyl piperazine (871 g, 8.693 mol) were placed in a 2000 mL flask fitted with a condenser and purged with N₂. The flask was placed in an oil bath at 100° C. and heated until the 5-chloro-2-nitroaniline was completely reacted (typically overnight) as determined by HPLC. After HPLC confirmed the disappearance of the 5-chloro-2-nitroaniline, the reaction mixture was poured directly (still warm) into 2500 mL of room temperature water with mechanical stirring. The resulting mixture was stirred until it reached room temperature and then it was filtered. The yellow solid thus obtained was added to 1000 mL of water and stirred for 30 minutes. The resulting mixture was filtered, and the resulting solid was washed with TBME (500 mL, 2×) and then was dried under vacuum for one hour using a rubber dam. The resulting solid was transferred to a drying tray and dried in a vacuum oven at 50° C. to a constant weight to yield 670 g (97.8%) of the title compound as a yellow powder.

Procedure B

5-Chloro-2-nitroaniline (308.2 g, 1.79 mol) was added to a 4-neck 5000 mL round bottom flask fitted with an overhead stirrer, condenser, gas inlet, addition funnel, and thermometer probe. The flask was then purged with N₂. 1-Methylpiperazine (758.1 g, 840 mL, 7.57 mol) and 200 proof ethanol (508 mL) were added to the reaction flask with stirring. The flask was again purged with N₂, and the reaction was maintained under N₂. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 20° C. to 2500 with stirring, and the reaction was stirred for 2 to 3 hours. Seed crystals (0.20 g, 0.85 mmol) of 5-(4-methyl-piperazin-1-yl)-2-nitroaniline were added to the reaction mixture unless precipitation had already occurred. Water (2,450 mL) was added to the stirred reaction mixture over a period of about one hour while the internal temperature was maintained at a temperature ranging from about 20° C. to 30° C. After the addition of water was complete, the resulting mixture was stirred for about one hour at a temperature of 20° C. to 30° C. The resulting mixture was then filtered, and the flask and filter cake were washed with water (3×2.56 L). The golden yellow solid product was dried to a constant weight of 416 g (98.6% yield) under vacuum at about 50° C. in a vacuum oven.

Procedure C

5-Chloro-2-nitroaniline (401 g, 2.32 mol) was added to a 4-neck 12 L round bottom flask fitted with an overhead stirrer, condenser, gas inlet, addition funnel, and thermometer probe. The flask was then purged with $N_2$. 1-Methylpiperazine (977 g, 1.08 L, 9.75 mol) and 100% ethanol (650 mL) were added to the reaction flask with stirring. The flask was again purged with $N_2$, and the reaction was maintained under $N_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 80° C. with stirring, and water (3.15 L) was added to the mixture via an addition funnel over the period of 1 hour while the internal temperature was maintained at 82° C. (+/−3° C.). After water addition was complete, heating was discontinued and the reaction mixture was allowed to cool over a period of no less than 4 hours to an internal temperature of 20-25° C. The reaction mixture was then stirred for an additional hour at an internal temperature of 20-30° C. The resulting mixture was then filtered, and the flask and filter cake were washed with water (1×1 L), 50% ethanol (1×1 L), and 95% ethanol (1×1 L). The golden yellow solid product was placed in a drying pan and dried to a constant weight of 546 g (99% yield) under vacuum at about 50° C. in a vacuum oven.

Example 2

Synthesis of [6-(4-Methyl-piperazin-1-yl)-1H-benzimidazol-2-yl]-acetic acid ethyl ester Procedure A

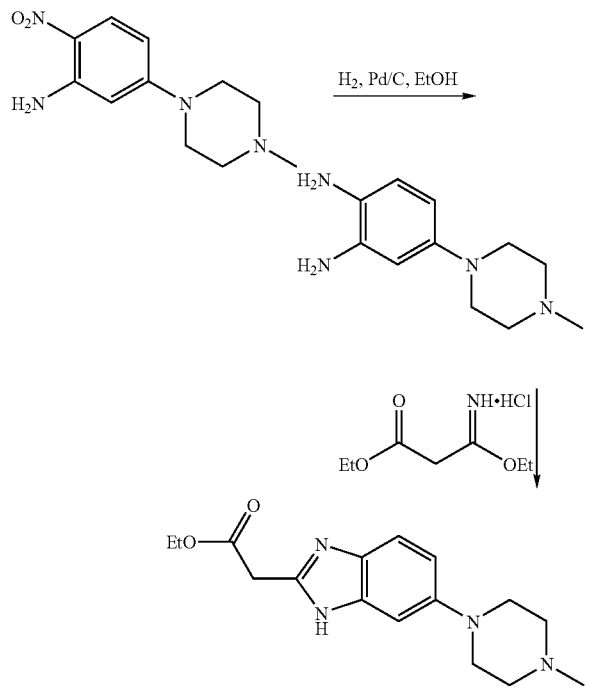

A 5000 mL, 4-neck flask was fitted with a stirrer, thermometer, condenser, and gas inlet/outlet. The equipped flask was charged with 265.7 g (1.12 mol. 1.0 eq) of 5-(4-methyl-piperazin-1-yl)-2-nitroaniline and 2125 mL of 200 proof ETOH. The resulting solution was purged with $N_2$ for 15 minutes. Next, 20.0 g of 5% Pd/C (50% $H_2O$ w/w) was added. The reaction was vigorously stirred at 40-50° C. (internal temperature) while $H_2$ was bubbled through the mixture. The reaction was monitored hourly for the disappearance of 5-(4-methyl-piperazin-1-yl)-2-nitroaniline by HPLC. The typical reaction time was 6 hours.

After all the 5-(4-methyl-piperazin-1-yl)-2-nitroaniline had disappeared from the reaction, the solution was purged with $N_2$ for 15 minutes. Next, 440.0 g (2.25 mol) of ethyl 3-ethoxy-3-iminopropanoate hydrochloride was added as a solid. The reaction was stirred at 40-50° C. (internal temperature) until the reaction was complete. The reaction was monitored by following the disappearance of the diamino compound by HPLC. The typical reaction time was 1-2 hours. After the reaction was complete, it was cooled to room temperature and filtered through a pad of Celite filtering material. The Celite filtering material was washed with absolute EtOH (2×250 mL), and the filtrate was concentrated under reduced pressure providing a thick brown/orange oil. The resulting oil was taken up in 850 mL of a 0.37% HCl solution. Solid NaOH (25 g) was then added in one portion, and a precipitate formed. The resulting mixture was stirred for 1 hour and then filtered. The solid was washed with $H_2O$ (2×400 mL) and dried at 50° C. in a vacuum oven providing 251.7 g (74.1%) of [6-(4-methyl-piperazin-1-yl)-1H-benzoimidazol-2-yl]-acetic acid ethyl ester as a pale yellow powder.

Procedure B

A 5000 mL, 4-neck jacketed flask was fitted with a mechanical stirrer, condenser, temperature probe, gas inlet, and oil bubbler. The equipped flask was charged with 300 g (1.27 mol) of 5-(4-methyl-piperazin-1-yl)-2-nitroaniline and 2400 mL of 200 proof EtOH (the reaction may be and has been conducted with 95% ethanol and it is not necessary to use 200 proof ethanol for this reaction). The resulting solution was stirred and purged with $N_2$ for 15 minutes. Next, 22.7 g of 5% Pd/C (50% $H_2O$ w/w) was added to the reaction flask. The reaction vessel was purged with $N_2$ for 15 minutes. After purging with $N_2$, the reaction vessel was purged with $H_2$ by maintaining a slow, but constant flow of $H_2$ through the flask. The reaction was stirred at 45-55° C. (internal temperature) while $H_2$ was bubbled through the mixture until the 5-(4-methyl-piperazin-1-yl)-2-nitroaniline was completely consumed as determined by HPLC. The typical reaction time was 6 hours.

After all the 5-(4-methyl-piperazin-1-yl)-2-nitroaniline had disappeared from the reaction, the solution was purged with $N_2$ for 15 minutes. The diamine intermediate is air sensitive so care was taken to avoid exposure to air. 500 g (2.56 mol) of ethyl 3-ethoxy-3-iminopropanoate hydrochloride was added to the reaction mixture over a period of about 30 minutes. The reaction was stirred at 45-55° C. (internal temperature) under $N_2$ until the diamine was completely consumed as determined by HPLC. The typical reaction time was about 2 hours. After the reaction was complete, the reaction was filtered while warm through a pad of Celite. The reaction flask and Celite were then washed with 200 proof EtOH (3×285 mL). The filtrates were combined in a 5000 mL flask, and about 3300 mL of ethanol was removed under vacuum producing an orange oil. Water (530 mL) and then 1 M HCL (350 mL) were added to the resulting oil, and the resulting mixture was stirred. The resulting solution was vigorously stirred while 30% NaOH (200 mL) was added over a period of about 20 minutes maintaining the internal temperature at about 25-30° C. while the pH was brought to between 9 and 10. The resulting suspension was stirred for about 4 hours while maintaining the internal temperature at about 20-25° C.

The resulting mixture was filtered, and the filter cake was washed with $H_2O$ (3×300 mL). The collected solid was dried to a constant weight at 50° C. under vacuum in a vacuum oven providing 345.9 g (90.1%) of [6-(4-methyl-piperazin-1-yl)-1H-benzoimidazol-2-yl]-acetic acid ethyl ester as a pale yellow powder. In an alternative work up procedure, the filtrates were combined and the ethanol was removed under vacuum until at least about 90% had been removed. Water at a neutral pH was then added to the resulting oil, and the solution was cooled to about 0° C. An aqueous 20% NaOH solution was then added slowly with rapid stirring to bring the pH up to 9.2 (read with pH meter). The resulting mixture was then filtered and dried as described above. The alternative work up procedure provided the light tan to light yellow product in yields as high as 97%.

Example 3

Method for Reducing Water Content of [6-(4-Methyl-piperazin-1-yl)-1H-benzoimidazol-2-yl]-acetic acid ethyl ester

[6-(4-Methyl-piperazin-1-yl)-1H-benzimidazol-2-yl]-acetic acid ethyl ester (120.7 grams) that had been previously worked up and dried to a water content of about 8-9% $H_2O$ was placed in a 2000 mL round bottom flask and dissolved in absolute ethanol (500 mL). The amber solution was concentrated to a thick oil using a rotary evaporator with heating until all solvent was removed. The procedure was repeated two more times. The thick oil thus obtained was left in the flask and placed in a vacuum oven heated at 50° C. overnight. Karl Fisher analysis results indicated a water content of 5.25%. The lowered water content obtained by this method provided increased yields in the procedure of Example 4. Other solvents such as toluene and THF may be used in place of the ethanol for this drying process.

Example 4

Synthesis of 4-Amino-5-fluoro-3-[6-(4-methyl-piperazin-1-yl)-1H-benzimidazol-2-yl]-1H-quinolin-2-one Procedure A

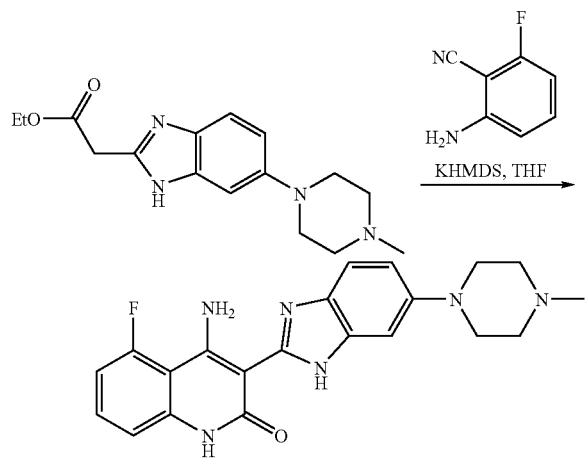

[6-(4-Methyl-piperazin-1-yl)-1H-benzimidazol-2-yl]-acetic acid ethyl ester (250 g, 820 mmol) (dried with ethanol as described above) was dissolved in THF (3800 mL) in a 5000 mL flask fitted with a condenser, mechanical stirrer, temperature probe, and purged with argon. 2-Amino-6-fluoro-benzonitrile (95.3 g, 700 mmol) was added to the solution, and the internal temperature was raised to 40° C. When all the solids had dissolved and the solution temperature had reached 40° C., solid KHMDS (376.2 g, 1890 mmol) was added over a period of 5 minutes. When addition of the potassium base was complete, a heterogeneous yellow solution was obtained, and the internal temperature had risen to 62° C. After a period of 60 minutes, the internal temperature decreased back to 40° C., and the reaction was determined to be complete by HPLC (no starting material or uncyclized intermediate was present). The thick reaction mixture was then quenched by pouring it into $H_2O$ (6000 mL) and stirring the resulting mixture until it had reached room temperature. The mixture was then filtered, and the filter pad was washed with water (1000 mL 2×). The bright yellow solid was placed in a drying tray and dried in a vacuum oven at 50° C. overnight providing 155.3 g (47.9%) of the desired 4-amino-5-fluoro-3-[6-(4-methyl-piperazin-1-yl)-1H-benzimidazol-2-yl]-1H-quinolin-2-one.

Procedure B

A 5000 mL 4-neck jacketed flask was equipped with a distillation apparatus, a temperature probe, a $N_2$ gas inlet, an addition funnel, and a mechanical stirrer. [6-(4-Methyl-piperazin-1-yl)-1H-benzimidazol-2-yl]-acetic acid ethyl ester (173.0 g, 570 mmol) was charged into the reactor, and the reactor was purged with $N_2$ for 15 minutes. Dry THF (2600 mL) was then charged into the flask with stirring. After all the solid had dissolved, solvent was removed by distillation (vacuum or atmospheric (the higher temperature helps to remove the water) using heat as necessary. After 1000 mL of solvent had been removed, distillation was stopped and the reaction was purged with $N_2$. 1000 mL of dry THF was then added to the reaction vessel, and when all solid was dissolved, distillation (vacuum or atmospheric) was again conducted until another 1000 mL of solvent had been removed. This process of adding dry THF and solvent removal was repeated at least 4 times (on the 4$^{th}$ distillation, 60% of the solvent is removed instead of just 40% as in the first 3 distillations) after which a 1 mL sample was removed for Karl Fischer analysis to determine water content. If the analysis showed that the sample contained less than 0.20% water, then reaction was continued as described in the next paragraph. However, if the analysis showed more than 0.20% water, then the drying process described above was continued until a water content of less than 0.20% was achieved.

After a water content of less than or about 0.20% was achieved using the procedure described in the previous paragraph, the distillation apparatus was replaced with a reflux condensers and the reaction was charged-with-2-amino-6-fluoro-benzonitrile (66.2 g-470 mmol)(in some procedures 0.95 equivalents is used). The reaction was then heated to an internal temperature of 38-42° C. When the internal temperature had reached 38-42° C., KHMDS solution (1313 g, 1.32 mol, 20% KHMDS in THF) was added to the reaction via the addition funnel over a period of 5 minutes maintaining the internal temperature at about 38-50° C. during the addition. When addition of the potassium base was complete, the reaction was stirred for 3.5 to 4.5 hours (in some examples it was stirred for 30 to 60 minutes and the reaction may be complete within that time) while maintaining the internal temperature at from 38-42° C. A sample of the reaction was then removed and analyzed by HPLC. If the reaction was not complete, additional KHMDS solution was added to the flask over a period of 5 minutes and the reaction was stirred at 38-42° C. for 45-60 minutes (the amount of KHMDS solution added was determined by the following: If the IPC ratio is <3.50, then 125 mL was added; if 10.0≧IPC ratio≧3.50, then 56 mL was added; if 20.0≧IPC ratio≧10, then 30 mL was added. The IPC ratio is equal to the area corresponding to 4-amino-5-fluoro-3-[6-(4-methyl-piperazin-1-yl)-1H-benzimidazol-2-yl]-1H-quinolin-2-one) divided by the area corresponding to the uncyclized intermediate). Once the reaction was complete (IPC ratio>20), the reactor was cooled to an internal temperature of 25-30° C., and water (350 mL) was charged into the reactor over a period of 15 minutes while maintaining the internal temperature at 25-35° C. (in one alternative, the reaction is conducted at 40° C. and water is added within 5 minutes. The quicker quench reduces the amount of impurity that forms over time). The reflux condenser was then replaced with a distillation apparatus and solvent was removed by distillation (vacuum or atmospheric) using heat as required. After 1500 mL of solvent had been removed, distillation was discontinued and the reaction was purged with N₂ Water (1660 mL) was then added to the reaction flask while maintaining the internal temperature at 20-30° C. The reaction mixture was then stirred at 20-30° C. for 30 minutes before cooling it to an internal temperature of 5-10° C. and then stirring for 1 hour. The resulting suspension was filtered, and the flask and filter cake were washed with water (3×650 mL). The solid thus obtained was added to a constant weight under vacuum at 50° C. in a vacuum oven to provide 103.9 g (42.6% yield) of 4-amino-5-fluoro-3-[6-(4-methyl-piperazin-1-yl)-1H-benzimidazol-2-yl]-1H-quinolin-2-one as a yellow powder.

Procedure C

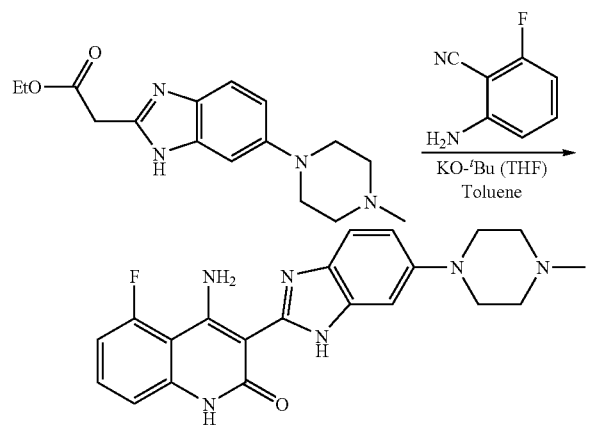

[6-(4-Methyl-piperazin-1-yl)-1H-benzimidazol-2-yl]-acetic acid ethyl ester (608 g, 2.01 mol) (dried) and 2-amino-6-fluoro-benzonitrile (274 g, 2.01 mol) were charged into a 4-neck 12 L flask seated on a heating mantle and fitted with a condenser, mechanical stirrer, gas inlet, and temperature probe. The reaction vessel was purged with N₂, and toluene (7.7 L) was charged into the reaction mixture while it was stirred. The reaction vessel was again purged with N₂ and maintained under N₂. The internal temperature of the mixture was raised until a temperature of 63° C. (+/−3° C.) was achieved. The internal temperature of the mixture was maintained at 63° C. (+/−3° C.) while approximately 2.6 L of toluene was distilled from the flask under reduced pressure (380+/−10 torr, distilling head t=40° C. (+/−10° C.) (Karl Fischer analysis was used to check the water content in the mixture. If the water content was greater than 0.03%, then another 2.6 L of toluene was added and distillation was repeated. This process was repeated until a water content of less than 0.03% was achieved). After a water content of less than 0.03% was reached, heating was discontinued, and the reaction was cooled under N₂ to an internal-temperature of 17-19° C. Potassium t-butoxide in THF (20% in THF; 3.39 kg, 6.04 moles potassium t-butoxide) was then added to the reaction under N₂ at a rate such that the internal temperature of the reaction was kept below 20° C. After addition of the potassium t-butoxide was complete, the reaction was stirred at an internal temperature of less than 20° C. for 30 minutes. The temperature was then raised to 25° C., and the reaction was stirred for at least 1 hour. The temperature was then raised to 30° C., and the reaction was stirred for at least 30 minutes. The reaction was then monitored for completion using HPLC to check for consumption of the starting materials (typically in 2-3 hours, both starting materials were consumed (less than 0.5% by area % HPLC)). If the reaction was not complete after 2 hours, another 0.05 equivalents of potassium t-butoxide was added at a time, and the process was completed until HPLC showed that the reaction was complete. After the reaction was complete, 650 mL of water was added to the stirred reaction mixture. The reaction was then warmed to an internal temperature of 50° C. and the THF was distilled away (about 3 L by volume) under reduced pressure from the reaction mixture. Water (2.6 L) was then added dropwise to the reaction mixture using an addition funnel. The mixture was then cooled to room temperature and stirred for at least 1 hour. The mixture was then filtered, and the filter cake was washed with water (1.2 L), with 70% ethanol (1.2 L), and with 95% ethanol (1.2 L). The bright yellow solid was placed in a drying tray and dried in a vacuum oven at 50° C. until a constant weight was obtained providing 674 g (85.4%) of the desired 4-amino-5-fluoro-3-[6-(4-methyl-piperazin-1-yl)-1H-benzimidazol-2-yl]-1H-quinolin-2-one.

Example 5

Purification of 4-Amino-5-fluoro-3-[6-(4-methyl-piperazin-1-yl)-1H-benzimidazol-2-yl]-1H-quinolin-2-one A 3000 mL 4-neck flask equipped with a condenser, temperature probe, N₂ gas inlet, and mechanical stirrer was placed in a heating mantle. The flask was then charged with 4-amino-5-fluoro-3-[6-(4-methyl-piperazin-1-yl)-1H-benzimidazol-2-yl]-1H-quinolin-2-one (101.0 g, 0.26 mol), and the yellow solid was suspended in 95% ethanol (1000 mL) and stirred. In some cases an 8:1 solvent ratio is used. The suspension was then heated to a gentle reflux (temperature of about 76° C.) with stirring over a period of about 1 hour. The reaction was then stirred for 45-75 minutes while refluxed. At this point, the heat was removed from the flask and the suspension was allowed to cool to a temperature of 25-30° C. The suspension was then filtered, and the filter pad was washed with water (2×500 mL). The yellow solid was then placed in a drying tray and dried in a vacuum oven at 50° C. until a constant weight was obtained (typically 16 hours) to obtain 97.2 g (96.2%) of the purified product as a yellow powder.

Example 6

Preparation of Lactic Acid salt of 4-Amino-5-fluoro-3-[6-(4-methyl-piperazin-1-yl)-1H-benzimidazol-2-yl]-1H-quinolin-2-one

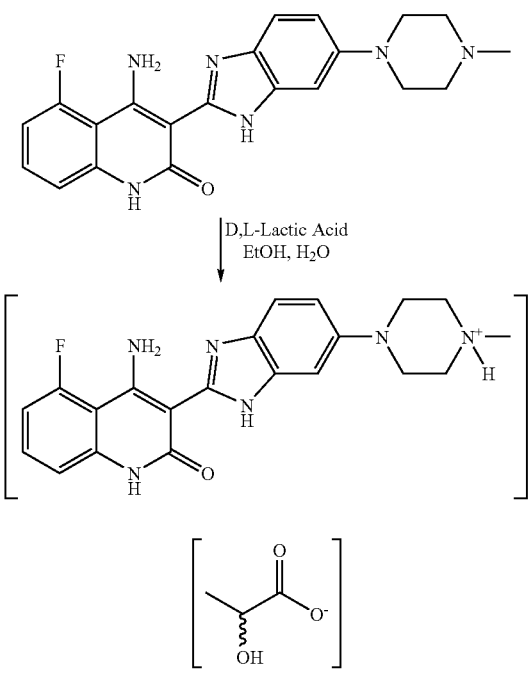

A 3000 mL 4-necked jacketed flask was fitted with a condenser, a temperature probe, a N₂ gas inlet, and a mechanical stirrer. The reaction vessel was purged with N₂ for at least 15 minutes and then charged with 4-amino-5-fluoro-3-[6-(4-methyl-piperazin-1-yl)-1H-benzimidazol-2-yl]-1H-quinolin-2-one (484 g, 1.23 mol). A solution of D,L-Lactic acid (243.3 g, 1.72 mol of monomer-see the following paragraph), water (339 mL), and ethanol (1211 mL) was prepared and then charged to the reaction flask. Stirring was initiated at a medium rate, and the reaction was heated to an internal temperature of 68-72° C. The internal temperature of the reaction was maintained at 68-72° C. for 1545 minutes and then heating was discontinued. The resulting mixture was filtered through a 10-20 micron frit collecting the filtrate in a 12 L flask. The 12 L flask was equipped with an internal temperature probe, a reflux condenser, an addition funnel, a gas inlet an outlet, and an overhead stirrer. The filtrate was then stirred at a medium rate and heated to reflux (internal temperature of about 78° C.). While maintaining a gentle reflux, ethanol (3,596 mL) was charged to the flask over a period of about 20 minutes. The reaction flask was then cooled to an internal temperature ranging from about 64-70° C. within 15-25 minutes and this temperature was maintained for a period of about 30 minutes. The reactor was inspected for crystals. If no crystals were present, then crystals of the lactic acid salt of 4-amino-5-fluoro-3-[6-(4-methyl-piperazin-1-yl)-1H-benzimidazol-2-yl]-1H-quinolin-2-one (484 mg, 0.1 mole %) were added to the flask, and the reaction was stirred at 64-70° C. for 30 minutes before again inspecting the flask for crystals. Once crystals were present, stirring was reduced to a low rate and the reaction was stirred at 64-70° C. for an additional 90 minutes. The reaction was then cooled to about 0° C. over a period of about 2 hours, and the resulting mixture was filtered through a 25-50 micron fritted filter. The reactor was washed with ethanol (484 mL) and stirred until the internal temperature was about 0° C. The cold ethanol was used to wash the filter cake, and this procedure was repeated 2 more times. The collected solid was dried to a constant weight at 50° C. under vacuum in a vacuum oven yielding 510.7 g (85.7%) of the crystalline yellow lactic acid salt of 4-amino-5-fluoro-3-[6-(4-methyl-piperazin-1-yl)-1H-benzimidazol-2-yl]-1H-quinolin-2-one. A rubber dam or inert conditions were typically used during the filtration process. While the dry solid did not appear to be very hygroscopic, the wet filter cake tends to pick up water and become sticky. Precautions were taken to avoid prolonged exposure of the wet filter cake to the atmosphere.

Commercial lactic acid generally contains about 8-12% w/v water, and contains dimers and trimers in addition to the monomeric lactic acid. The mole ratio of lactic acid dimer to monomer is generally about 1.0:4.7. Commercial grade lactic acid may be used in the process described in the preceding paragraph as the monolactate salt preferentially precipitates from the reaction mixture.

Identification of Metabolites

Two metabolites of 4-amino-5-fluoro-3-[6-(4-methyl-piperazin-1-yl)-1H-benzimidazol-2-yl]-1H-quinolin-2-one (Compound 1) have been identified and characterized in pooled rat plasma from a 2 week toxicology study as described in the references incorporated herein. The two identified metabolites were the piperazine N-oxide compound (Compound 2) and the N-demethylated compound (Compound 3) shown below.

Compound 2

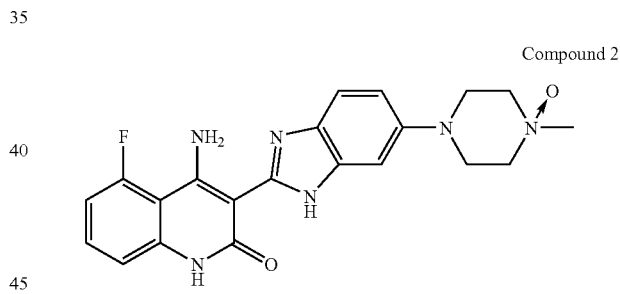

Compound 3

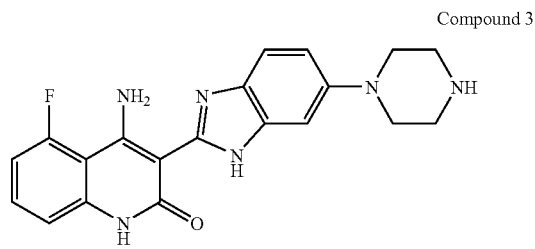

IC₅₀s of Compounds 1-3

The kinase activity of a number of protein tyrosine kinases was measured using the procedures set forth below for Compounds 1-3 to provide the IC$_{50}$ values shown in the following Table.

TABLE

IC$_{50}$s of Compounds 1-3

| Compound | IC$_{50}$ (µM) | | | | | |
|---|---|---|---|---|---|---|
| | VEGFR flt | VEGFR flk1 | bFGFR | PDGFR | Flt3 | c-kit |
| Compound 1 | 0.010 | 0.013 | 0.008 | 0.027 | 0.0001 | 0.0015 |
| Compound 2 | 0.004 | 0.009 | 0.005 | 0.010 | 0.0004 | 0.0002 |
| Compound 3 | 0.019 | 0.012 | 0.019 | 0.037 | 0.0001 | 0.0002 |

Synthesis of 4-Amino-4-fluoro-3-[6-(4-methyl-4-oxidopiperazin-1-yl)-1H-benzimidazol-2-yl]quinolin-2(1H)-one (Compound 2) and 4-Amino-5-fluoro-3-(6-piperazin-1-yl-1H-benzimidazol-2-yl)quinolin-2(1H)-one (Compound 3)

To confirm the structures of the identified metabolites of Compound 1, the metabolites were independently synthesized.

Compound 2, the N-oxide metabolite of Compound 1, was synthesized as shown in the scheme below. Compound 1 was heated in a mixture of ethanol, dimethylacetamide and hydrogen peroxide. Upon completion of the reaction, Compound 2 was isolated by filtration and washed with ethanol. If necessary, the product could be further purified by column chromatography.

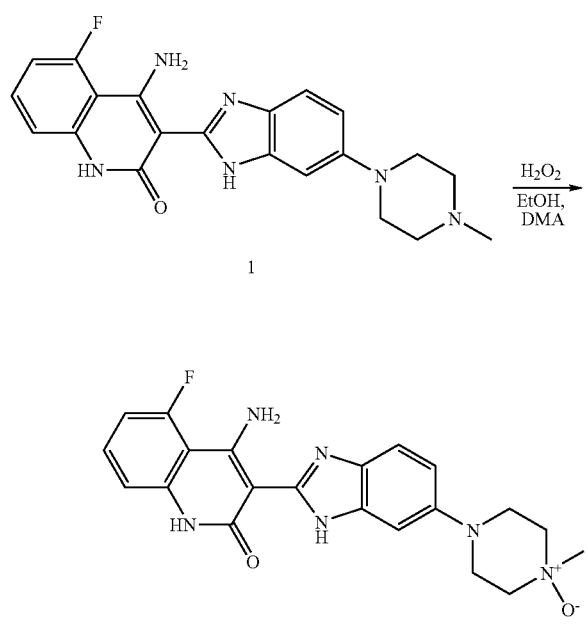

Compound 3, the N-desmethyl metabolite of Compound 1, was synthesized as shown in the scheme below. 5-Chloro-2-nitroaniline was treated with piperazine to yield 4 which was subsequently protected with a butyloxycarbonyl (Boc) group to yield 5. Reduction of the nitro group followed by condensation with 3-ethoxy-3-iminopropionic acid ethyl ester gave 6. Condensation of 6 with 6-fluoroanthranilonitrile using potassium hexamethyldisilazide as the base yielded 7. Crude 7 was treated with aqueous HCl to yield the desired metabolite as a yellow/brown solid after purification.

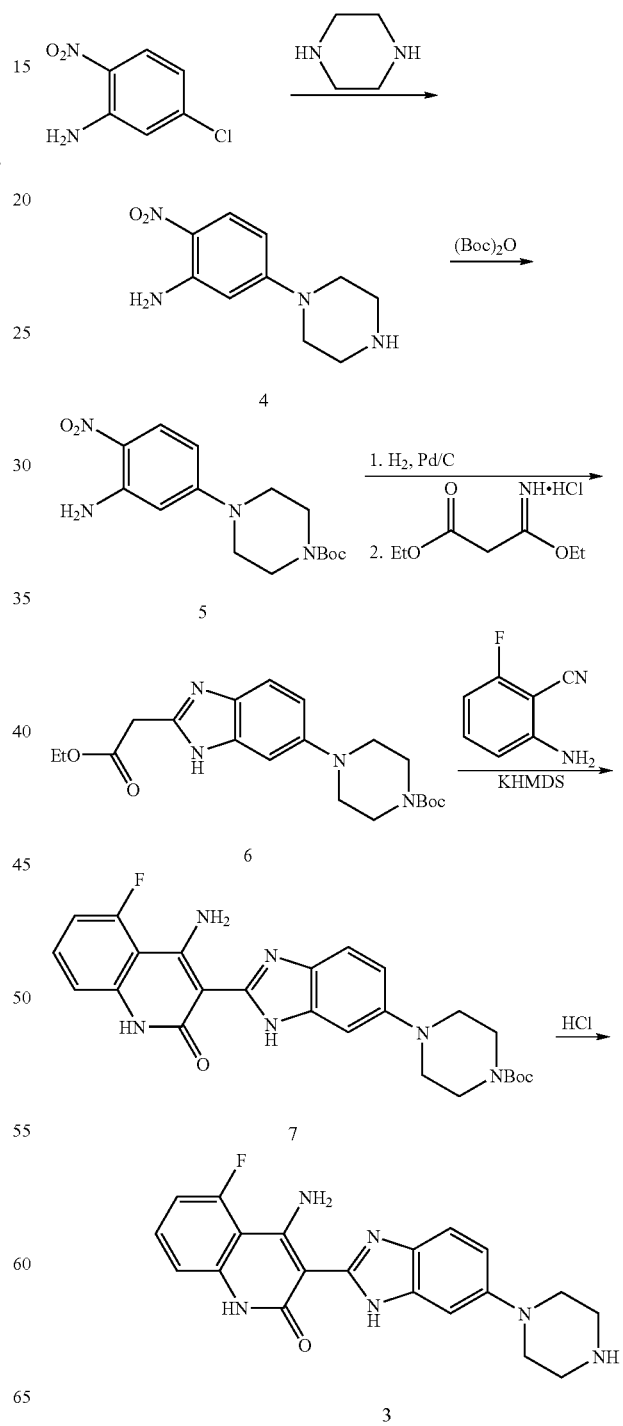

Assay Procedures

Serine/Threonine Kinases

The kinase activity of various protein serine/threonine kinases was measured by providing ATP and a suitable peptide or protein containing a serine or threonine amino acid residue for phosphorylation, and assaying for the transfer of phosphate moiety to the serine or threonine residue. The synthesis and assay activity of a large number of compounds of formula I, II, and III is disclosed in the following references which are all hereby incorporated by reference in their entirety and for all purposes as if specifically set forth herein: U.S. Pat. No. 6,605,617; published U.S. Patent Application No. 2004/0092535; U.S. patent application Ser. No. 10/983,174, filed Nov. 5, 2004; and published U.S. Patent Application No. 2004/0220196. Recombinant proteins containing the kinase domains of GSK-3, RSK-2, PAR-1, NEK-2, and CHK1 enzymes were expressed in Sf9 insect cells using a Baculovirus expression system (InVitrogen) and purified via Glu antibody interaction (for Glu-epitope tagged constructs) or by Metal Ion Chromatography (for $His_6$ (SEQ ID NO: 1) tagged constructs). Cdc2 (GST fusion construct) and cyclin B were co-expressed in Sf9 insect cells using a Baculovirus expression system. Recombinant, active Cdk2/cyclin A is available commercially and was purchased from Upstate Biotechnology. The purified Cdc2 enzyme used in the assay was commercially available, and it may be purchased from New England Bio Labs. For each assay, test compounds were serially diluted in DMSO and then mixed with the appropriate kinase reaction buffer plus 5-10 nM of $^{33}P$ gamma-labeled ATP. The kinase protein and the appropriate biotinylated peptide substrate were added to give a final volume of 150 μL. Reactions were incubated for 3-4 hours at room temperature and then stopped by transferring to a streptavidin-coated white microtiter plate (Thermo Labsystems) containing 100 μL of stop reaction buffer. The stop reaction buffer consists of 50 mM unlabeled ATP and 30 mM EDTA. After 1 hour of incubation, streptavidin plates were washed with PBS, and 200 μL Microscint 20 scintillation fluid was added per well. The plates were sealed and counted using TopCount. The concentration of each compound for 50% inhibition ($IC_{50}$) was calculated employing non-linear regression using XL Fit data analysis software.

The reaction buffer contained 30 mM Tris-HCl$_2$ pH 7.5, 10 mM MgCl$_2$, 2 mM DTT, 4 mM EDTA, 25 mM beta-glycerophosphate, 5 mM MnCl$_2$, 0.01% BSA/PBS, 0.5 μM peptide substrate, and 1 μM unlabeled ATP. GSK-3 enzyme was used at 27 nM, CHK1 at 5 nM, Cdc2 at 1 nM, Cdk2 at 5 nM, and Rsk2 at 0.044 units/mL. For the GSK-3 assay, biotin-CREB peptide (Biotin-SGSGKRREILSRRP(pS)YR-NH$_2$ (SEQ ID NO: 4)) was used. For the CHK1 assay, a biotin-Cdc25c peptide (Biotin-[AHX]SGSGSGLYRSPSMPENLNRPR[CONH$_2$] (SEQ ID NO: 5)) was used. For the Cdc2 and the Cdk2 assays, a biotin-Histone H1 peptide ([IcBiotin]GGGG-PKTPKKAKKL[CONH$_2$] (SEQ ID NO: 6)) was used. In the Rsk2 assay, a biotin-p70 peptide, 15 mM MgCl$_2$, 1 mM DTT, 5 mM EDTA, 2.7 μM PKC inhibitor peptide, and 2.7 μM PKA inhibitor peptide were used.

Tyrosine Kinases

The kinase activity of a number of protein tyrosine kinases was measured by providing ATP and an appropriate peptide or protein containing a tyrosine amino acid residue for phosphorylation, and assaying for the transfer of phosphate moiety to the tyrosine residue. Recombinant proteins corresponding to the cytoplasmic domains of the FLT-1 (VEGFR1), VEGFR2, VEGFR3, Tie-2, PDGFRα, PDGFRβ, and FGFR1 receptors were expressed in Sf9 insect cells using Baculovirus expression system (InVitrogen) and may be purified via Glu antibody interaction (for Glu-epitope tagged constructs) or by Metal Ion Chromatography (for $His_8$ (SEQ ID NO: 1) tagged constructs). For each assay, test compounds were serially diluted in DMSO and then mixed with an appropriate kinase reaction buffer plus ATP. Kinase protein and an appropriate biotinylated peptide substrate were added to give a final volume of 50-100 μL, reactions were incubated for 1-3 hours at room temperature and then stopped by addition of 25-50 μL of 45 mM EDTA, 50 mM Hepes pH 7.5. The stopped reaction mixture (75 μL) was transferred to a streptavidin-coated microtiter plate (Boehringer Mannheim) and incubated for 1 hour. Phosphorylated peptide product was measured with the DELFIA time-resolved fluorescence system (Wallac or PE Biosciences), using a Europium labeled anti-phosphotyrosine antibody PT66 with the modification that the DELFIA assay buffer was supplemented with 1 mM MgCl$_2$ for the antibody dilution. Time resolved fluorescence was read on a Wallac 1232 DELFIA fluorometer or a PE Victor II multiple signal reader. The concentration of each compound for 50% inhibition ($IC_{50}$) was calculated employing non-linear regression using XL Fit data analysis software.

FLT-1, VEGFR2, VEGFR3, Tie-2, and FGFR1 kinases were assayed in 50 mM Hepes pH 7.0, 2 mM MgCl$_2$, 10 mM MnCl$_2$, 1 mM NaF, 1 mM DTT, 1 mg/mL BSA, 2 μM ATP, and 0.20-0.50 μM corresponding biotinylated peptide substrate. FLT-1, VEGFR2, VEGFR3, Tie-2, and FGFR1 kinases were added at 0.1 μg/mL, 0.05 μg/mL, or 0.1 μg/mL respectively. For the PDGFR kinase assay, 120 μg/mL enzyme with the same buffer conditions as above was used except for changing ATP and peptide substrate concentrations to 1.4 μM ATP, and 0.25 μM biotin-GGLFDDPSYVN-VQNL-NH$_2$ (SEQ ID NO: 2) peptide substrate.

Recombinant and active tyrosine kinases Fyn, and Lck are available commercially and were purchased from Upstate Biotechnology. For each assay, test compounds were serially diluted in DMSO and then mixed with an appropriate kinase reaction buffer plus 10 nM $^{33}P$ gamma-labeled ATP. The kinase protein and the appropriate biotinylated peptide substrate were added to give a final volume of 150 μL. Reactions were incubated for 3-4 hours at room temperature and then stopped by transferring to a streptavidin-coated white microtiter plate (Thermo Labsystems) containing 100 μL of stop reaction buffer of 100 mM EDTA and 50 μM unlabeled ATP. After 1 hour incubation, the streptavidin plates were washed with PBS and 200 μL Microscint 20 scintillation fluid was added per well. The plates were sealed and counted using TopCount. The concentration of each compound for 50% inhibition ($IC_{50}$) was calculated employing non-linear regression using XL Fit data analysis software.

The kinase reaction buffer for Fyn, Lck, and c-ABL contained 50 mM Tris-HCl pH 7.5, 15 mM MgCl$_2$, 30 mM MnCl$_2$, 2 mM DTT, 2 mM EDTA, 25 mM beta-glycerol phosphate, 0.01% BSA/PBS, 0.5 μM of the appropriate peptide substrate (biotinylated Src peptide substrate: biotin-GGGGKVEKIGEGTYGVVYK-NH$_2$ (SEQ ID NO: 3) for Fyn and Lck), 1 μM unlabeled ATP, and 1 nM kinase.

The kinase activity of c-Kit and FLT-3 were measured by providing ATP and a peptide or protein containing a tyrosine amino acid residue for phosphorylation, and assaying for the transfer of phosphate moiety to the tyrosine residue. Recombinant proteins corresponding to the cytoplasmic domains of the c-Kit and FLT-3 receptors were purchased (Proquinase). For testing, an exemplary compound, for example 4-amino-5-fluoro-3-[6-(4-methylpiperazin-1-yl)-1H-benzimidazol-2-yl]quinolin-2(1H)-one, was diluted in DMSO and then mixed with the kinase reaction buffer described below plus ATP. The kinase protein (c-Kit or FLT-3) and the biotinylated peptide substrate (biotin-GGLFDDPSYVNVQNL-NH$_2$ (SEQ ID NO: 2)) were added to give a final volume of 100 µL. These reactions were incubated for 2 hours at room temperature and then stopped by addition of 50 µL of 45 mM EDTA, 50 mM HEPES, pH 7.5. The stopped reaction mixture (75 µL) was transferred to a streptavidin-coated microtiter plate (Boehringer Mannheim) and incubated for 1 hour. Phosphorylated peptide product was measured with the DELPHIA time-resolved fluorescence system (Wallac or PE Biosciences), using a Europium-labeled anti-phosphotyrosine antibody, PT66, with the modification that the DELFIA assay buffer was supplemented with 1 mM MgCl$_2$ for the antibody dilution. Time resolved fluorescence values were determined on a Wallac 1232 DELFIA fluorometer or a PE Victor II multiple signal reader. The concentration of each compound for 50% inhibition (IC$_{50}$) was calculated employing non-linear regression using XL Fit data analysis software.

FLT-3 and c-Kit kinases were assayed in 50 mM Hepes pH 7.5, 1 mM NaF, 2 mM MgCl$_2$, 10 mM MnCl$_2$ and 1 mg/mL BSA, 8 µM ATP and 1 µM of corresponding biotinylated peptide substrate (biotin-GGLFDDPSYVNVQNL-NH2 (SEQ ID NO: 2)). The concentration of FLT-3 and c-Kit kinases were assayed at 2 nM.

Real-Time and Comprehensive Imaging Evaluation of 4-Amino-5-fluoro-3-[6-(4-methylpiperazin-1-yl)-1H-benzimidazol-2-yl]quinolin-2(1H)-one Efficacy in a Preclinical Multiple Myeloma Model Multiple myeloma (MM), a B-cell neoplasm characterized by clonal expansion of plasma cells in the hematopoietic bone marrow, remains a fatal hematological malignancy due to development of intrinsic and acquired drug resistance despite introduction of conventional high-dosage chemotherapy. It has been demonstrated that bone marrow microenvironment, where MM cells preferentially home and grow, plays a crucial role in developing resistance to conventional and novel therapies for MM. Therefore, molecularly targeted agents targeting not only the MM cells but also MM cell-bone marrow microenvironment interaction offer a potential opportunity to treat MM. Recent advances in understanding the molecular pathology of MM have provided novel therapeutic targets for treatment of this disease. The ectopically expressed and deregulated FGFR-3, which occur in approximately 15% MM patients resulting from t(4;14) chromosomal translocation and confers a particularly poor prognosis in clinic, has become an attractive therapeutic target for MM.

4-Amino-5-fluoro-3-[6-(4-methylpiperazin-1-yl)-1H-benzimidazol-2-yl]quinolin-2(1H)-one (Compound 1) is a small molecule inhibitor targeting to multiple receptor tyrosine kinases including VEGFR-2 and PDGFR (IC$_{50}$s ~20 nM in kinase assays) and FGFR-3 (IC$_{50}$ ~5 nM in kinase assays). It has been demonstrated that 4-amino-5-fluoro-3-[6-(4-methylpiperazin-1-yl)-1H-benzimidazol-2-yl]quinolin-2(1H)-one inhibits FGFR-3 autophosphorylation and cell proliferation in FGFR-3 mutant MM cells in vitro (S, Trudel et al.; Blood; in press). To evaluate the antimyeloma efficacy of 4-amino-5-fluoro-3-[6-(4-methylpiperazin-1-yl)-1H-benzimidazol-2-yl]quinolin-2(1H)-one, an in vivo preclinical MM model was developed in which multi-organ MM lesions developed after tail vein i.v. injection of human KMS-11-luc cells expressing mutant FGFR-3 (Y373C) stably transfected with a construct of luciferase. Bioluminescent imaging (BLI) was employed to non-invasively monitor the in vivo growth and metastasis of KMS-11-luc MM tumors. Early detection and serial comprehensive monitoring growth of metastatic lesions was successfully captured by BLI with this model.

Nearly all KMS-11-luc tumor cell-injected animals were found to develop MM lesions at as early as day 26, which were mainly localized in spine, skull and pelvis resulting in frequent development of paralysis in this model. The antimyeloma efficacy of 4-amino-5-fluoro-3-[6-(4-methylpiperazin-1-yl)-1H-benzimidazol-2-yl]quinolin-2(1H)-one in this i.v. injected in vivo KMS-11-luc MM model was investigated and it was found that daily oral administration of 4-amino-5-fluoro-3-[6-(4-methylpiperazin-1-yl)-1H-benzimidazol-2-yl]quinolin-2(1H)-one at 20 mg/kg, a dose that was demonstrated to inhibit phosphorylation of ERK in KMS-11-luc tumors in vivo, resulted in a significant inhibition of KMS-11 tumor growth, as detected by serial BLI imaging. Furthermore, the antitumor growth activity of 4-amino-5-fluoro-3-[6-(4-methyl piperazin-1-yl)-1H-benzimidazol-2-yl]quinolin-2(1H)-one translated to a significant improvement in the animal survival rate compared to vehicle treatment. These studies provide further preclinical basis for clinical trials of 4-amino-5-fluoro-3-[6-(4-methylpiperazin-1-yl)-1H-benzimidazol-2-yl]quinolin-2(1H)-one in MM patients and warrant further evaluation of 4-amino-5-fluoro-3-[6-(4-methylpiperazin-1-yl)-1H-benzimidazol-2-yl]quinolin-2(1H)-one in combination therapy with conventional or other molecularly targeted agents in this KMS-11-luc in vivo model.

Method

A cohort of 18 female (about 8 week old) immunodeficient SCID-beige mice were obtained from The Jackson laboratory (Bar Harbor, Me.) and were housed in a barrier facility in sterile filter-top cages with 12 hour light/dark cycles. All experiments were conducted in a facility accredited by the Association for Assessment and Accreditation of Laboratory Animal Care International and in accordance with all guidelines of the Institutional Animal Care and Use Committee and the Guide for The Care and Use of Laboratory Animals (National Research Council). KMS-11-luc MM cells harboring FGFR-3 mutants (Y373C) were cultured in Iscove's Media +10% FBS+L-glutamine and passed twice/week in a range of 1:2 to 1:4. Cells were implanted by intravenous injection into the tail vein at 10×10$^6$ cells per 100 µL HBSS per mouse. Mice were irradiated at 3 GY (3.2 minutes) on the day of cell implantation. Animals received daily oral treatment of 20 mg/kg 4-amino-5-fluoro-3-[6-(4-methylpiperazin-1-yl)-1H-benzimidazol-2-yl]quinolin-2(1H)-one or vehicle (n=9 each group) starting at 48 hours after the KOM11-luc cells were injected. Bioluminescent images (BLI) were obtained using an IVIS Imaging System (Xenogen) that included a highly sensitive, cooled CCD camera mounted in a light-tight camera box. Images and measurements of bioluminescent signals, as quantified by photons/second, were acquired at day 8 and once a week thereafter. Animal body weights were monitored twice a week and clinical observations were recorded daily. In accordance with animal care regulation and guidelines, mice were sacrificed by CO$_2$ inhalation in the event of paralysis or major compromise in their quality of life.

Results

At day 8 after KMS-11-luc cells were intravenously injected into SCID-beige mice, whole body imaging demonstrated development of cell growth and possibly MM lesions mainly localized in extraskeletal regions including lung, liver and spleen. Typical diffuse multiple skeletal lesions including skull, pelvis and spine were clearly observed in the majority of mice at between day 41 and day 48 as seen in the BLI images of FIG. 1, which was associated with hind limb paralysis, resulting in sacrifice of mice according to protocol.

Figure 2:
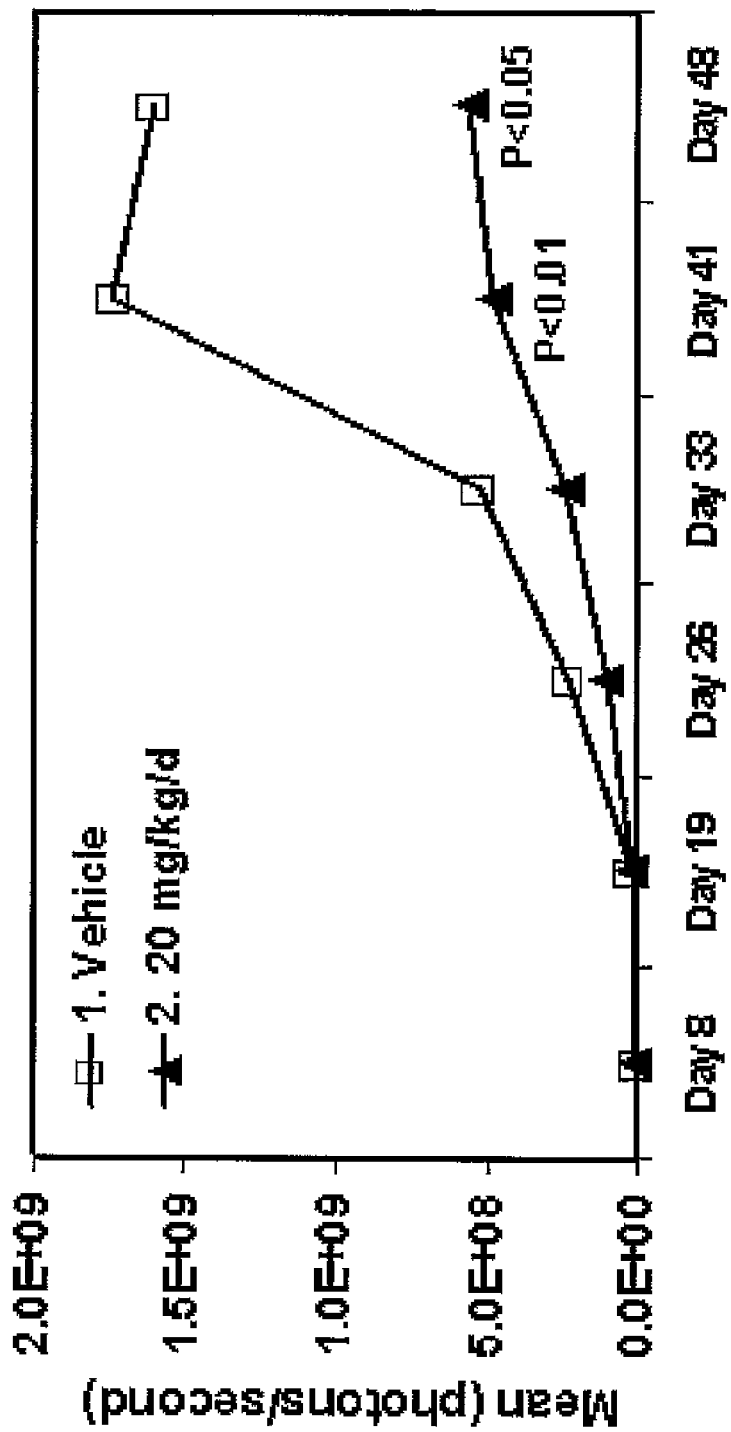
FIG. 2 is a graph showing that SCID-beige mice injected with KMS-11-luc cells and treated with 4-amino-5-fluoro-3-[6-(4-methylpiperazin-1-yl)-1H-benzimidazol-2-yl]quinolin-2(1H)-one (20 mg/kg/d) exhibited a significantly lower mean photon count than those treated with vehicle.
Figure 3:
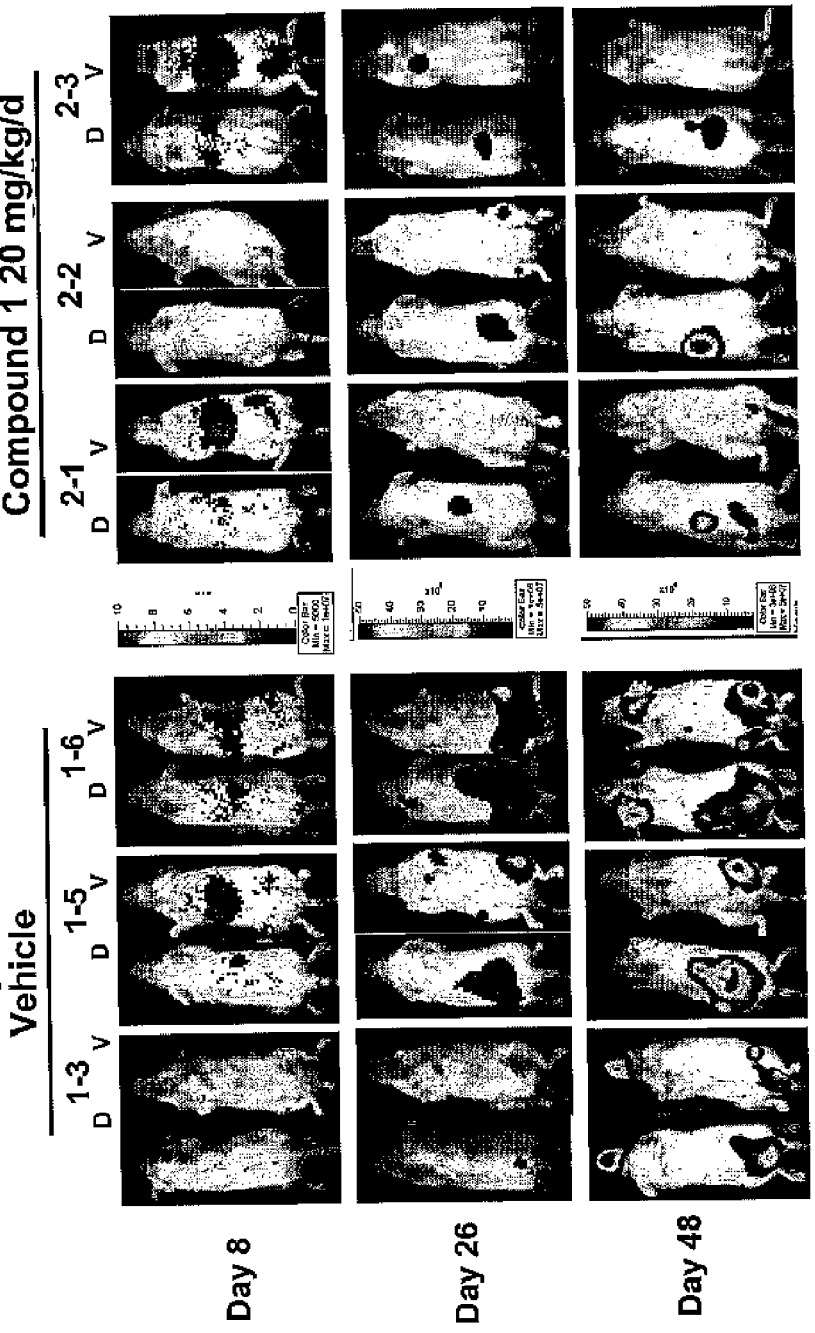
FIG. 3 is a scanned image of whole body BLIs obtained using an IVIS Imaging System (Xenogen) of SCID-beige mice after intravenous injection with KMS-11-luc cells. The BLIs on the left are of mice treated with vehicle and the BLIs on the right are of mice treated with 4-amino-5-fluoro-3-[6-(4-methylpiperazin-1-yl)-1H-benzimidazol-2-yl]quinolin-2(1H)-one (Compound, 20 mg/kg/d).

The anti myeloma efficacy of 4-amino-5-fluoro-3-[6-(4-methylpiperazin-1-yl)-1H-benzimidazol-2-yl]quinolin-2(1H)-one was tested in KMS-11-luc in this in vivo model. Mice started to receive daily oral treatment of 58 at 20 mg/kg at 48 hours after the KMS-11-luc cells were injected. Comprehensive and serial monitoring of photon counts in each animal was performed on a weekly base schedule. A significant lower mean photon count in 4-amino-5-fluoro-3-[6-(4-methyl piperazin-1-yl)-1H-benzimidazol-2-yl]quinolin-2(1H)-one treated group was demonstrated compared to vehicle treatment as shown in FIG. 2. This was easily observed by comparison of the whole body BLI images taken of mice injected with KMS-11-luc treated with vehicle and those treated with 4-amino-5-fluoro-3-[6-(4-methylpiperazin-1-yl)-1H-benzimidazol-2-yl]quinolin-2(1H)-one as shown in FIG. 3.

Reduction of photon count in mice treated with 4-amino-5-fluoro-3-[6-(4-methylpiperazin-1-yl)-1H-benzimidazol-2-yl]quinolin-2(1H)-one treated was well reflected by a significant increase in the survival time compared to mice treated with vehicle. At day 91, 5 out of 9 animals in those mice treated with 4-amino-5-fluoro-3-[6-(4-methylpiperazin-1-yl)-1H-benzimidazol-2-yl]quinolin-2(1H)-one remained alive with overall healthy conditions. In contrast, most animals in the vehicle-treated group were sacrificed around day 50. Furthermore, mice treated with 4-amino-5-fluoro-3-[6-(4-methylpiperazin-1-yl)-1H-benzimidazol-2-yl]quinolin-2(1H)-one, tolerated this treatment well for the long period of this study. Because of the obvious improvement in the survival time of mice treated with 4-amino-5-fluoro-3-[6-(4-methylpiperazin-1-yl)-1H-benzimidazol-2-yl]quinolin-2(1H)-one, the study was terminated at day 91 for practical considerations.

Various studies with respect to kinase inhibition in general, inhibition of FGFR3, and treatment of cancers including multiple myeloma with 4-amino-5-fluoro-3-[6-(4-methylpiperazin-1-yl)-1H-benzimidazol-2-yl]quinolin-2(1H)-one are set forth in published U.S. Patent Application No. 2004/0092535, and U.S. patent application Ser. No. 10/983,174, U.S. Patent Application No. 2004/0220196, and U.S. Pat. No. 6,605,617. Therefore, each of these references is hereby incorporated by reference in its entirety and for all purposes as if fully set forth herein.

Activity of 4-amino-5-fluoro-3-[6-(4-methylpiperazin-1-yl)-1H-benzimidazol-2-yl]quinolin-2(1H)-one (Compound 1) in Experimental Tumor Xenograft Models of Human AML 4-Amino-5-fluoro-3-[6-(4-methyl piperazin-1-yl)-1H-benzimidazol-2-yl]quinolin-2(1H)-one (Compound 1) is a novel, orally active, multitargeted small molecule, that exhibits potent activity against FLT3 kinase and Class III, IV, and V RTKs involved in endothelial and tumor cell proliferation. Given the relevance of FLT3 mutations in acute myelogenous leukemia (AML), Compound 1 was tested on two human leukemic cell lines with differing FLT3 mutational status (MV4;11 FLT3 ITD vs. RS4;11 FLT3 WT). Antiproliferative activity of Compound 1 against MV4;11 was ~24-fold greater compared to RS4;11, indicating more potent inhibition of constitutively activated FLT3. Dose-dependent modulation of receptor phosphorylation and downstream signaling (STAT5 and ERK/MAPK) in MV4;11 cells with Compound 1 confirmed molecular mechanism of action. Target modulation of pFLT3, pERK in MV4;11 tumors was achieved at biologically active doses of Compound 1. Tumor regressions and eradication of AML cells from the bone marrow (BM) were demonstrated in subcutaneous and BM engraftment leukemic xenograft models. Tumor responses were characterized by decreased cellular proliferation and positive immunohistochemical staining for active caspase-3 and cleaved PARP, suggesting cell death was mediated via apoptosis. These data support the clinical evaluation of Compound 1 in AML.

Cell Lines

Human MV4;11 (FLT3 ITD) and RS4;11 (FLT3 WT) leukemic cells were obtained from American Tissue Culture Collection (Rockville, Md.) 24-26. MV4;11 cells were grown in Iscoves modified Dulbecco medium (IMBM) supplemented with 10% fetal bovine serum (FBS, Gibco Life Technologies, Gaithersburg, Md.) containing 4 mM L-glutamine, 5 ng/ml granulocytemacrophage colony stimulating factor (GM-CSF, R&D Systems, Minneapolis, Minn.) and 1% Penicillin and Streptomycin. RS4;11 were grown in RPMI-1640 media containing 10% FBS, 1 mM sodium pyruvate and 10 mM HEPES (pH 7.4), Cells were grown as suspension cultures and maintained in a humidified atmosphere at 37° C. and 5% $CO_2$.

Kinase Assays

In vitro FLT3 kinase assays were run with 2 nM FLT3 enzyme (Upstate Biotechnology, Charlottesville, Va.) in the presence of 8 μM ATP and serial dilutions of Compound 1. Phosphorylated peptide substrate at a final concentration of 1 μM was incubated with a Europium-labeled anti-phosphotyrosine antibody (PT66) (Perkin Elmer Life Sciences, Boston, Mass.). The Europium was detected using time resolved fluorescence. The $IC_{50}$ was calculated using nonlinear regression.

Proliferation Assays

Cells were plated in 96-well microtiter plates (10,000 cells/well) and serial dilutions of Compound 1 were added. RS4;11 cells were stimulated with FLT3 ligand (100 ng/ml, R&D Systems, Minneapolis, Minn.). At the end of the incubation period (72 h at 37° C.), cell viability was determined by the MTS assay (Promega, Madison, Wis.). $EC_{50}$ values were calculated using nonlinear regression, and defined as the concentration needed for a 50% reduction in absorbance of treated vs. untreated control cells.

Immunoprecipitation and Wester Blot Analysis

For in vitro experiments, MV4;11 and RS4;11 cells were treated with Compound 1 for 3 hours. RS4;11 cells were stimulated with FLT3 ligand (100 ng/mL) for 15 minutes after incubation with Compound 1. After incubation with drug, cells were harvested, washed with ice-cold PBS and lysed with RIPA buffer (1% Nonidet P-40, 0.5% sodium deoxycholate, 0.1% Sodium dodecylsulphate in 1× phosphate buffered saline, pH 7.2) containing protease inhibitors (Roche Molecular Biochemicals, Indianapolis, Ind.) and phosphatase inhibitors (Sigma, St. Louis, Mo.). For in vivo target modulation analyses, resected tumors were flash frozen, pulverized and stored at −70° C. prior to lysis with 150 mM NaCl, 1.5 mM $MgCl_2$, 50 mM Hepes, pH 7.5, 10% glycerol, 1.0% Triton X-100, 1 mM EGTA, 50 mM NaF, 1 mM $Na_3VO_4$, 2 mM Pefabloc (Roche), and complete protease inhibitor cocktail (Roche). Protein content of the lysates was determined using the BCA assay (Bio-Rad, Hercules, Calif.). Western blot analysis for pERK was performed with a mouse antibody to pERK (1:1000, Cell Signaling, Beverly, Mass.) and incubated at 4° C. overnight. Total ERK level was evaluated by re-probing with antibody against total ERK (Cell Signaling). The membranes were then incubated for 1 hour at RT with 1:5000 horseradish peroxidase-conjugated anti-rabbit IgG (Jackson Immunoresearch, West Grove, Pa.). For immunoprecipitation to detect FLT3, equal amounts of proteins (500 μg for STAT5; 1000 μg for FLT3) were incubated with antibodies against either human FLT3 or STAT5 (Santa Cruz Biotechnology, Santa Cruz, Calif.) overnight at 4° C. and with protein A-agarose for 2 hours at 4° C. FLT3 or STAT5 phosphorylation was measured by probing with an anti-phosphotyrosine antibody (anti-pFLT3 antibody from Cell Signaling, and anti-pSTAT5 antibody from Upstate). Proteins were detected using enhanced chemiluminescence (ECL; Amersham Biosciences, Buckinghamshire, England) and visualized after exposure to Kodak film. Scanning densitometry was performed to quantify band intensities. To verify equal loading, blots were stripped and re-probed with antibodies to either anti-FLT3 (Santa Cruz Biotechnology) or anti-STAT5 (BD Biosciences) to measure total FLT3 or STAT5 protein, respectively. The amount of pFLT3, pERK or pSTAT5 was normalized to total FLT3, ERK or STAT5 protein levels, and compared to vehicle or untreated controls.

Flow Cytometric Assays

MV4;11 cells were treated with Compound 1 for 3 hours under serum-starved conditions (overnight in OptiMEM media). For detection of pSTAT5, cells were fixed with 1% formaldehyde, and permeabilized with 90% ice-cold methanol. Permeabilized cells ($0.5-1\times10^6$) were incubated with anti-pSTAT5 antibody (Cell Signaling) for 30 minutes. Purified rabbit IgG (Oncogene, San Diego, Calif.) at the same concentration was used as isotype control. Secondary antibody was a PE-conjugated goat F(ab')2 anti-rabbit IgG (Jackson Immunoresearch). Samples were stored at 4° C. in the dark prior to analyses using a FACScan flow cytometer (Becton Dickinson, San Jose, Calif.). Mean fluorescent intensity (MFI) was determined for pSTAT5 staining using CellQuest software (Becton Dickinson) and the specific MFI was the difference from the MFI of isotype control antibody.

For processing of bone marrow (BM) cells from the mouse MV4;11 engraftment model, femurs were purged with cold saline and red blood cells lysed with FACS lysis buffer (Becton Dickinson). Percent engraftment of human leukemic cells in mouse BM was determined by staining with anti-human HLA-A,B,C-FITC (vs. isotype-matched antibody-FITC control) (BD Pharmingen).

VEGF ELISA

MV4,11 cells were cultured in 10% FBS containing media with various concentrations (0-1 μM) of Compound 1 for 48 hours. The supernatants were collected after centrifugation, and VEGF levels were measured by ELISA (R&D Systems, Minneapolis, Minn.). Protein concentrations were determined using the BIO-RAD protein assay (Hercules, Calif.) and results were normalized to protein concentration.

In Vivo Efficacy Studies

Female SCID-NOD mice (4-6 week-old, 18-22 g) were obtained from Charles River (Wilmington, Mass.) and acclimated for 1 week in pathogen-free enclosure prior to start of study. Animals received sterile rodent chow and water ad libitum and were housed in sterile filter-top cages with 12 hour light/dark cycles. All experiments were under the guidelines of the Association for Assessment and Accreditation of Laboratory Animal Care International.

Subcutaneous Model

MV4;11 and RS4;11 cells were passaged from subcutaneous (s.c.) tumors in SCID-NOD mice. Cells ($5\times10^6$ cells/mouse) were reconstituted with 50% Matrigel (Becton Dickinson) and implanted s.c. into the right flank of SCID-NOD mice. Treatments were initiated when tumors were 200-1000 mm$^3$, as outlined in specific study designs. Mice were randomly assigned into cohorts (typically 10 mice/group for efficacy studies and 3-5 mice/group for pharmacodynamic (PD) studies). Compound 1 was administered as a solution via oral gavage. Tumor volumes and body weights were assessed 2-3 times weekly. Caliper measurements of tumors were converted into mean tumor volume using the formula: 112 (length×[width]2). Percent tumor growth inhibition (TGI) was compared with vehicle-treated mice. Response rates were defined as complete responses OR (no palpable tumor) or partial responses PR (50-99% shrinkage) compared to tumor volume at treatment initiation.

Intravenous Bone Marrow (BM) Engraftment Model

SCID-NOD mice were irradiated (3 Gy) prior to tail vein injection of $1\times10^7$ MV4;11 cells in 0.2 ml saline. Compound 1 or vehicle treatments were initiated 3 weeks post-cell inoculation. Mice were monitored daily and were euthanized when moribund or early signs of loss of hind limb motility. Increased life span (ILS) of treated mice was calculated as a percent increase in median survival time (MST) vs. vehicle treated control mice.

Target Modulation In Vivo

MV4;11 s.c.; tumors in SCID-NOD mice (n=3 mice/group) were staged at 300 mm$^3$ and treatments consisted of either vehicle or Compound 1 was administered orally at 10 mg/kg for 5 days. To characterize the PD properties of Compound 1, tumor samples were collected at various times (N=3 mice/timepoint) following Compound 1 dosing.

Immunohistochemistry

Resected tumors were placed in 10% neutral buffered formalin overnight at RT, transferred to 70% ethanol and processed for paraffin embedding using a Thermo Electron Excelsior tissue processor (Pittsburgh, Pa.). Bone (femur) samples were decalcified (Protocol™, Fisher Diagnostics, Middletown, Va.). Paraffin blocks were sectioned to 4 μm thickness and placed on positively charged glass slides. Tissues were stained using a Discovery automated slide machine (Ventana Medical Systems, Tucson, Ariz.). The slides were treated with citrate buffer (pH 6.0) in a pressured steamer to retrieve antigen for Ki-67, pERK and PARP staining, and caspase-3 was retrieved by Ventana reagent CC1. The primary antibodies used were Ki-67 (1:750 dilution, NovoCastra Laboratories, UK), pERK (1:100 dilution, Biosource, Camarillo, Calif.), anti-human mitochondria (1:200, Chemicon, Temecula, Calif.), cleaved caspase-3 (1:200, Cell Signaling) and cleaved PARP (1:100, Biosource). Secondary antibody was a goat anti-rabbit F (ab')2 biotinylated antibody, 1:100 dilution (Jackson ImmunoResearch). Slides were counterstained with hematoxylin and the mounted with a cover slip. General tissue morphology was also evaluated using hemtoxylin and eosin staining.

Statistical Analyses

Linear regression was performed using Microsoft Excel (Redmond, Wash.). Student's t-test was used to measure statistical significance between two treatment groups. Multiple comparisons were done using one-way analysis of variance (ANOVA), and post-tests comparing different treatment means were done using Student-Newman Keul's test (SigmaStat, San Rafael, Calif.). For survival studies, log rank test was used to determine significance between survival curves of various treatments vs. vehicle groups (Prism, San Diego, Calif.). Mice sacrificed with normal health status at termination of study were considered long-term survivors and censored in this analysis. Differences were considered statistically significant at $p<0.05$.

Results

Compound 1 Demonstrates Potent Inhibition of FLT3 Kinase Activity

The specificity of Compound 1 was tested against a diverse panel of RTKs using ATP-competitive binding assays with purified enzymes as described above. Compound 1 was found to be highly potent against FLT3 (1 nM) with nanomolar activity against c-KIT (2 nM), VEGFR1/2/3 (10 nM); FGFR1/3 (8 nM); PDGFRβ (27 nM) and CSF-1R (36 nM) (See the following Table). To confirm selectivity against Class III, IV and V RTKs, Compound 1 was tested against other kinases in the PI3K/Akt and MAPK(K) pathways and was found to have negligible activity ($IC_{50}$>10 µM) (See the following Table).

TABLE

Activity of 4-Amino-5-fluoro-3-[6-(4-methylpiperazin-1-yl)-1H-benzimidazol-2-yl]quinolin-2(1H)-one Against Various RTKs

| RTK | $IC_{50}$ (µm) |
|---|---|
| FLT3 | <0.001 |
| c-KIT | 0.002 |
| CSF-1R | 0.036 |
| FGFR1 | 0.008 |
| FGFR3 | 0.009 |
| VEGFR1/Flt1 | 0.01 |
| VEGFR2/Flk1 | 0.013 |
| VEGFR3/Flt4 | 0.008 |
| PDGFRβ | 0.027 |
| PDGFRα | 0.21 |
| INSR | 2 |
| EGFR1 | 2 |
| c-MET | >3 |
| EphA2 | 4 |
| TIE2 | 4 |
| IGFR1, HER2, PI-3K. Akt1/3, Raf, ERK-1/2, MEK, p38-α, β, γ | >10 |

The in vitro RTK assays used to prepare the above table were run with various dilutions of Compound 1 in the presence of purified enzymes and ATP as described above. Phopshoylated peptide substrates (1 µM) were incubated with Europium-labeled anti-phosphospecific antibodies and Europium was detected using time-resolved fluorescence.

Potent Antiproliferative Effects of Compound 1 on MV4;11 (FLT3 ITD) Cells

Figure 5:
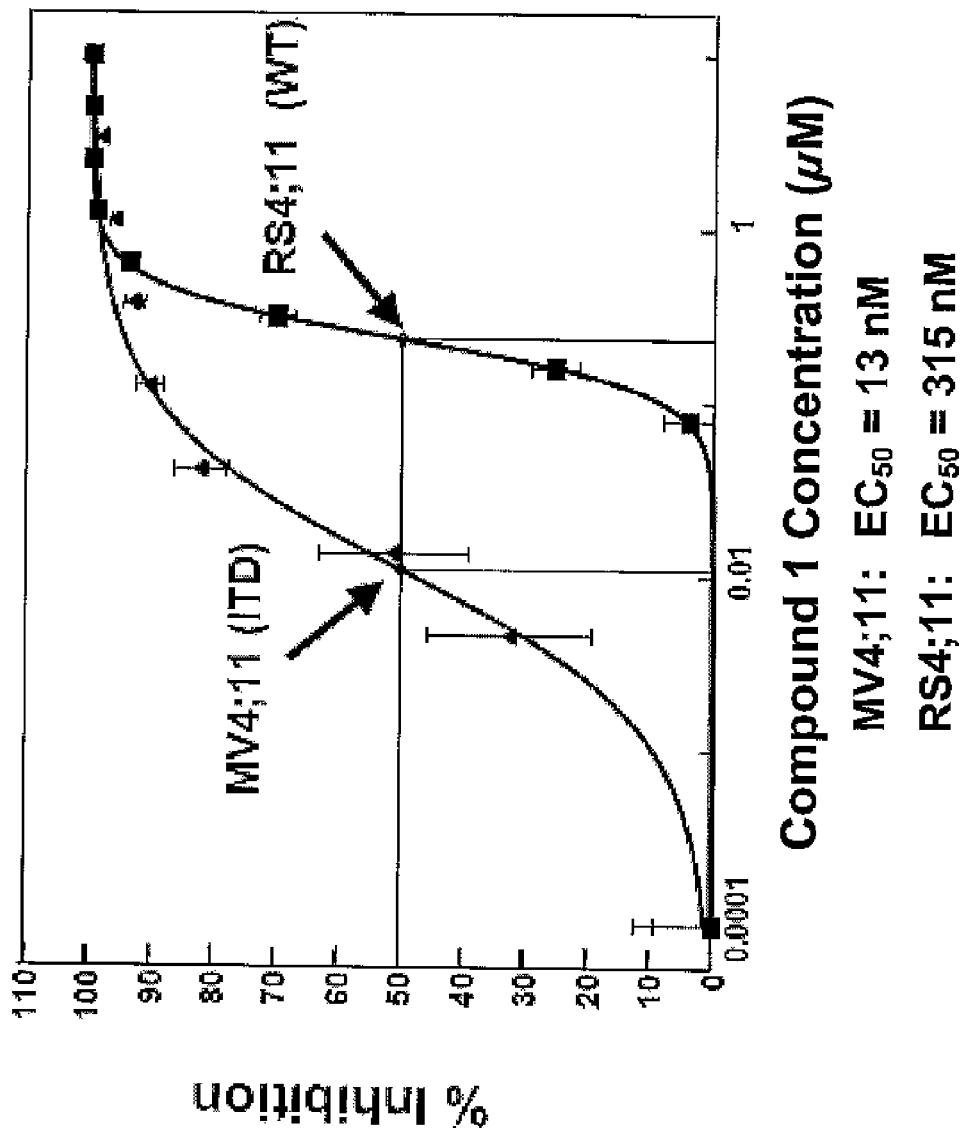

To determine whether inhibition of FLT3 translates into growth inhibition in vitro, the activity of Compound 1 was tested against MV4;11 and RS4;11 cells using the MTS assay (FIG. 5). Compound 1 potently inhibited proliferation of MV4;11 cells in a dose-dependent manner with $EC_{50}$=13 nM. Although similar concentration-dependent effects on proliferation were observed with RS4;11 cells, they were approximately 24-fold less sensitive to Compound 1 ($EC_{50}$=315 nM). Antiproliferative effect of Compound 1 was also tested on the FLT3 ITD mutant cells, MOLM13 and MOLM14 with $EC_{50}$ concentrations similar to those seen with MV4;11 (EC50~6 nM) (data not shown). These data suggest that Compound 1 is active on both FLT3 ITD and WT leukemic cells, with the constitutively active receptor being more sensitive to inhibition (FIG. 5).

In Vitro Effects of Compound 1 on FLT3-Mediated Signaling in Leukemic Cells

The in vitro cellular activity of Compound 1 was investigated on two human leukemic cell lines MV4;11 and RS4;11 with contrasting FLT3 mutational status (confirmed using RT-PCR, data not shown). MV4;11 cells have an internal tandem duplication mutation (ITD) in the FLT3 receptor, resulting in constitutively activated FLT3. Levis M. et al. *Blood*, 99:3885-3891 (2002); O'Farrell A. M. et al., *Blood*, 101:3597-3605 (2003). This activation results in autophosphorylation of FLT3 in the absence of exogenous ligand stimulation (FIG. 6, lane 1). Serum-deprived MV4;11 cells were treated with Compound 1 for 3 hours, and direct effects on FLT3 receptor activation was determined by analysis of its phosphorylation status. Exposure of MV4;11 cells to increasing concentrations of Compound 1 potently inhibited pFLT3 in a dosedependent manner with $EC_{50}$ between 1-10 nM (FIG. 6).

While FLT3 ITDs are prevalent in approximately 20% of AML patient blasts, most acute leukemias express WT FLT3. The effects of Compound 1 on leukemic RS4;11 cells were also investigated (FLT3 WT) (FIG. 7) following exogenous FLT3 ligand (100 ng/ml, 15 minutes) to activate FLT3 receptor phosphorylation (FIG. 7, lane 1 vs. 2). Compound 1 diminished pFLT3 levels in RS4;11 cells (FIG. 7). However, comparatively, higher concentrations were required for modulation of WT FLT3 vs. ITD. Complete inhibition was obtained with concentrations >0.5 µM (FIGS. 6 and 7).

Compound 1 Modulates ERK and STAT5, Downstream Targets of FLT3 Inhibition

Figure 8:
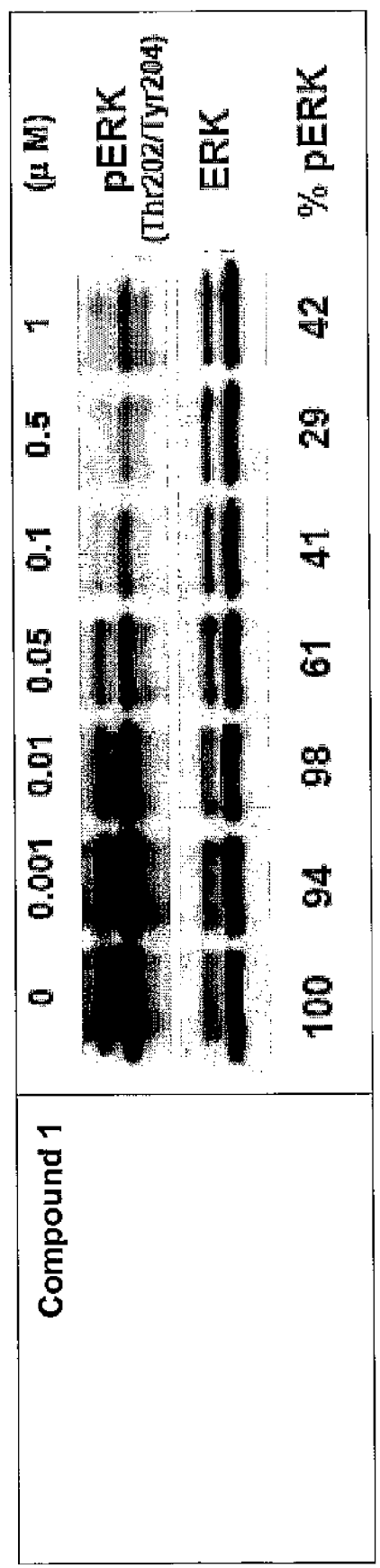
FIGS. 8 and 9 are graphs shows dose-dependent inhibition of FLT3-mediated ERK and STAT5 phosphorylation in MV4,11 cells by 4-amino-5-fluoro-3-[6-(4-methylpiperazin-1-yl)-1H-benzimidazol-2-yl]quinolin-2(1H)-one (Compound 1). MV4;11 cells (serum-starved) were incubated with various concentrations of Compound 1 for 3 hours and intracellular pERK (FIG. 8) was detected by Western blot and pSTAT5 (FIG. 9) was determined using flow cytometry. Changes in pERK or pSTAT5 are reported as percent of baseline (no treatment) using densitometry.
Figure 9:
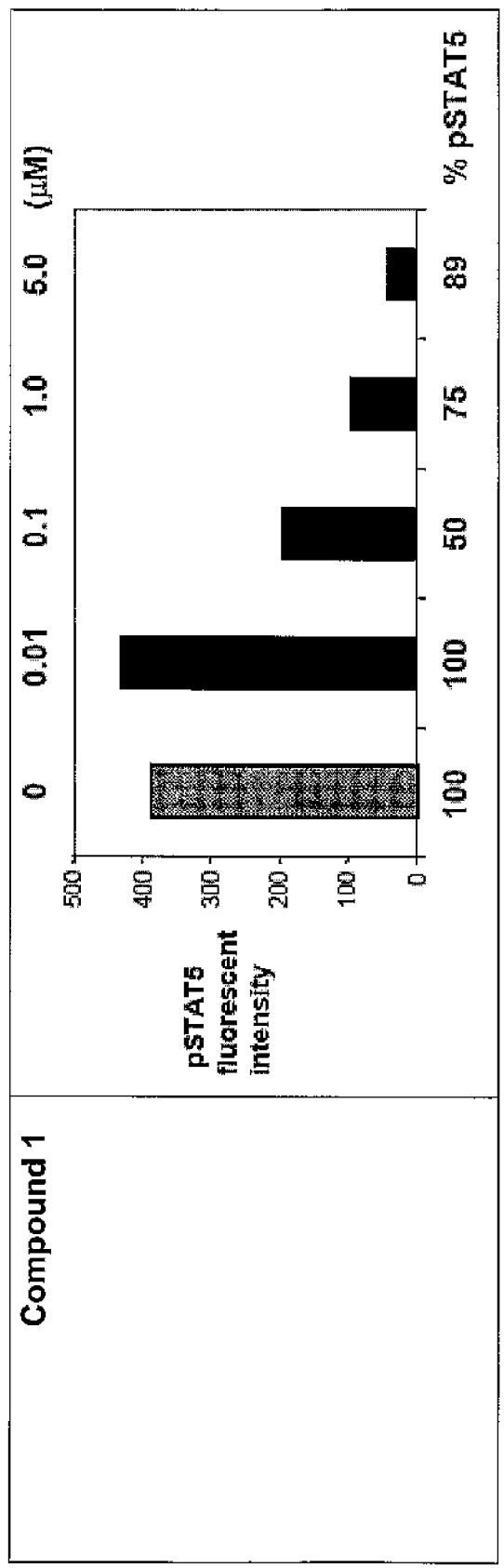

To further characterize the effects of Compound 1 on FLT3 inhibition, modulation of downstream targets of FLT3, i.e., STAT5 and ERK, which are key proteins in cell survival and proliferation were investigated. MV4;11 cells were treated with increasing concentrations of Compound 1 for 3 hours and processed by flow cytometry and Western blot for detection of pERK and p-STAT5 (FIGS. 8 and 9). In MV4;11 cells, due to active signaling of FLT3, cells have high basal levels of pERK and pSTAT5 (FIGS. 8 and 9). Compound 1 inhibited phosphorylation of ERK (FIG. 8) and STAT5 (FIG. 9) in a dose-dependent manner. Substantial inhibition of pERK and pSTAT5 (>50%) was observed at concentrations >0.1 µM (flow cytometric and Western blot). The inhibitory effects of Compound 1 on pERK and pSTAT5 was more potent in MV4;11 compared to FLT3 ligand-stimulated RS4;11 cells (data not shown).

Compound 1 Inhibits Autocrine VEGF Production in MC4;11 Cells In Vitro

Figure 10:
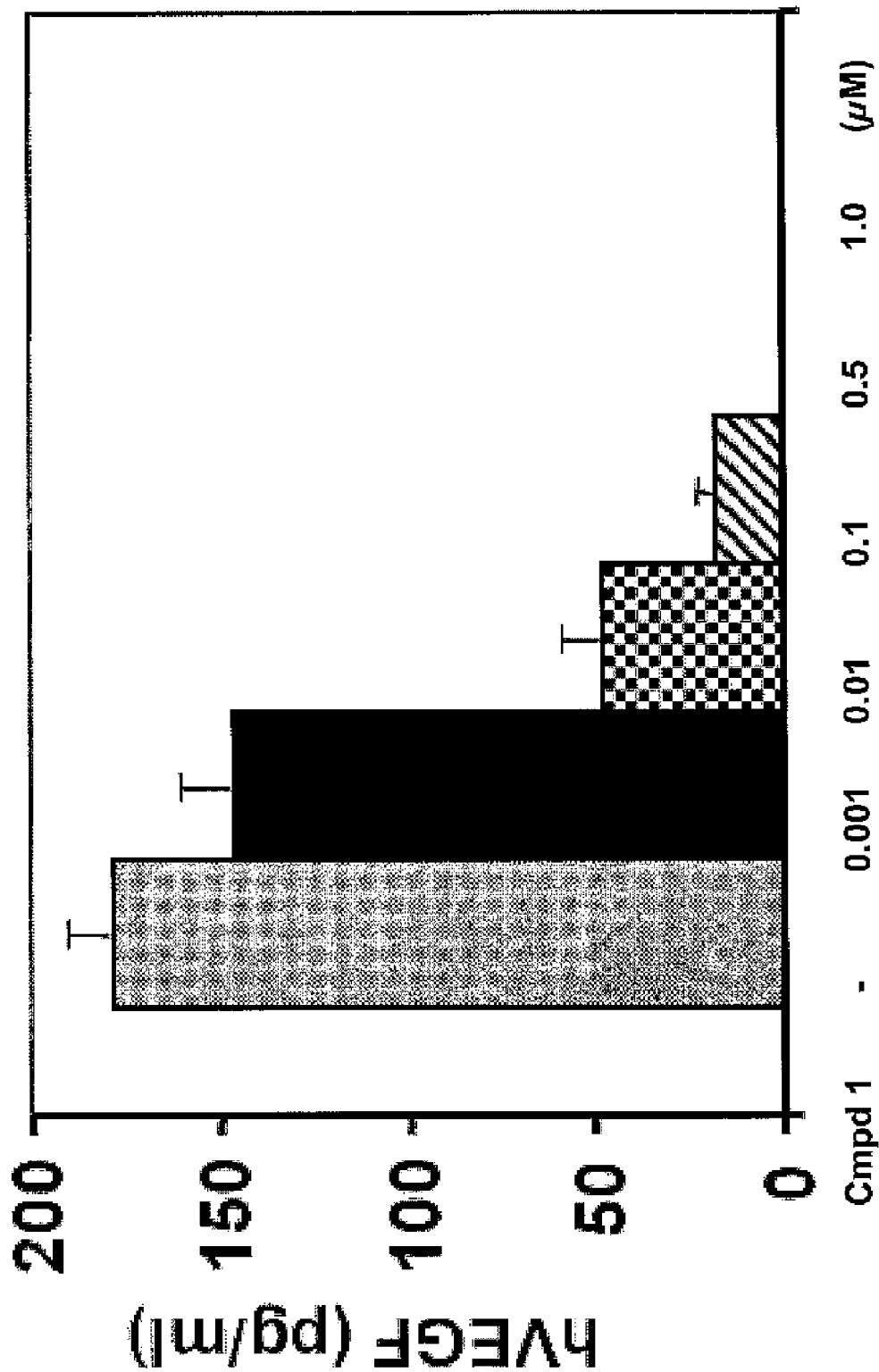
FIG. 10 is a graph showing that 4-amino-5-fluoro-3-[6-(4-methylpiperazin-1-yl)-1H-benzimidazol-2-yl]quinolin-2(1H)-one (Compound 1) inhibits autocrine VEGF production by MV4;11 cells in vitro. MV4,11 AML cells cultured in 10% FBS containing media were incubated with or without 0.001, 0.01, 0.1, 0.5 and 1 μM Compound 1 for 48 hours. Supernatants were analyzed for human VEGF levels (normalized for cellular protein content).

To address the effect of Compound 1 on VEGF production in vitro, an ELISA was performed on MV4;11 culture supernatants (FIG. 10). In these experiments, MV4;11 cells were cultured in 10% FBS containing media with increasing concentrations (0-1 µM) of Compound 1 for 48 hours. In the absence of drug treatment, MV4;11 cells secrete substantial VEGF (180 pg/ml), whereas, Compound 1 inhibited VEGF production in a dose-dependent manner, with an $EC_{50}$ between 0.001 and 0.01 µM and complete inhibition at concentrations >0.5 µM (FIG. 10).

Compound 1 Modulates FLT3 Signaling In Vivo

Figure 4:
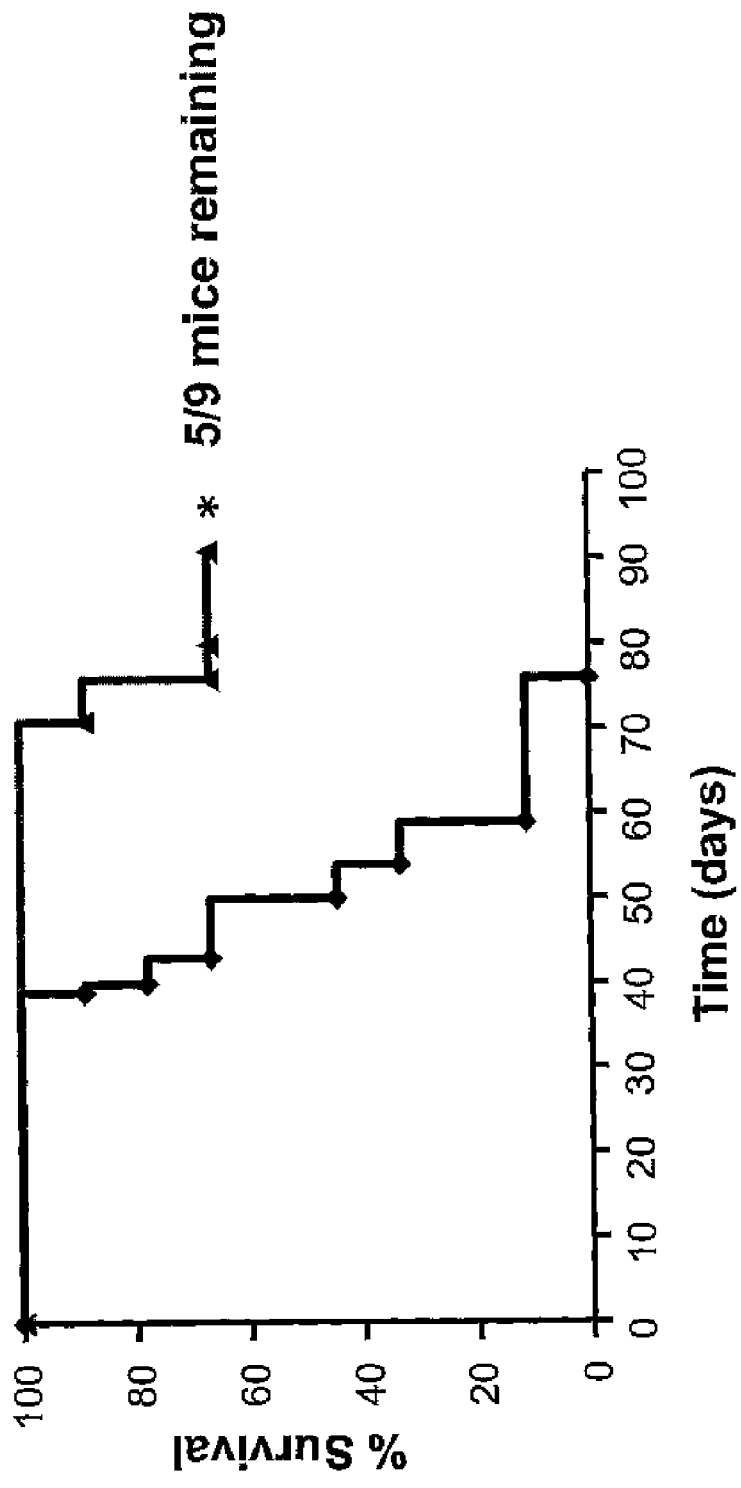
FIG. 4 is a graph comparing the survival percentage of SCID-beige mice intravenously injected with KMS-11-luc cells and then treated with either vehicle (diamonds) or with 4-amino-5-fluoro-3-[6-(4-methylpiperazin-1-yl)-1H-benzimidazol-2-yl]quinolin-2(1H)-one (triangles, 20 mg/kg/d).
Figure 11:
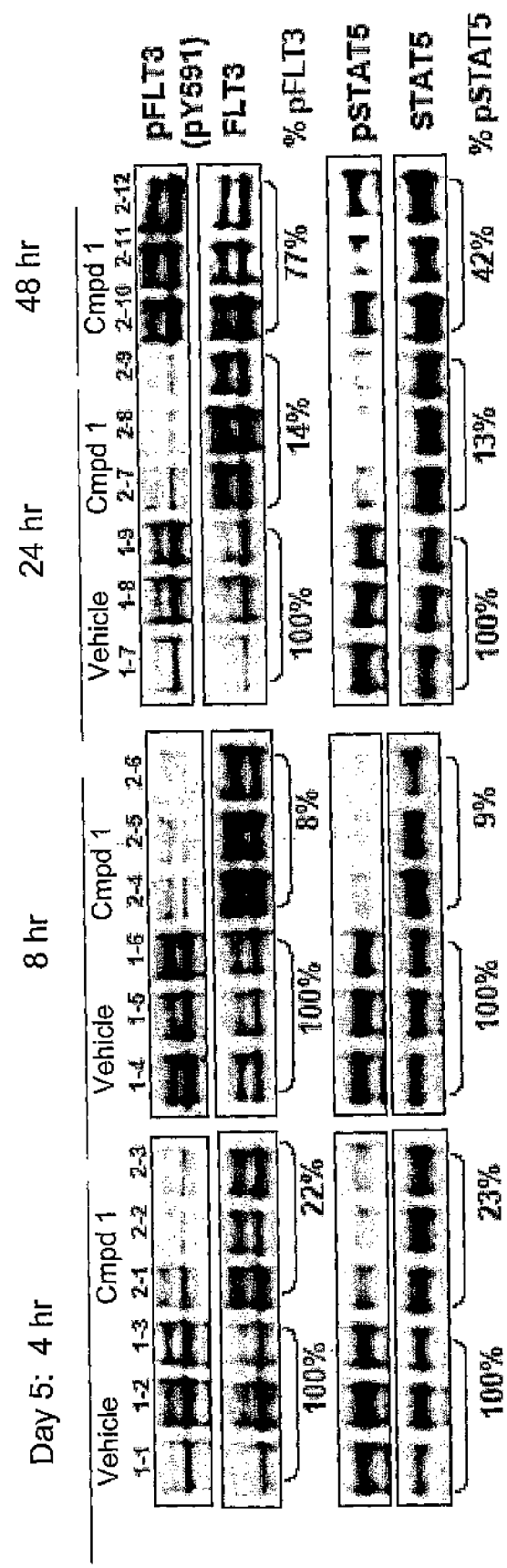
FIG. 11 is a graph showing that 4-amino-5-fluoro-3-[6-(4-methylpiperazin-1-yl)-1H-benzimidazol-2-yl]quinolin-2(1H)-one (Compound 1) inhibits FLT3 and STAT5 phosphorylation in tumors xenografts in SCID-NOD mice. SCID-NOD mice bearing s.c. MV4;11 tumors (300 mm3; n=3 mice/group) were treated with either vehicle or 10 mg/kg Compound 1 for 5 days. Tumors were resected on day 5 at 4, 8, 24, and 48 h post-dose, pulverized and immediately flash frozen (−70° C.). For pFLT3 or pSTAT5 modulation: tumor lysates were immunoprecipitated with either anti-human FLT3 or anti-STAT5 antibody, resolved by SDS-PAGE. Immunoblots were probed with appropriate antiphosphotyrosine antibody (upper lane). Membranes were stripped and re-probed with either anti-FLT3 or anti-STAT5 for determination of total FLT3 or STATS protein as loading controls (lower lane). Each lane represents a separate tumor.

To examine target modulation in vivo, MV4;11 tumor-bearing mice (staged at 300-500 mm$^3$) were administered Compound 1 (10 mg/kg/d) or vehicle for 5 days. Tumors were harvested after selected time points, homogenized and analyzed for pFLT3 and pSTAT5 levels by IP/Western blot. Significant reductions in pFLT3 and pSTAT5 levels were observed as early as 4 hours post dose with either a single dose (data not shown) or multiple doses of Compound 1 (FIG. 11), with no effects on total FLT3 or STAT5 protein (FIG. 11). Phosphorylation of both FLT3 and STAT5 declined relative to baseline reaching a maximum inhibition of −90% at 8 hour post dose and remained suppressed for 24 hours (−85% inhibition). Phospho-FLT3 returned closer to baseline levels, whereas, p-STAT5 was still inhibited (−60% inhibition) 48 hours post dose (FIG. 4). Decreases in pERK levels were also observed, indicating blockade of downstream FLT3 signalling (data not shown).

In Vivo Efficacy Studies

Dose Response Effects of Compound 1 on MC4;11 and RS4;11 Tumors In Vivo

To ascertain if the in vitro effects of Compound 1 correlate with tumor growth inhibition in vivo, efficacy of Compound 1 was examined against MV4;11 or RS4;11 tumor xenografts in SCID-NOD mice. Mice were implanted s.c., with tumor cells and Compound 1 treatments were initiated when tumors were 200-300 mm$^3$. In dose-response efficacy studies, Compound 1 was administered orally at a dose range of 1-30 mg/kg/d for MV4;11 tumors, and 10-150 mg/kg/d for RS4;11 tumors.

Figure 12:
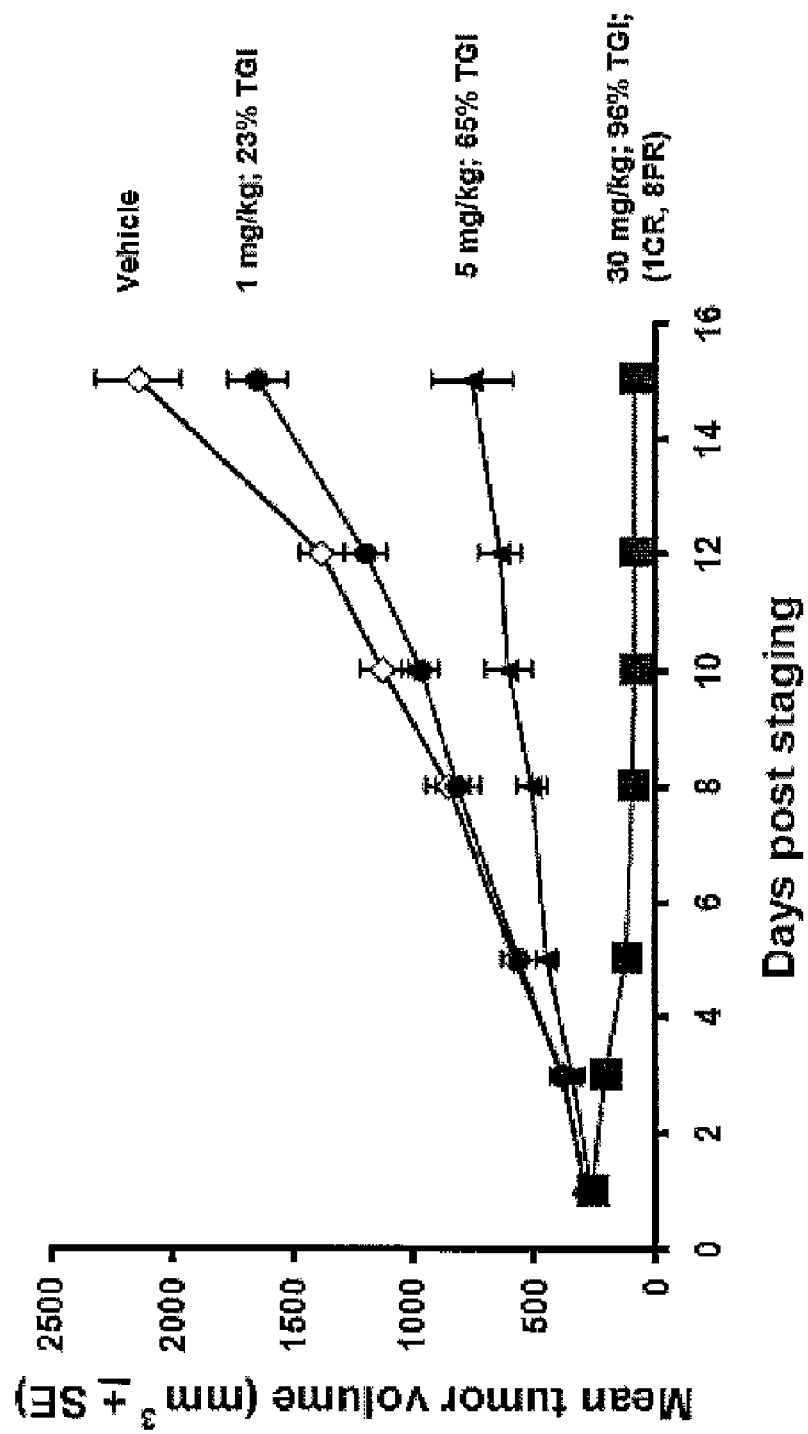
FIGS. 12-16 are graphs showing the antitumor activity of 4-amino-5-fluoro-3-[6-(4-methylpiperazin-1-yl)-1H-benzimidazol-2-yl]quinolin-2(1H)-one (Compound 1) in a subcutaneous xenograft model of human MV4;11 or RS4;11 leukemic tumors in SCID-NOD mice.
Figure 13:
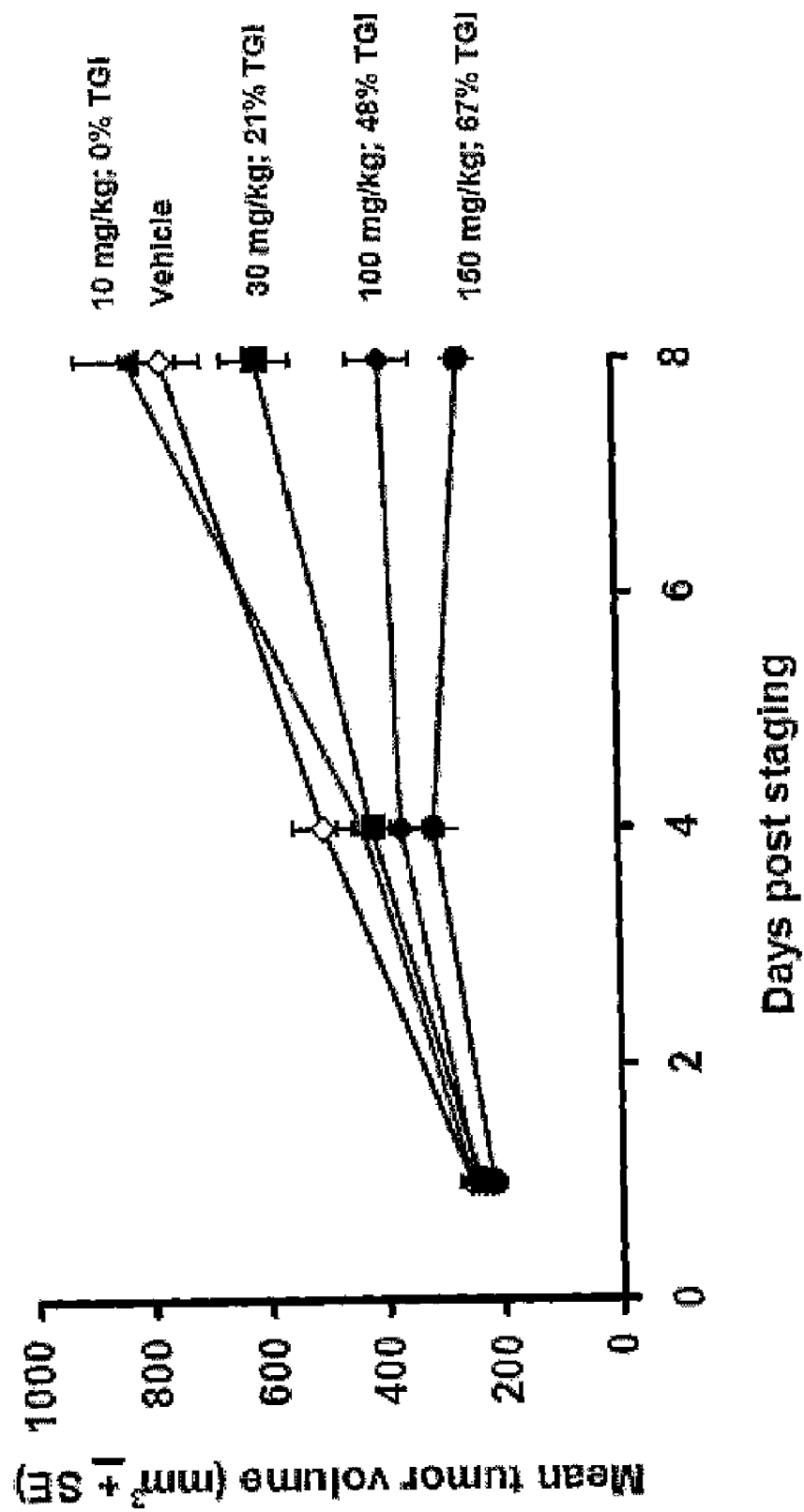

Compound 1 was highly potent against MV4;11 tumors, revealing a good dose-response effect with significant tumor growth inhibition at doses >5 mg/kg/d (FIG. 12). Doses of 30 mg/kg/d induced tumor regression (9110 tumor responses), which consisted of both partial and complete responders (1 CR, 8PR). Modest tumor growth inhibition was observed at 1 mg/kg/d (23%) after 2 weeks of dosing, and was identified as the minimum statistically effective dose in this model ($p<0.01$ vs. Vehicle). In mice bearing RS4,11 tumors, treatment with Compound 1 resulted in tumor growth inhibition, however no regressions were observed (FIG. 13). The inhibitory effects of Compound 1 were more potent against MV4;11 tumors compared to RS4;11 tumors, defined by the respective minimum effective doses in each model (day 8: 100 mg/kg/d; 48% TGI, $p<0.01$ against RS4;11 tumors vs. 1 mg/kg/d; 23% TGI; $p<0.01$ against MV4;11-tumors).

Alternate Dose Schedules of Compound 1 are Equally Potent

Figure 14:
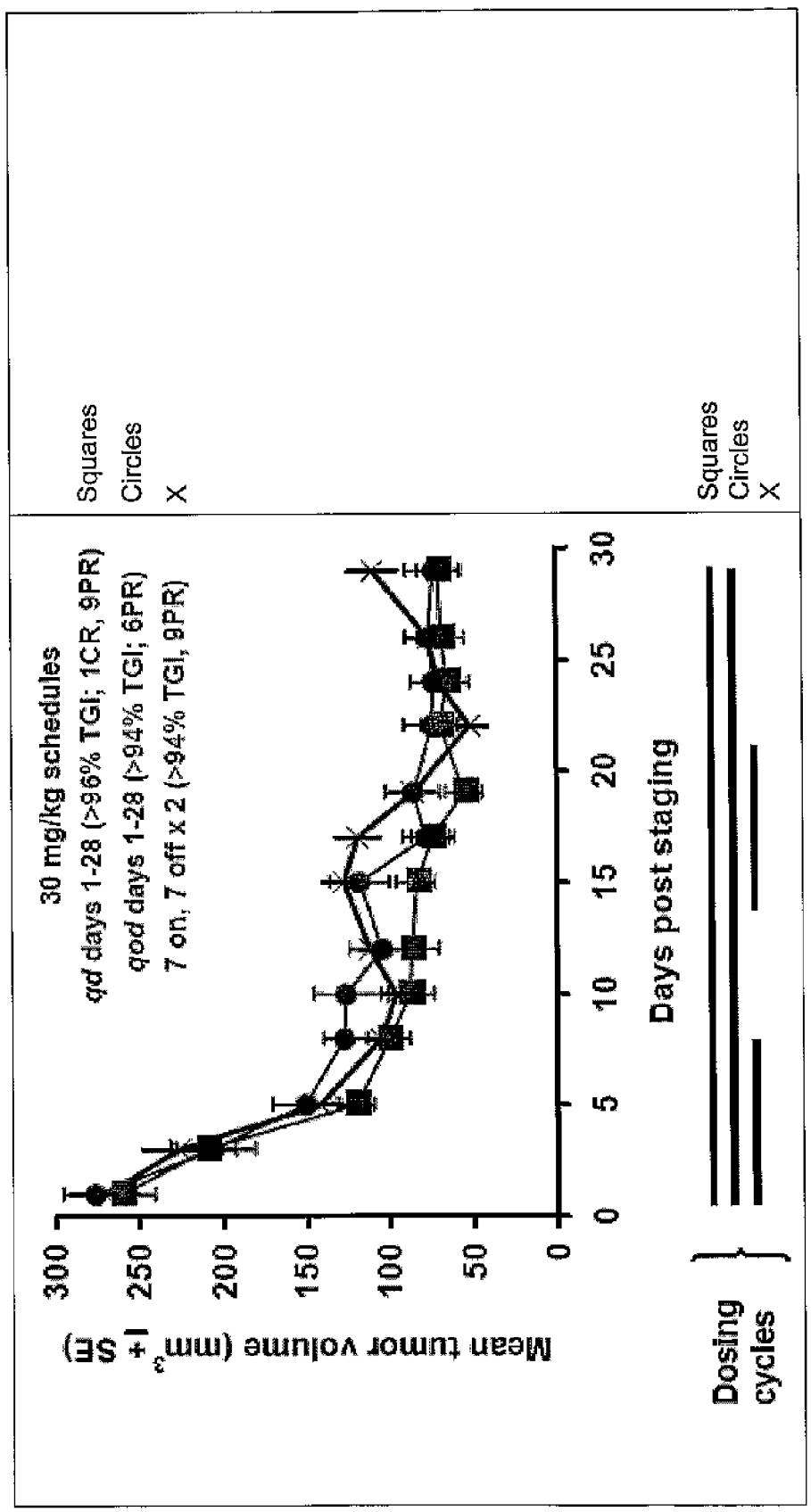

The effects of intermittent and cyclic doses of Compound 1 against MV4;11 xenograft tumors was also examined (FIG. 14). Compound 1 was administered orally at 30 mg/kg daily, every other day (q.o.d.), or cyclically, 7 days on followed by 7 days off for 2 cycles (FIG. 14). Similar to daily dosing, intermittent dosage regimens produced significant tumor regressions within days of drug treatment (>94% TGI). All three regimens resulted in equivalent anti-tumor activity (day 29, $p>0.05$) and numbers of responses seen with q.o.d. (6PR) and 7 days on/7 days off (9PR) were similar to those seen with daily treatment (1 CR, 9PR).

Compound 1 is Effective Against Large MV4;11 Tumors

Figure 15:
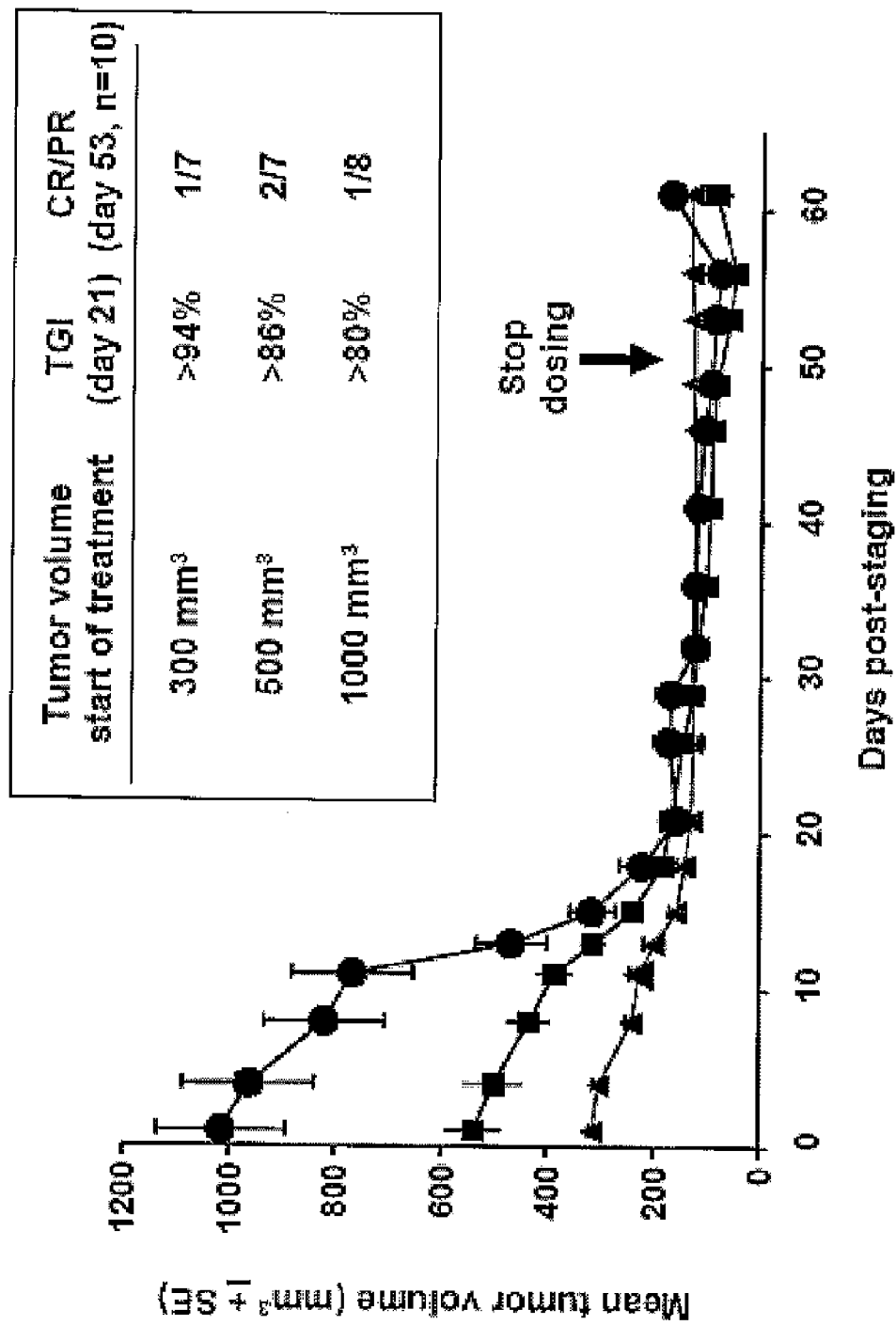
Figure 16:
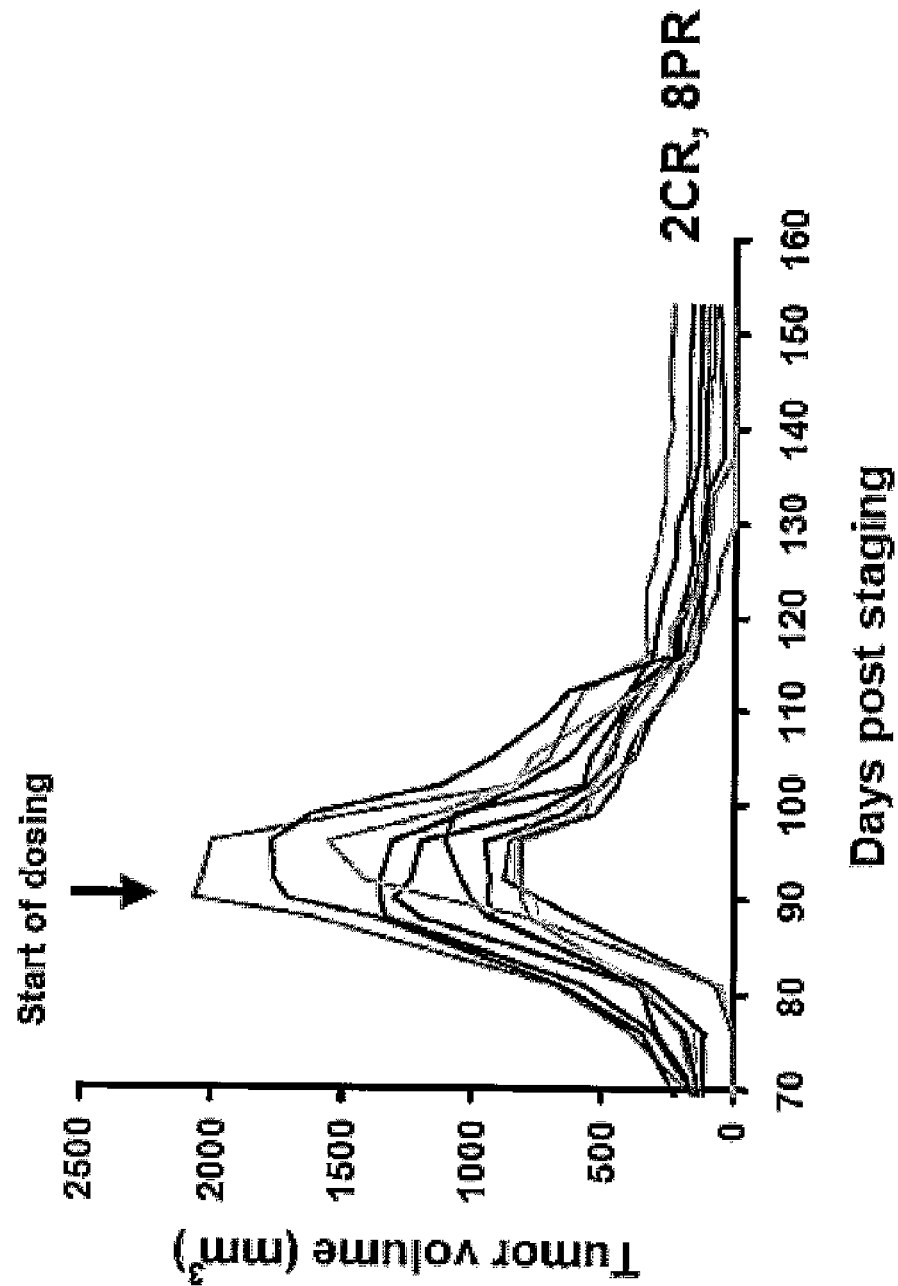

The effects of Compound 1 on large MV4;11 tumors of varying sizes; 300, 500 or 1000 mm$^3$ was also investigated. Treatment with Compound 1 (30 mg/kg/d) induced significant regression in all MV4;11 tumors which was independent of initial tumor sizes at the start of treatment (FIG. 15). Tumor regressions were evident within 3-5 days of drug treatment. All treated tumors responded (n=27), with 15% complete responses and 70% partial responses. The remaining 15% were minor responses or remained stable. Dosing was discontinued after 50 days. No tumors regrew during the 50-day treatment, indicating resistance against Compound 1 did not develop. The durability of responses after discontinuation of treatment was also examined. One CR and approximately 50% of the PRs were durable for 40 days after cessation of Compound 1 dosing. Ten tumors that re-grew (to 600-2000 mm$^3$) were re-treated with 30 mg/kg/d Compound 1 starting on study day 90 (40 days after cessation of dosing) and continued for 60 days. All tumors were responsive to the second cycle of Compound 1 (2 CR, 8 PR), clearly indicating a lack of tumor resistance to Compound 1 (FIG. 16).

Histological Evaluation of Biological Activity In Vivo

Figure 17:
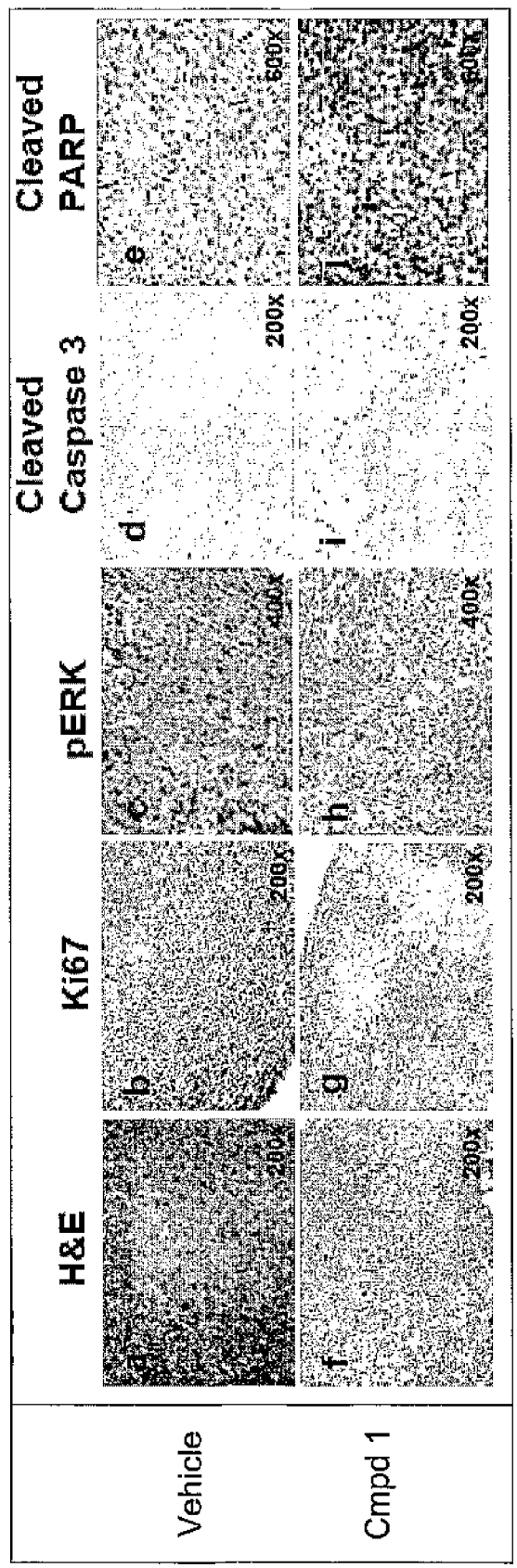
FIGS. 17-19 are graphs show tumor apoptosis/necrosis and inhibition of cellular proliferation of MV4;11 or RS4;11 tumors in SCID-NOD mice treated with 30 mg/kg 4-amino-5-fluoro-3-[6-(4-methylpiperazin-1-yl)-1H-benzimidazol-2-yl]quinolin-2(1H)-one (Compound 1).
Figure 18:
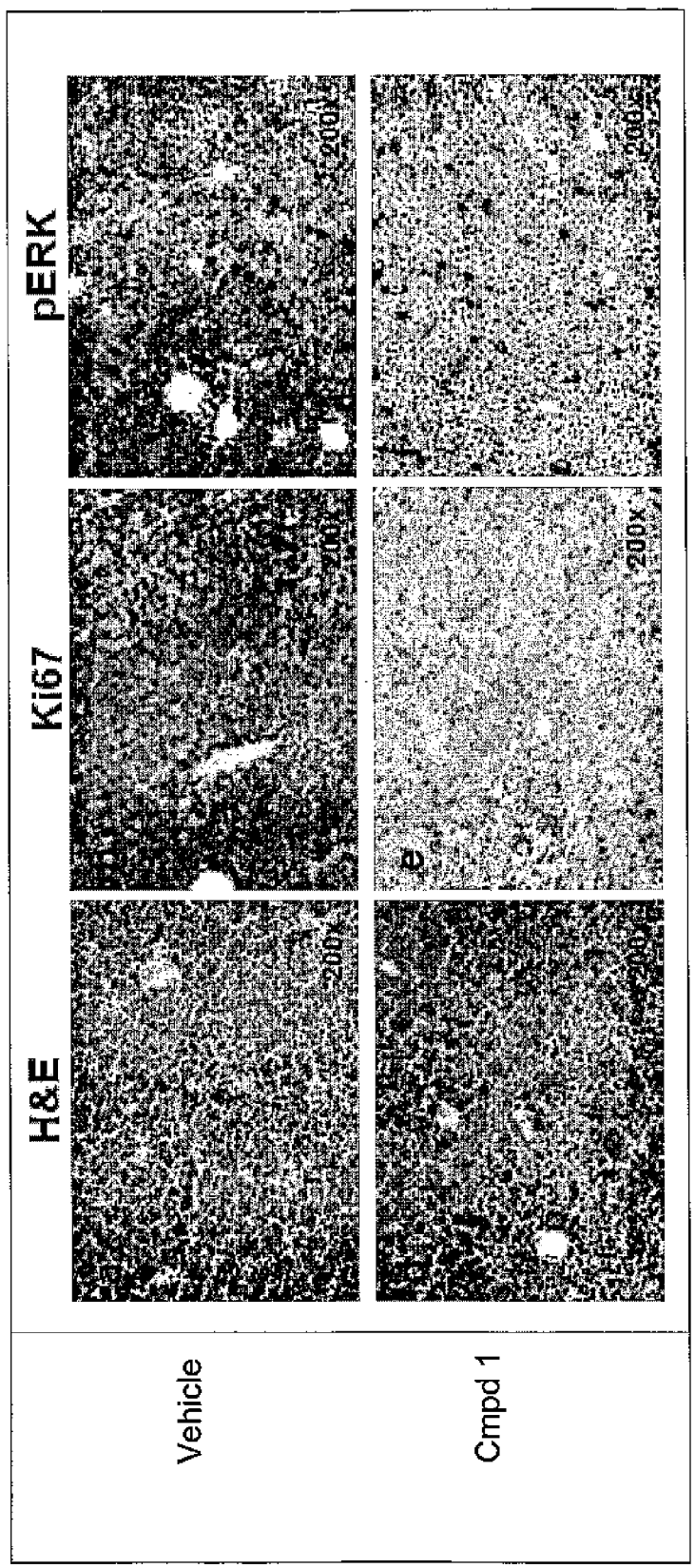
Figure 19:
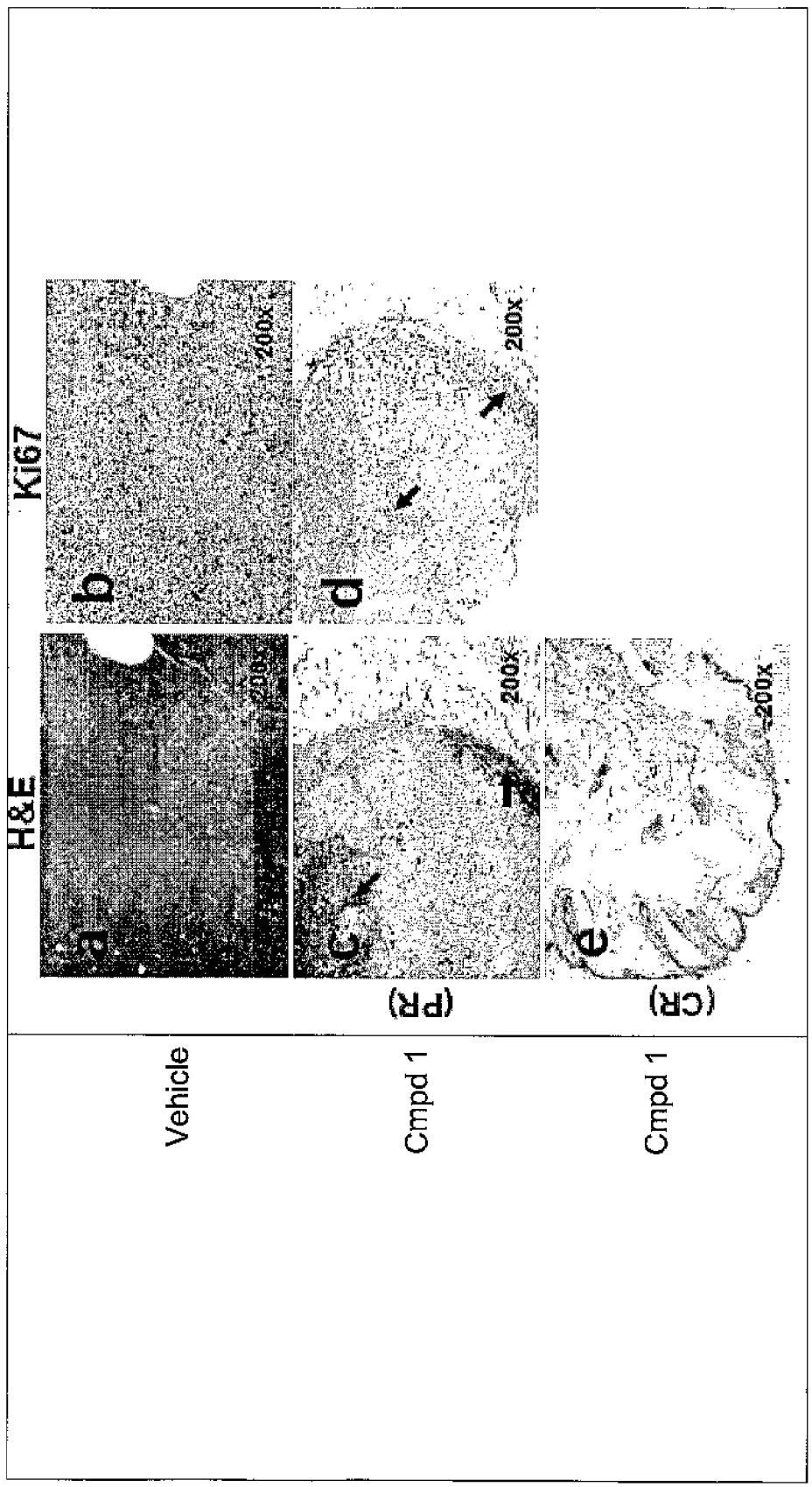

In addition to tumor volume and target modulation endpoints, immunohistochemical readouts were used as indicators of drug activity (FIGS. 17-19). Temporal effects of Compound 1 administration (30 mg/kg/d) were investigated in MV4;11 tumors after 1 or 5 doses (FIG. 17). Morphological evaluation using H&E staining, revealed that vehicle-treated tumors consisted of MV4;11 tumor cells with marked hypercellularity indicative of myeloid hyperplasia (FIG. 17-a). Tumor cells stained strongly with Ki67 indicating a tumor composition of highly proliferating cells (FIG. 17-b). By 24 hours after dosing, tumors treated with Compound 1 showed a reduction in densely packed cells and consisted of sparse areas of apoptotic/necrotic cells (day 1, FIG. 17-a vs. f). Areas of apoptosis/necrosis were more pronounced after 5 doses with significant areas of nonviable tumor coincident with reduced Ki67 staining (FIG. 179). Target modulation was confirmed in vivo from immunohistochemical staining of pERK. Phospho-ERK was significantly lowered in Compound 1-treated tumors during the 5-day dosing period corroborating Western analyses of pERK in tumors (FIG. 17-c vs. h). Compound 1-induced apoptosis, evidenced from increased activated caspase-3 (FIG. 17-d vs. i) and cleaved PARP (FIG. 17-e vs. j) staining in tumors on day 5 compared to vehicle-treated controls. Similar effects of decreased cellularity and proliferation as well as reduced pERK were evident in RS4;11 tumors treated with Compound 1 (30 mg/kg/d) (FIG. 18).

The histology of tumors that were either defined as partial (FIG. 19-c,d) or complete responses (FIG. 19-e) were also examined. Complete responders were totally devoid of MV4;11 tumor cells, displaying only remnants of necrosis and/or scar tissue (FIG. 19-e). In partial responses, pockets of Ki67-positive proliferating tumor cells were observed at the periphery of tumors (FIG. 19-a,c vs. b,d).

Figure 20:
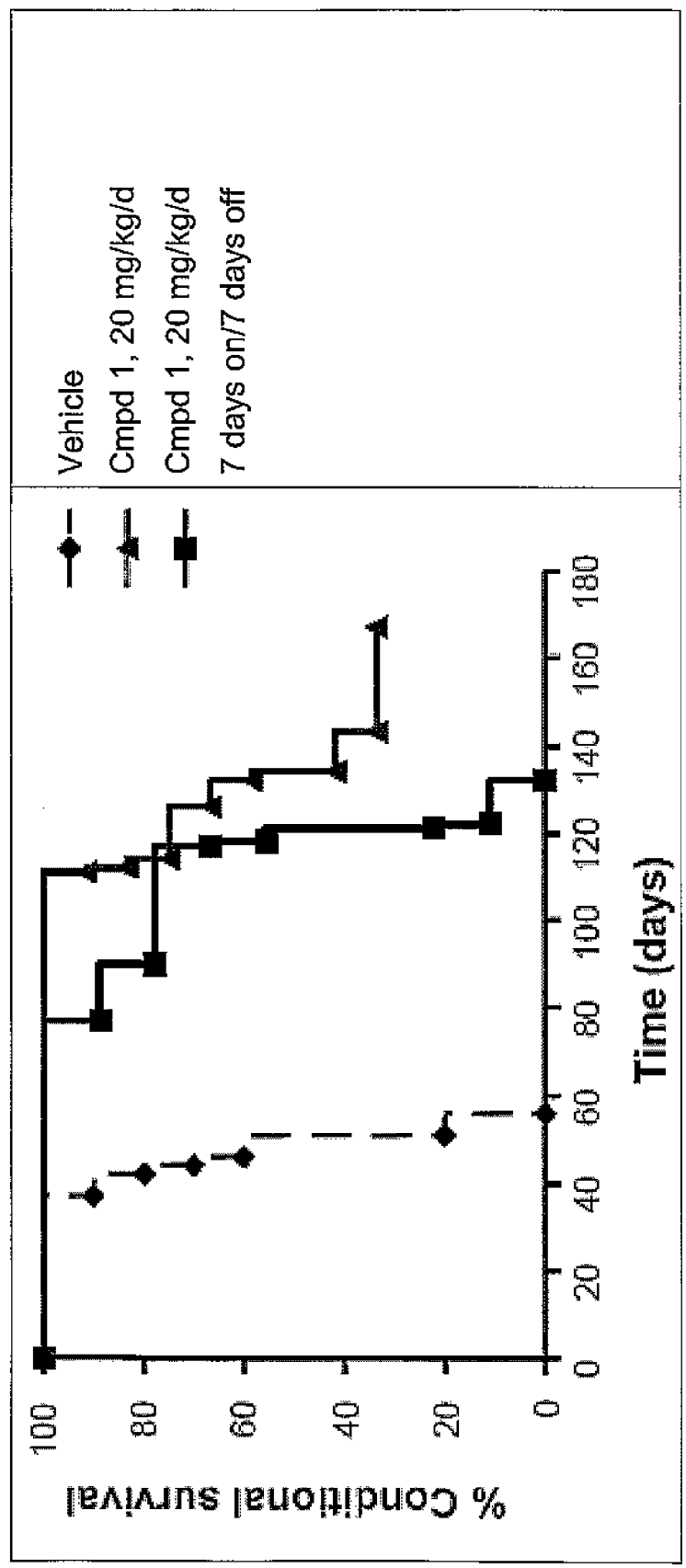
FIGS. 20 and 21 are graphs showing that 4-amino-5-fluoro-3-[6-(4-methyl piperazin-1-yl)-1H-benzimidazol-2-yl]quinolin-2(1H)-one (Compound 1) prolongs survival of SCID-NOD mice bearing intravenous MV4;11 cells. Irradiated SCID-NOD mice were implanted with MV4;11 (1×107 cells, i.v.), i.v. Treatments were initiated on day 23, consisting of either oral Vehicle (♦) or Compound 120 mg/kg given daily (▲) or scheduled 7 days on/7 days off (■) from days 23-98. Mice eliciting early signs of hind-limb paralysis or poor health condition were euthanized.
Figure 21:
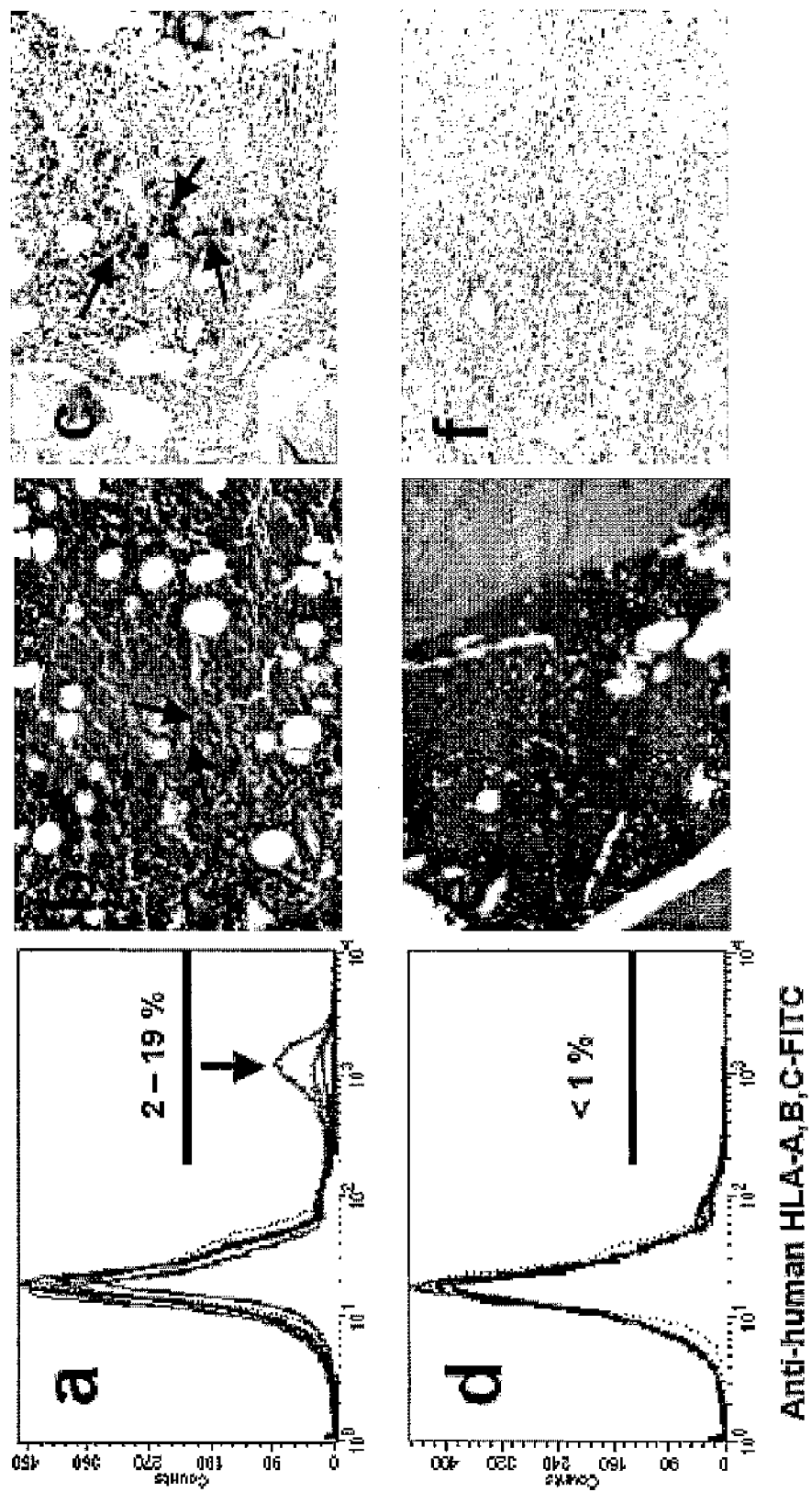

Compound 1 Prolongs Survival Time of Mice Bearing Disseminated Human Leukemia Cells Efficacy of Compound 1 was tested in the MV4;11 leukemia model in which cells were inoculated into the tail vein of irradiated SCID-NOD mice (FIG. 20). In this model, MV4;11 cells disseminate to the bone marrow (BM), pathologically mimicking a disease pattern similar to human leukemia. Mice were injected with MV4;11 cells on day 1 and treatments of Compound 1 (20 mg/kg, daily or 7 days on/7 days off, n=10-12/group) were initiated on day 23, after MV4;11 cells engraft in BM. Control (vehicle-treated) mice typically elicit hind limb paralysis as a consequence of tumor cells infiltrating the BM, with a median survival time (MST) of 51 days (FIG. 20). In survival studies, daily treatment with Compound 1 (day 23-100) significantly delayed time to disease progression (MST=134 days) compared to vehicle-treated controls (MST=51 days) ($p<0.0001$), demonstrating a 163% increased life span (ILS) (FIG. 20). Strikingly, with daily Compound 1 treatment, 4 mice were long-term survivors (MST >160 days). Histological analyses and flow cytometry were used to quantify the % engraftment of MV4;11 cells in BM (FIG. 21). In flow cytometric analyses, human MV4;11 cells were identified in mouse BM with an anti-human HLA-A,B,C antibody which binds to an epitope on human MHCl. In vehicle-treated mice, approximately 2-19% of total isolated BM cells consisted of engrafted MV4;11 cells (day 51, FIG. 21-a). This was also corroborated by immunohistochemistry with an antibody to human mitochondria which stains MV4;11 cells identifying the human cells in the mouse BM matrix (FIG. 21-b,c). Compound 1 dosed daily (20 mg/kg) over 25 days significantly reduced leukemic burden (<1% MV4;11 cells in BM) vs. vehicle treatment (FIG. 21-a vs. d). Interestingly, surviving mice after Compound 1 treatment immunohistochemically showed no evidence of tumor cells (seen as an absence of anti-human mitochondrial-positive cells on day 167) in the BM and were defined as "cures" (FIG. 21-e,f). Cyclic dosing of Compound 1 (7 days on/7 days off, 5 cycles) also resulted in significantly increased survival times (MST=118 days, 131% ILS vs. vehicle, p=0.0001), but was not as effective as the daily regimen (p=0.007, FIGS. 20 and 21).

Discussion

Targeting aberrant intracellular kinase signaling pathways implicated in tumor-cell proliferation can disrupt cellular processes and cause inhibition of tumor growth. This has been exemplified by the approval of two small molecule targeted agents imatinib (Gleevec) in CML (Bcr-Abl) and gastrointestinal stromal tumors (c-KIT) and gefitinib (Irressa) in refractory advanced or metastatic non-small cell lung cancer (EGFR). Druker B. J. *Oncogene,* 21:8541-8546 (2002); Giaccone G. *Clin Cancer Res.* 10:4233 S-4237S (2004). Both compounds target specific molecular defects in tumor cells and this success has driven research on molecular targeted therapies to other oncogenic kinases, including FLT3 15,20-23. Mutations in the FLT3 gene are the most common genetic alteration in AML, where nearly 35% of patients harbor activating mutations FLT3 mutations have been shown to confer a poor clinical prognosis thus implicating FLT3 as a therapeutic target in AML. Thiede C. et al, *Blood,* 99:43264335 (2002); Schnittger S, et al., *Blood,* 2002;100;59-66 (2002).

Compound 1 is a multitargeted kinase inhibitor with nanomolar potency against class III, IV and V RTKs involved in tumor proliferation and angiogenesis. Biochemical kinase assays demonstrate that Compound 1 has potent activity against FLT3 (1050 of 1 nM). The activity of Compound 1 in two leukemic cells lines was characterized with contrasting FLT3 status, MV4;11 (FLT3 ITD) and RS4;11 (FLT3 WT). Compound 1 was shown to reduce FLT3 phosphorylation in a dose-dependent manner, confirming molecular activity in cells. In vitro, Compound 1 blocked subsequent downstream signalling molecules in mitogenic MAPK and STAT5 pathways, both key regulators in cell proliferative pathways. Interestingly, activity on FLT3 target modulation was more pronounced in MV4;11 than RS4;11 cells as were the effects of Compound 1 in cell cytotoxicity/proliferation assays. Similar differential effects against FLT3-ITD and wild-type FLT3 have been reported for other FLT3 inhibitors. It can be reasoned that FLT3 ITD MV4;11 cells have constitutively active signals (Ras, STAT5) which drive cell proliferation, and differ from FLT3 WT (RS4;11) cells which can sustain growth independent of FLT3 activation and/or may rely on other oncogenic pathways. Minami Y. et al., *Blood,* 102:2969-2975 (2003); Kiyoi H. et al., *Oncogene,* 21:2555-2563 (2002); Spiekermann K. et al., *Clin Cancer Res.* 9:2140-2150 (2003).

The results from in vivo studies have demonstrated that Compound 1 has potent activity against both solid tumor and disseminated BM models of leukemia. The molecular activity of Compound 1 in preclinical models was addressed using PD endpoints to study the extent and duration of target modulation. Compound 1 was shown to substantially down-regulate both pFLT3 and pERK in MV4;11 tumors. Target modulation (pFLT3) was observed by 4 hours and was sustained in tumors up to 24 hours following a single dose or multiple doses of Compound 1. Biological effects were also evident from tumor histopathology, where decreased pERK, proliferation and apoptosis responses in tumors were observed within 1-2 days of drug treatment. In solid tumor xenografts of MV4;11, tumor regressions were also pronounced within days of drug treatment. It is possible that potent inhibitory effects of Compound 1 in the MV4;11 model may arise from direct inhibition of FLT3 in combination with inhibition of other RTKs. Data (RT-PCR, not shown) indicatres that MV4;11 cells also express VEGFR1, cKIT, PDGFRβ, FGFR1, CSF-1R 32, all RTKs potently inhibited by Compound 1. Compound 1 has <10 nM activity against VEGF1/2/3 kinases, and the data clearly demonstrates that Compound 1 can inhibit autocrine VEGF levels in MV4;11 in vitro cultures. In vivo, autocrine or paracrine inhibition of secreted VEGF or FGF by tumor cells or tumor stromal cells (including endothelial cells) may inhibit proliferation and survival of these cells. Ferrara N. et al., *Nat. Med.,* 9:669-676 (2003); Compagni A. et al., *Cancer Res.* 60:7163-7169 (2000); Carmeliet P. *Nat. Med.,* 9:653-660 (2003). Additional activity of Compound 1 in solid tumors may arise from its potent effects against PDGFRβ by impacting perlcyte recruitment and maturation of blood vessels during angiogenesis. Carmeliet P. *Nat. Med.* 9:653-660 (2003); Ostman A. *Cytokine Growth Factor Rev,* 15:275-286 (2004). In the AML BM model, we demonstrate that Compound 1 improved survival of mice and in some mice eradicated disease. This represents the potential of Compound 1 to eradicate both circulating blasts and BM disease by direct anti-proliferative effects or regulation of bone marrow angiogenesis, which may play a role in blast survival. Carow C. E. et al., Blood, 87:1089-1096 (1996); Drexler H. G. Leukemia, 10:588-599 (1996).

Based on the pharmacology and target inhibition of Compound 1, intermittent and cyclic dose schedules of Compound 1 were studied. Alternate dosing schedules of Compound 1 demonstrated similar activity compared to daily doses of Compound 1, suggesting the potential for flexible dosing regimens in the clinic. Multiple doses of Compound 1 were able to continually suppress growth of tumors and any recurring tumors after cessation of treatment were found to be equally sensitive to re-treatment with drug. These findings are relevant if translated in the clinical setting, as some AML patients have been shown to relapse on treatment with kinase inhibitors despite continued treatment. Fiedler W. et al., *Blood*, (2004); Cools J. et al., *Cancer Res.* 64:6385-6389 (2004). Multiple mechanisms including metabolism or cellular efflux (via expression of drug transporters such as P-glycoprotein), or mutations in the ATP binding domains of the enzyme active sites that interfere with drug binding have been shown to correlate with resistance to kinase inhibitors. Bagrintseva K. et al., *Blood,* 103:2266-2275 (2004); Grundler R. et al., *Blood,* 102:646-651 (2003). Compound 1 is not a P-GP substrate, and the durable responses throughout the course of drug treatment may imply that the development of resistance may be avoided with Compound 1.

The clinical development of FLT3 inhibitors (SU11248 PKC412, CEP-701, MLN518) for AML is still in early phases. O'Farrell A. M. et al., *Clin. Cancer Res.* 9:5465-5476 (2003); Fiedler W. et al., *Blood*, (2004); Stone R. M. et al., *Ann Hematol.* 83 Suppl 1:S89-90 (2004); Smith B. D. et al, *Blood,* 103:3669-3676 (2004); DeAngelo D. J. et al., Blood, 102:65a (2003). Selection of single agent therapies has not yet produced significant responses, and the future clinical development of FLT3 inhibitors in AML may depend on combining these agents with either cytotoxic dugs or other molecular targeted agents. The data reported here for Compound 1, a potent FLT3 inhibitor with additional activity on RTKs known to play roles in the pathogenesis of AML warrants its clinical evaluation.

Activity Against Drug-Resistant Cancers in Patients

Figure 22:
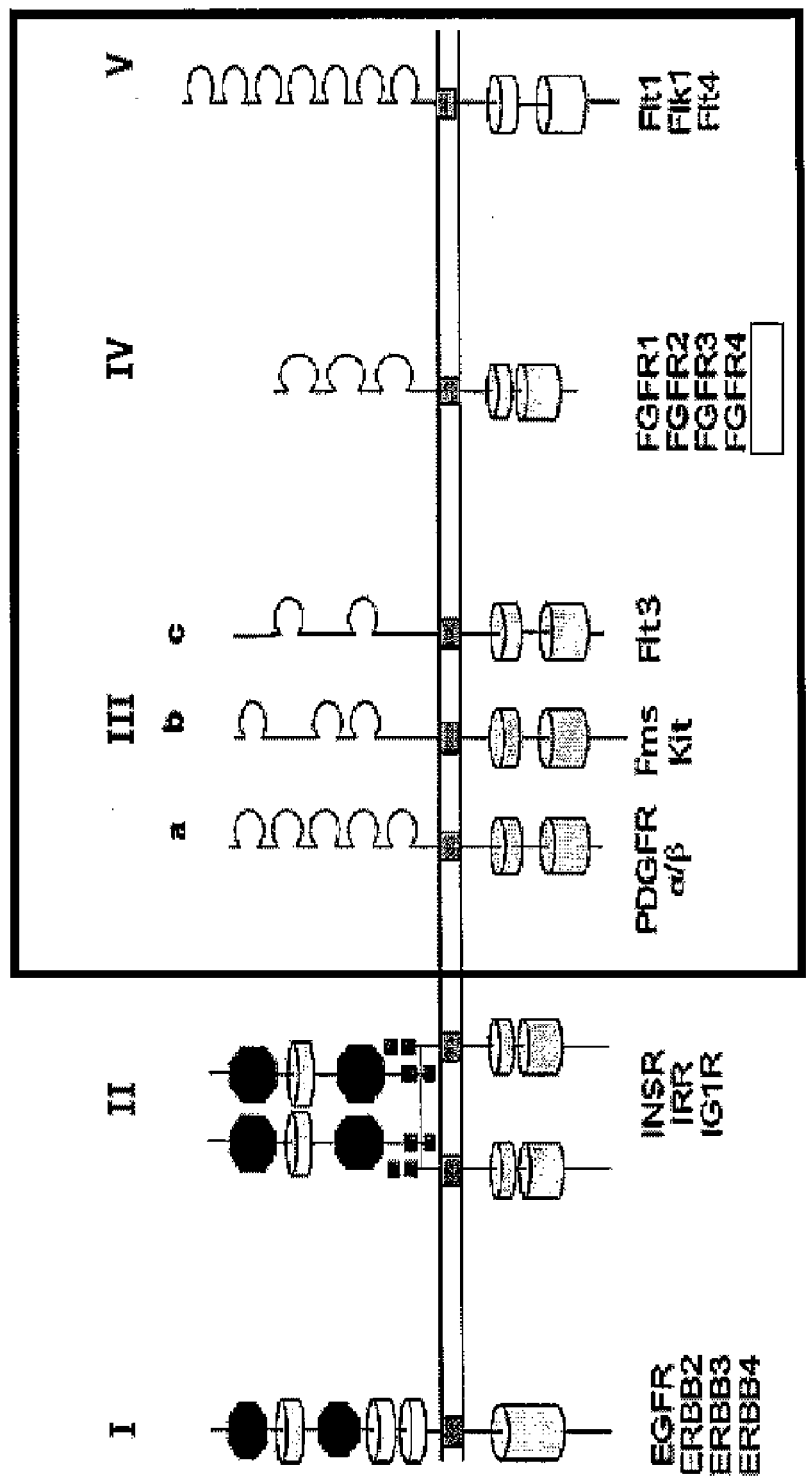
FIG. 22 is a scheme showing how the compounds of the invention selectively inhibit Class III, IV, and V receptor tyrosine kinases (See also Table of Activity of 4-Amino-5-fluoro-3-[6-(4-methylpiperazin-1-yl)-1H-benzimidazol-2-yl]quinolin-2(1H)-one Against Various RTKs).
Figure 23:
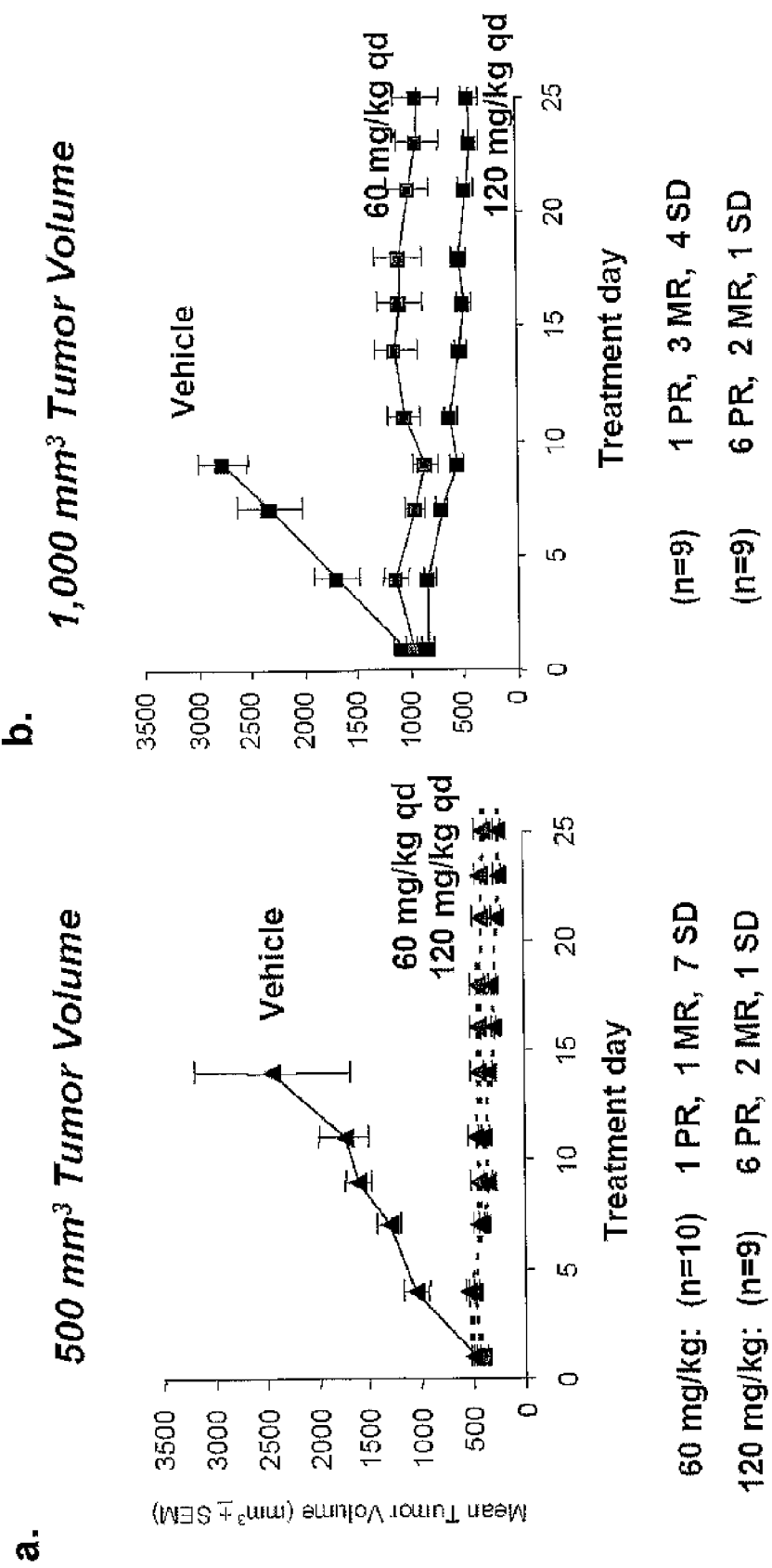
FIGS. 23a and 23b are graphs plotting tumor volume as a function of days of treatment with vehicle and with 4-amino-5-fluoro-3-[6-(4-methylpiperazin-1-yl)-1H-benzimidazol-2-yl]quinolin-2(1H)-one. These graphs show that treatment with Compound 1 caused regression and/or disease stabilization in 90-100% of animals with large, established colon xenografts KM12L4A human colon tumor xenografts in nude mice were dosed daily with Compound 1 when tumors reached 500 mm³ (23a) or 1000 mm³ (23b)).

Compounds of formula I, II, and III, such as 4-amino-5-fluoro-3-[6-(4-methyl-piperazin-1-yl)-1H-benzimidazol-2-yl]-1H-quinolin-2-one (Compound 1), have direct activity against tumor cells and the formation and maintenance of blood vessels supplying tumors. These compounds have also shown oral activity in a variety of angiogenesis tumor and metastases animal models. As shown in FIG. 22, Compound 1 selectivity inhibits Class III, IV and V RTKs (See also Table with $IC_{50}$ values). Administration of Compound 1 to nude mice having large, established KM12L4A human colon tumor xenografts provided regression and/or disease stabilization in 90-100% of treated animals (See FIG. 23).

Phase I dose escalating multi-center open label studies were conducted to evaluate the safety, pharmacokinetics, and pharmacodynamics of Compound 1 in subjects with advanced solid malignancies. Further primary objectives of the studies included: 1) determining the Maximum Tolerated Dose (MTD); 2) identifying Dose Limiting Toxicity (DLT); and 3) assessing safety provil in subject with advanced solid tumors. Secondary objectives of the study included: 1) evaluating pharmacokinetics; 2) evaluating pharmacodynamics in plasma, peripheral blood lymphocytes, urine, and tumor cells; 3) recommending dose and schedule for future investigations; and 4) determining evidence of anti-tumor activity (RECIST). Details regarding this study are set forth below Dosing Regimens included:
  Single daily dosing 7 days on/7 days off, repeated (doses 25-100 mg)
  Doses ≧100 mg one cycle of 7 days on/7 days off, followed by continuous daily dosing thereafter
Dose Escalation:
  3-4 patients per cohort, dose doubling until >Grade 2 toxicity; then modified Fibonacci schema
Inclusion Criteria:
  Histologically or cytologically documented solid tumours, refractory to standard therapy or for which no curative standard therapy exists
  Age >18 years
  ECOG performance status 0-1
  Haemoglobin≧8.0 gm/dL; Neutrophils≧1,500/mm³; Platelets≧75,000/mm³
  Creatinine≦1.5×upper limit of normal (ULN); Bilirubin≦1.5×ULN; Alkaline phosphatase≦5×ULN; Aspartate aminotransferase (AST)≦2.5×ULN (except liver involvement≦5×ULN); Amylase≦ULN
  Signed informed consent
  Last dose of antineoplastic therapy (except for hormonal therapy)>21 days
Exclusion Criteria:
  Intracranial oedema, intracranial metastasis or epidural disease
  Clinically significant cardiac disease (NYHA Class III or IV); pre-existing arrhythmia; congestive heart failure; cardiomyopathy; QTc interval >450 msec (males) and >470 msec (females) or >G2 LVEF (by MUGA or echocardiogram)
  Diabetes mellitus (requiring chronic medication) with signs of clinically significant peripheral vascular disease
  Previous pericarditis; clinically significant pleural effusion in the previous 12 months or recurrent ascites requiring >2 interventions/month
  Malabsorption syndrome or uncontrolled G1 toxicities (>G2 nausea, diarrhea, vomiting). Prior acute or chronic pancreatitis of any aetiology
  Prior intra- or extra-hepatic biliary obstruction within the previous 12 months or history of malignant obstruction requiring a biliary stent, unless stably treated with no prior obstruction or blockage of the stent Definition of DLT/MTD:
  G4 neutropenia <5 days or febrile neutropenia; G4 thrombocytopenia
  G4 fatigue, or a two-point decline in ECOG performance status
  G3 or greater nausea and/or vomiting despite the use of adequate/maximal medical intervention and/or prophylaxis
  G3 or greater non-hematological toxicity (except fatigue)
  G2 or greater cardiac toxicity of clinical significance (e.g. a decline in the resting EF to 40%≦50% or shortening fraction to 15%≦24%; cardiac troponin T/I≧0.05 ng/Ml
  MTD: dose level below which >2/6 patients experience DLT Patient characteristics:

Patient Characteristics

| | | |
|---|---|---|
| No. of Subjects (22 Apr. 2005): | | 25 |
| Median Age (range): | | 57 (30-72) |
| Gender: | Male | 14 |
| | Female | 11 |
| ECOG PS: | 0 | 12 |
| | 1 | 7 |
| Prior Chemotherapy Regimens (Number) | 0-3 | 8 |
| | 4-6 | 4 |
| | >6 | 2 |
| Tumour Types | Prostate | 5 |
| | Renal | 3 |
| | GIST | 2 |
| | Sarcoma | 2 |
| | Colorectal | 1 |
| | Breast | 1 |
| | Parolid | 1 |
| | Gastric | 2 |
| | Melanoma | 2 |
| | Oesophageal | 2 |
| | NET(Sinonasal) | 1 |
| | Colon | 1 |
| | Ovarian | 1 |
| | Liver | 1 |

Dose Levels:

| Dose Level | No. of Patients | DLT(Occurring in Cycle 1) |
|---|---|---|
| 25 mg | 3 | 0 |
| 50 mg | 4 | 0 |
| 75 mg | 4 | 0 |
| 100 mg(7on/7off) | 4 | 0 |
| 100 mg(continuous) | 6 | 1(G 3 Hypertension) |
| 125 mg(continuous)* | 4 | 0 |

*enrollment ongoing

Drug-related clinical adverse events greater than or equal to G2:

| AE | 25 | 50 | 75 | 100 | 100 Cont. | Total |
|---|---|---|---|---|---|---|
| Fatigue | 3 | 1 | 1 | | 1 | 5 |
| Anaemia | 3 (2 G3) | 1 | | | | 4 (2 G3) |
| N & V/Diarrhoea | 1 (1 G3) | 2 (2 G3) | 2 | 2 | | 7 (3 G3) |
| Headache | | 3 (1 G3) | | | 1 | 4 (1 G3) |
| Anorexia | 2 | | | | | 2 |
| Reduced LVEF | | | 1 | 1 | | 2 |
| Hypertension** | | | | | 2 (1 G3) | 2 (1 G3) |

**DLT

Figure 24:
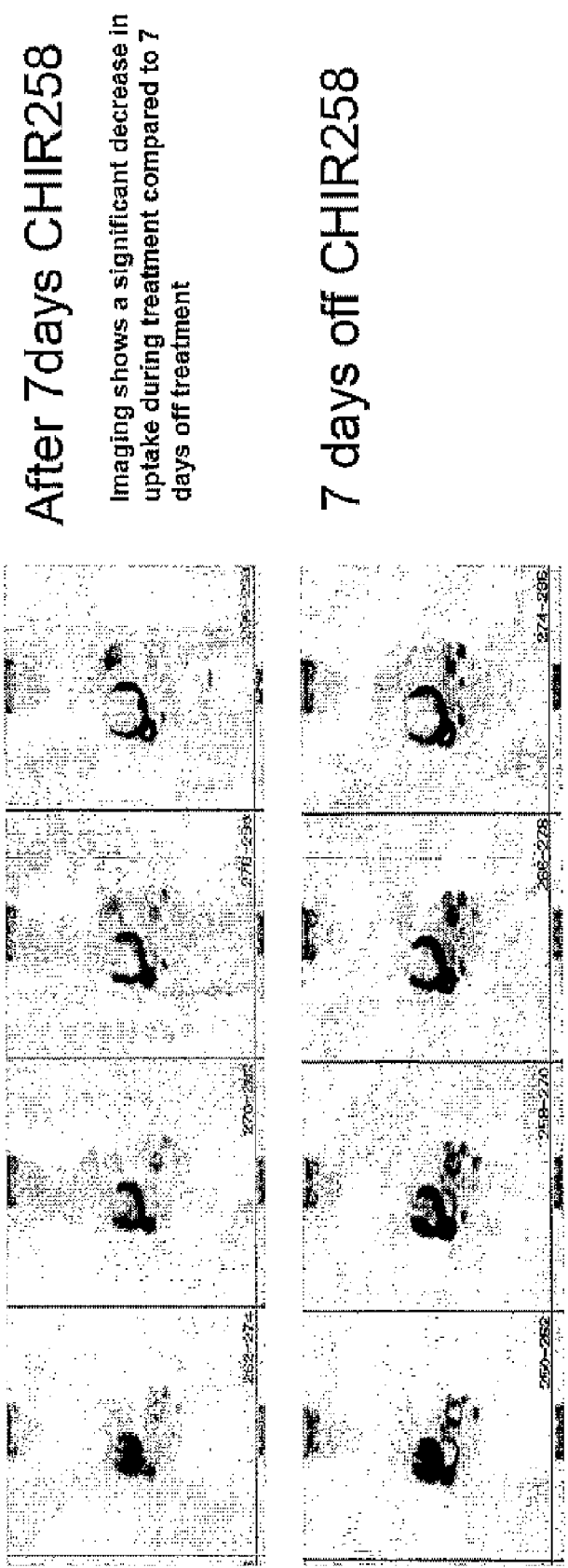
FIG. 24 are scanned PET-CT images of a human female patient with imatinib-refractory GIST treated with Compound 1 (CHIR258).

Evidence of antitumor activity of Compound 1 has been observed as 7/22 (32%) of patients had stable disease (SD) at their first evaluation. In addition, SD for greater than 4 months has been reported in 4 patients, including a patient with a parotid glad tumor (greater than 7 months) and a Gleevec-refractory GIST patient (greater than 6 months). FIG. 24 is a scanned PET-CT image of the patient with Gleevec-refractory GIST which shows a significant decrease in uptake during treatment with Compound 1, compared to time off therapy suggesting a treatment affect of Compound 1. Further information regarding this patient and the treatment protocol is set forth below:

Female patient, with a diagnosis of Gastro-intestinal Stromal Tumor (GIST). Patient had been previously treated as follows:

| Drug | Dose | Comments |
|---|---|---|
| Gleevec | Total daily dose between 200 to 800 mg | |
| BAY43-9006 | 400 mg twice daily | progressive disease |
| Brostallicin | 18 mg once daily | |
| Gleevec | 100 mg alternate days | drug resistant |
| Brostallicin | 12.8 mg once daily | |

The patient was enrolled in the study according to the inclusion and exclusion criteria of the protocol on Jun. 2, 2004, as set forth above.

Compound 1 treatment record:

| Dose | Frequency | Schedule |
|---|---|---|
| 75 mg | Once daily | 7 days on treatment)/7 days off |
| 100 mg | Once daily | 7 days on treatment)/7 days off |

The patient received a total dose of 9,625 mg (see table enclosed). The patient achieved stable disease (SD) while on treatment with Compound 1 (eight cycles completed).

As shown in FIG. 25, plasma exposure increases proportionally with dose of Compound 1 in patients. Plasma exposure in the 100 mg dose group approaches the range where preclinical efficacy has been noted.

Studies were carded out to identify a pharmacodynamic (PD) marker for Compound 1 biological activity using peripheral blood leukocytes (PDL) as a surrogate tissue in solid tumor patients where there is limited access to target tissue.

Rationale and Assay Development:

ERK phosphorylation is a well-characterized downstream effect of RTK activation and Compound 1 modulates ERK phosphorylation in tumor and endothelial cells.

To determine if Compound 1 affects ERK activation in PBL, blood from normal donors was treated ex vivo with Compound 1. No exogenous stimulation with PMA or PHA was added.

Figure 26:
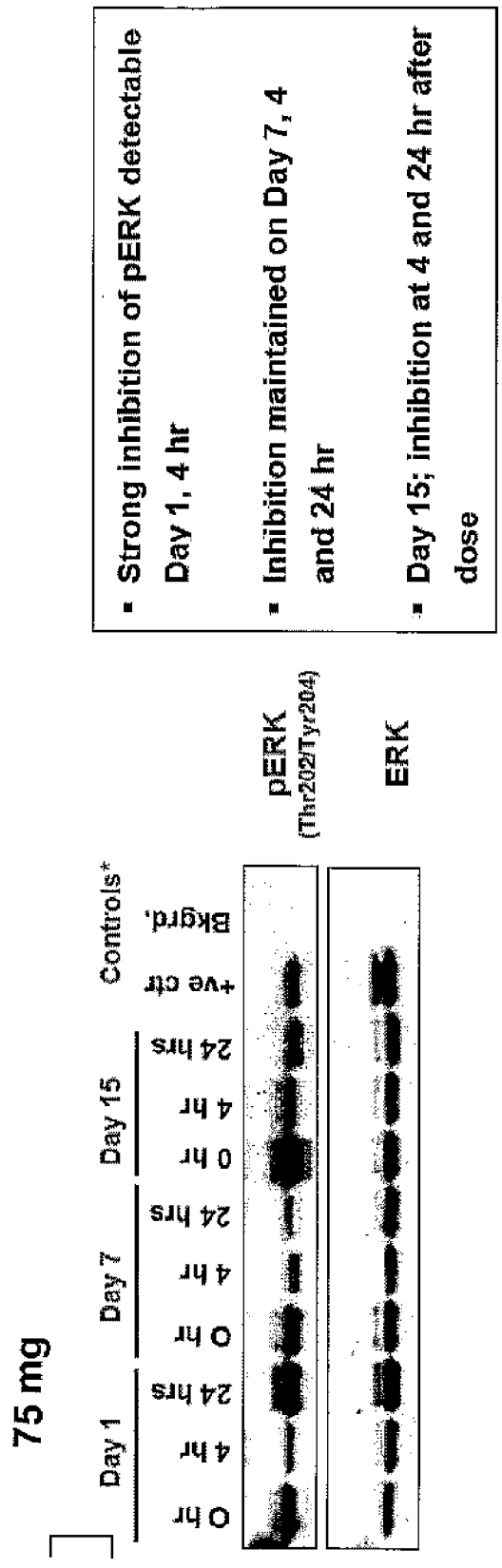
FIG. 26 is a scanned image of a Western Blot showing that 4-amino-5-fluoro-3-[6-(4-methylpiperazin-1-yl)-1H-benzimidazol-2-yl]quinolin-2(1H)-one inhibits basal ERK phosphorylation in peripheral blood leukocytes (PBL). Positive control samples were blood cells from a normal donor processed identically to clinical samples.

Dose dependent inhibition in endogenous pERK was observed by Western blot and flow cytometry assays after incubation of PBL with Compound 1 (See FIG. 26), suggesting that this assay may be useful in clinical trials to show Compound 1 is modulating its targets.

Compound 1 was tested against a panel of kinases, including a mutant form of ABL (T315I) that has been found to be resistant to Gleevec and other kinase inhibitors. See Shah, N. P. *Science,* 305, p. 399 (2004); and LaRosse, *Cancer Res.* 67, p. 7149-7153 (2002). The T315 residue in ABL is known as the "gatekeeper residue" and is located in a hydrophobic pocket in the ABL structure. This residue, as well as analogous positions of this residue in other kinases such as, but not limited to, Flt-3, KIT, PDGFRa, EGFR, and the like, are frequently found in patients that have replased to certain kinase inhibitors, such as patients that have become resistant to certain chemotherapeutic agents such as Gleevec, Iressa, Tarceva, and others. Thus, there is a medical need for alternative treatment strategies for these patients that have become resistant to these drugs. Compound 1 has been found to inhibit the T315I mutant of ABL with an $IC_{50}$ value of 0.0184 micromolar as compared to >10 micromolar for Gleevec and 0.371 micromolar for SU11248. ABL is a cytoplasmic tyrosine kinase. Therefore, the compounds of the invention have the ability to inhibit mutant kinases including receptor tyrosine kinases and cytoplasmic tyrosine kinases. Compounds of Formula I, II, and III may be used in patients with this mutation in ABL, either as an alternative treatment, or as a concurrent treatment with other anti-cancer drugs. Compound 1 has also been tested against a mutant form of FLT3 (D835Y). This residue is frequently mutated in patients with hematological malignancies. See Yamamoto, Y. *Blood,* 97, 2434 (2001). Thus, the compounds of Formula I, II, and III such as Compound 1 may also be used to treat patients with this mutation. Mutation of the gatekeeper residue in EGFR has recently been reported in lung cancer patients treated with gefitinib (Iressa). See Pao W., *PLos Med.* 2(3):e73 (2005).

Compound 1 is tested against other kinases with mutations in the "gatekeeper residue." Compound 1 is useful in treating cancer patients with these mutations. The following table shows $IC_{50}$ values of Compound 1 compared with Gleevec and SU11248.

| | | $IC_{50}$ values (micromolar) | | |
|---|---|---|---|---|
| Kinase | Note | Compound 1 | Gleevec | SU11248 |
| Abl_T315I | mutant ABL | 0.0184 | >10 | 0.371 |
| Alk | | 3.7 | >10 | 0.603 |
| Aurora_A | | 0.162 | 5.24 | 0.287 |
| Blk | | 0.036 | 0.475 | 0.203 |
| CamKII_alpha | | 4.54 | >10 | 2.89 |
| Cdk7_cyclinH_MAT1 | | 0.622 | 6.3 | 0.0343 |
| Ck1_delta | | 6.05 | 5.48 | 0.0497 |
| Ck1_gamma_2 | | >10 | >10 | 4.51 |
| Ck2 | | >10 | 0.488 | >10 |
| cRaf | | >10 | 4.18 | >10 |
| Erk1 | | >10 | >10 | >10 |
| Flt3_D835Y | | <0.001000000 | <0.001000000 | <0.001000000 |
| Hck | | 0.259 | 1.8 | 1.17 |
| Hyl | | 9 | >10 | >10 |
| JNK2_alpha_2 | | >10 | >10 | >10 |
| MLCK | | 3.63 | >10 | 0.304 |
| PAK2 | | >10 | >10 | >10 |
| PAK4 | | 7.94 | >10 | 9.25 |
| PHKG2 | | 8.11 | >10 | 0.535 |
| Pim1 | | >10 | | >10 |
| PKC_theta | | >10 | >10 | >10 |
| PKCe | | >10 | >10 | >10 |
| Ron | | >10 | >10 | >10 |
| ROS | | >10 | >10 | >10 |
| Syk | | 5.47 | >10 | >10 |
| TAK1 | | 0.0359 | >10 | 0.0373 |
| TRKC | | 0.00923 | 0.227 | 0.14 |
| TSSK1 | | 0.982 | >10 | 0.401 |
| ZAP70 | | >10 | >10 | >10 |
| CABL_CR/1//IC50 (uM) | wt ABL | 0.652 | 0.428 | 2.95 |
| FLT3_CR/1//IC50 (uM) | | 0.000085 | 1.26 | 0.000219 |
| Abl_T315I | mutant ABL | 0.0184 | >10 | 0.371 |

The assay for determining the $IC_{50}$ of ABL (T315I) was accomplished using the following procedure. In a final reaction volume of 25 μL, Abl (T315I) (h) (5-10 mU) is incubated with 8 mM MOPS pH 7.0, 0.2 mM EDTA, 50 μM EAIYAAP-FAKKK (SEQ ID NO. 7), 10 mM MgAcetate and $^{33}P$ gamma-labeled ATP (specific activity approximately 500 cpm/pmol, concentration as required). The reaction is initiated by the addition of the MgATP mixture. After incubation for 40 minutes at room temperature, the reaction is stopped by the addition of 5 μL of a 3% phosphoric acid solution. 10 μL of the reaction is then spotted onto a P30 filter mat and washed three times for 5 minutes in 75 mM phosphoric acid and once in methanol prior to drying and scintillation counting.

Other compounds of formula I such as compounds of formula II and formula III were prepared as described above and in the references cited herein. Studies using these compounds are carried out using the methodology described above for 4-amino-5-fluoro-3-[6-(4-methylpiperazin-1-yl)-1H-benzimidazol-2-yl]quinolin-2(1H)-one. These studies will show that these compounds are also useful in treating cancer, including drug-resistant cancer, in mice, human, and other mammalian subjects and may be used in combination with the anti-cancer drugs described herein.

It should be understood that the organic compounds according to the invention may exhibit the phenomenon of tautomerism. As the chemical structures within this specification can only represent one of the possible tautomeric forms at a time, it should be understood that the invention encompasses any tautomeric form of the drawn structure. For example, the compound having the formula IIIB is shown below with one tautomer, Tautomer IIIBa:

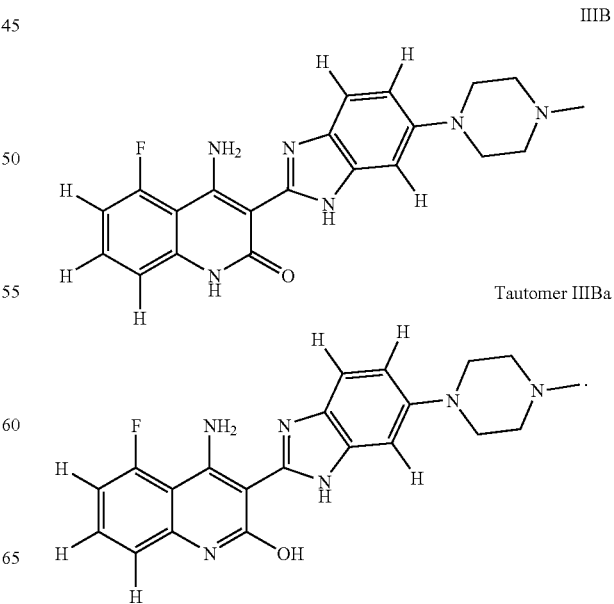

IIIB

Tautomer IIIBa

Other tautomers of the compound having the formula IIIB, Tautomer IIIBb and Tautomer IIIBc, are shown below:

Tautomer IIIBb

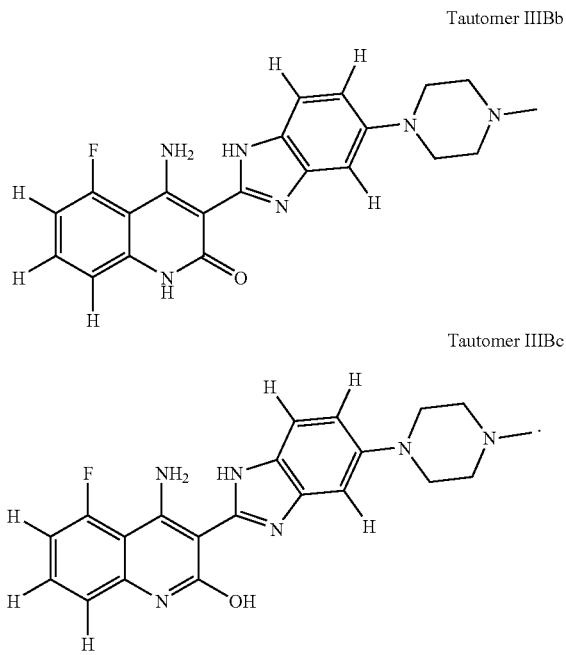

Tautomer IIIBc

The contents of each of the patents, patent applications and journal articles cited above are hereby incorporated by reference herein and for all purposes as if fully set forth in their entireties.

It is understood that the invention is not limited to the embodiments set forth herein for illustration, but embraces all such forms thereof as come within the scope of the following claims.

The invention claimed is:

1. A method of treating drug-resistant cancer comprising administering to a drug-resistant cancer subject in need thereof, a compound of formula II, a tautomer of the compound, a salt of the compound, a salt of the tautomer, a mixture thereof, or a pharmaceutical composition comprising the compound, the tautomer, the salt of the compound, the salt of the tautomer, or the mixture, by inhibiting a cytoplasmic tyrosine kinase or a receptor tyrosine kinase comprising a mutant gatekeeper residue in the subject, wherein the kinase is ABL, KIT, PDGFRa, EGFR, or FLT3, and wherein the cancer is resistant to an anti-cancer drug selected from the group consisting of imatinib mesylate, BAY43-9006, Brostallicin, erlotinib, gefitinib, and vatalanib, and further wherein the compound of formula II has the following formula:

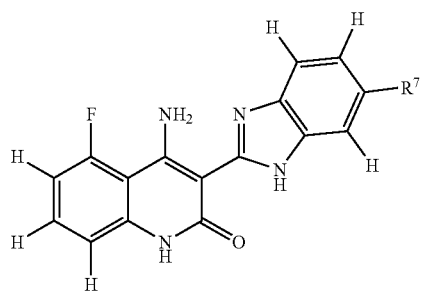

wherein $R^7$ is a substituted or unsubstituted heterocyclyl group selected from a substituted or unsubstituted piperidinyl group, piperazinyl group, or morpholinyl group.

2. The method of claim 1, wherein $R^7$ is a substituted or unsubstituted N-alkyl piperazinyl group.

3. The method of claim 1, wherein the alkyl group of the N-alkyl piperazinyl comprises from 1 to 4 carbon atoms.

4. The method of claim 1, wherein the compound of formula II is a compound of formula III:

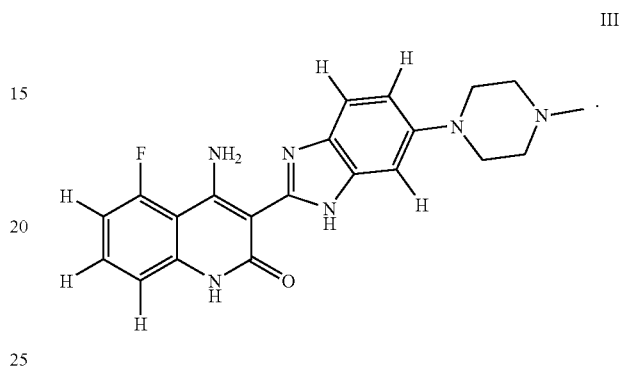

5. The method of claim 1, wherein the lactic acid salt of the compound is administered to the subject.

6. The method of claim 1, wherein the cancer is resistant to imatinib mesylate, BAY43-9006, or Brostallicin.

7. The method of claim 1, wherein the cancer is resistant to erlotinib, gefitinib, or vatalanib.

8. The method of claim 1, wherein the cancer is resistant to imatinib mesylate.

9. The method of claim 1, wherein the compound, the tautomer, the salt of the compound, the salt of the tautomer, the mixture, or the pharmaceutical composition is administered to the subject after imatinib mesylate has been administered to the subject and the cancer in the subject has been found to be resistant to imatinib mesylate.

10. The method of claim 1, wherein the compound, the tautomer, the salt of the compound, the salt of the tautomer, the mixture, or the pharmaceutical composition is administered to the subject after BAY43-9006 has been administered to the subject and the cancer in the subject has been found to be resistant to BAY43-9006.

11. The method of claim 1, wherein the compound, the tautomer, the salt of the compound, the salt of the tautomer, the mixture, or the pharmaceutical composition is administered to the subject after Brostallicin has been administered to the subject and the cancer in the subject has been found to be resistant to Brostallicin.

12. The method of claim 1 further comprising co-administering an anti-cancer drug selected from the group consisting of imatinib mesylate, BAY43-9006, Brostallicin, lenalidomide, thalidomide, docetaxel, erlotinib, vatalanib, VEGF-trap, fenretidine, bortezomib, bevacizumab, pertuzumab, and rituximab.

13. The method of claim 12, wherein the compound, the tautomer, the salt of the compound, the salt of the tautomer, the mixture, or the pharmaceutical composition is to be administered after the anti-cancer drug has been administered, before the anti-cancer has been administered or at same time that at least some of anti-cancer drug is administered.

14. The method of claim 1, wherein the drug-resistant cancer is selected from prostate cancer, renal cancer, gastrointestinal stromal tumor, sarcoma, colorectal cancer, breast cancer, parotid cancer, gastric cancer, melanoma, oesophageal cancer, NET (sinonasal) cancer, colon cancer, ovarian cancer, or liver cancer.

15. The method of claim 1, wherein the drug-resistant cancer is selected from gastrointestinal stromal tumor, acute myelogenous leukemia, chronic myelogenous leukemia, multiple myeloma, renal cell carcinoma, non-small cell lung cancer, or hypereosinophilic syndrome.

16. The method of claim 1, wherein the cancer is selected from chronic myelogenous leukemia, multiple myeloma, or renal cell carcinoma.

17. The method of claim 1, wherein the drug-resistant cancer is gastrointestinal stromal tumor.

18. The method of claim 1, wherein the kinase is ABL (T315I), FLT3(D835Y), or EGFR.

19. A method of treating drug-resistant cancer comprising administering to a drug-resistant cancer subject in need thereof a compound, a tautomer of the compound, a salt of the compound, a salt of the tautomer, a mixture thereof, or a pharmaceutical composition comprising the compound, the tautomer, the salt of the compound, the salt of the tautomer, or the mixture, by inhibiting a cytoplasmic tyrosine kinase or a receptor tyrosine kinase comprising a mutant gatekeeper residue in the subject, wherein the kinase is ABL, KIT, PDGFRa, EGFR, or FLT3, and wherein the drug-resistant cancer is selected from the group consisting of prostate cancer, renal cancer, gastrointestinal stromal tumor, sarcoma, colorectal cancer, breast cancer, parotid cancer, gastric cancer, melanoma, oesophageal cancer, NET (sinonasal) cancer, colon cancer, ovarian cancer, liver cancer, acute myelogenous leukemia, chronic myelogenous leukemia, multiple myeloma, renal cell carcinoma, non-small cell lung cancer, and hypereosinophilic syndrome, and further wherein the compound has the following formula:

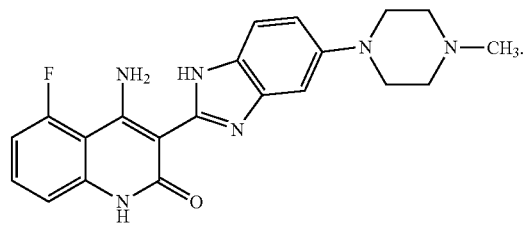

20. The method of claim 4, wherein the drug-resistant cancer is resistant to an anti-cancer drug selected from the group consisting of imatinib mesylate, BAY43-9006, Brostallicin, erlotinib, gefitinib, and vatalanib.

* * * * *